United States Patent
Sun et al.

(10) Patent No.: US 9,458,219 B2
(45) Date of Patent: Oct. 4, 2016

(54) HUMAN INSULIN ANALOGUE AND ACYLATED DERIVATIVE THEREOF

(71) Applicants: Shanghai Hengrui Pharmaceutical Co., Ltd., Shanghai (CN); Jiangsu Hengrui Medicine Co., Ltd., Lianyungang, Jiangsu (CN)

(72) Inventors: Piaoyang Sun, Lianyungang (CN); Lianshan Zhang, Lianyungang (CN); Jiajian Liu, Shanghai (CN); Jijun Yuan, Shanghai (CN); Chunqian Fang, Shanghai (CN); Changan Sun, Shanghai (CN); Hengli Yuan, Shanghai (CN); Yali Wang, Shanghai (CN)

(73) Assignees: Shanghai Hengrui Pharmaceutical Co., Ltd., Shanghai (CN); Jiangsu Hengrui Medicine Co., Ltd., Liangyungang, Jiangsu (CN)

( * ) Notice: Subject to any disclaimer, the term of this patent is extended or adjusted under 35 U.S.C. 154(b) by 0 days.

(21) Appl. No.: 14/363,328

(22) PCT Filed: Nov. 22, 2012

(86) PCT No.: PCT/CN2012/085054
§ 371 (c)(1),
(2) Date: Jun. 6, 2014

(87) PCT Pub. No.: WO2013/086927
PCT Pub. Date: Jun. 20, 2013

(65) Prior Publication Data
US 2014/0329745 A1    Nov. 6, 2014

(30) Foreign Application Priority Data
Dec. 15, 2011   (CN) .......................... 2011 1 0422095

(51) Int. Cl.
*A61K 38/28*    (2006.01)
*C07K 14/62*    (2006.01)
*C07K 14/435*   (2006.01)
*A61K 38/00*    (2006.01)

(52) U.S. Cl.
CPC ............. *C07K 14/62* (2013.01); *C07K 14/435* (2013.01); *A61K 38/00* (2013.01)

(58) Field of Classification Search
CPC ....... C07K 14/62; A61L 38/28; A61K 38/28
See application file for complete search history.

(56) References Cited

U.S. PATENT DOCUMENTS

| 5,008,241 A | 4/1991 | Markussen et al. |
| 5,164,366 A | 11/1992 | Balschmidt et al. |
| 7,060,675 B2 * | 6/2006 | Ekwuribe .............. A61K 38/28 514/6.2 |
| 7,193,035 B2 | 3/2007 | Berchtold |

FOREIGN PATENT DOCUMENTS

| CN | 86106574 A | 8/1988 |
| CN | 1133598 A | 10/1996 |
| CN | 1195777 A | 10/1998 |
| CN | 1780854 A | 5/2006 |
| CN | 1829738 A | 9/2006 |
| EP | 0419504 A1 | 4/1991 |
| EP | 0425482 A1 | 5/1991 |
| WO | WO 01/49742 | * 12/2001 |

OTHER PUBLICATIONS

Int'l Search Report issued on Feb. 28, 2013 in Int'l Application No. PCT/CN2012/085054.

* cited by examiner

*Primary Examiner* — Gyan Chandra
(74) *Attorney, Agent, or Firm* — Panitch Schwarze Belisario & Nadel LLP

(57) ABSTRACT

The present invention provides a human insulin analog, an acylated derivative thereof and a physiologically acceptable salt. The present invention further provides a preparation method for the insulin analog and an application of the insulin analog as a therapeutic agent, and particularly as a diabetes mellitus therapeutic agent.

23 Claims, 4 Drawing Sheets

HUMAN INSULIN ANALOGUE AND ACYLATED DERIVATIVE THEREOF

CROSS-REFERENCE TO RELATED APPLICATIONS

Figure 1:
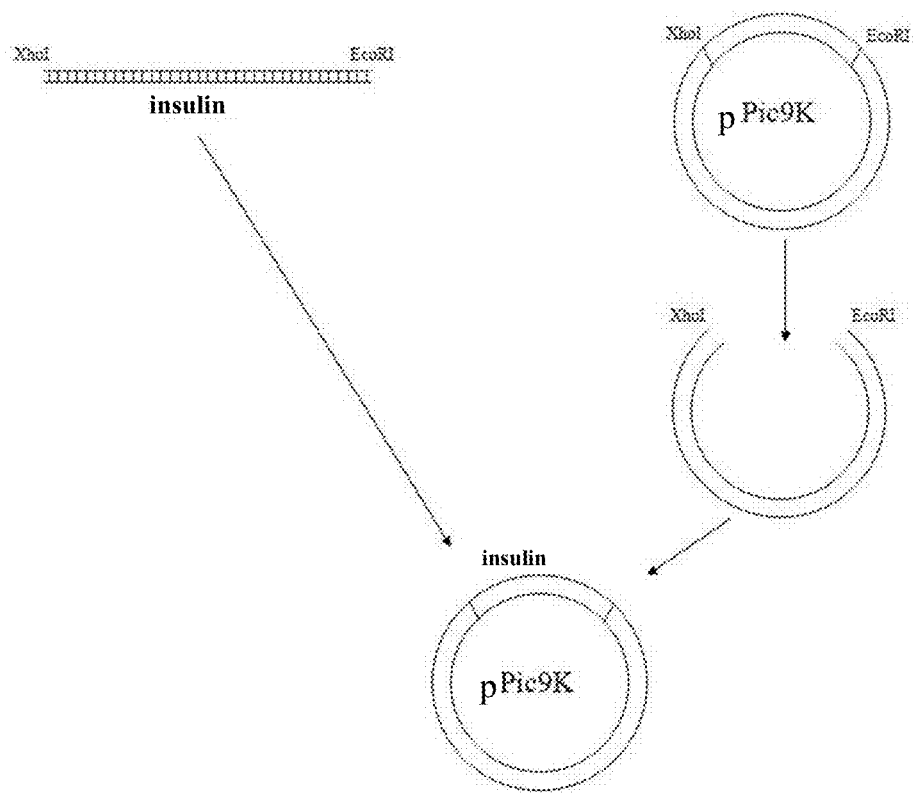

This application is a Section 371 of International Application No. PCT/CN2012/085054, filed on Nov. 22, 2012, which was published in the Chinese language on Jun. 20, 2013, under International Publication No. WO2013/086927, and the disclosure of which is incorporated herein by reference.

FIELD OF THE INVENTION

The present invention relates to a novel human insulin analogue and acylated derivatives thereof, preparation methods thereof, a pharmaceutical composition comprising the analogue and acylated derivatives thereof, and the use of the same as a therapeutic agent, especially as a diabetes therapeutic agent.

BACKGROUND OF THE INVENTION

Diabetes (Diabetes Mellitus, DM) is a common metabolic endocrine disease. It is a clinically chronic and systemically metabolic syndrome, characterized by chronic hyperglycemia, disturbance of carbohydrate, fat and protein metabolism resulting from absolute or relative insulin deficiency, or insensitivity of the target tissues to insulin. It is caused by the interaction of genetic and environmental factors, involving various body systems, including cardio-cerebrovascular, kidney, eye, nerve, and other organ complications. It's a lifelong disease, and is seriously harmful to human health.

Diabetes is a common, frequently occurring disease, and it has become the third largest common disease threatening human lives following cancer and cardiovascular disease. It is a challenge to the world. DM is harmful to people's health regardless of race and nation. According to the statistics from the International Diabetes Federation (IDF), during the ten years from the mid-1980s to the mid-1990s of the last century, the total number of diabetics increased 4-fold, up to 120 million. In 2007, the global number of diabetics was 246 million, of which 46% were 40-59 years old and of the labor force population. It is anticipated that in 2025, the global number of diabetics will increase to 380 million, accounting for 7.1% of the global adult population.

According to the data announced by ADA (American Diabetes Association) in January 2011, there are 25.6 million diabetics in the United States, accounting for 8.3% of the U.S. population. Among the huge medical cost in the United States, one of every 10 dollars is spent on diabetes. In China, the number of diabetics increased significantly for the past 20 years. Epidemiological investigations revealed the prevalence of diabetes was less than 4% before 2002. Recently, a national epidemiological survey of diabetes showed that the prevalence of diabetes among Chinese adults (20 years of age or older) is more than 10%. The overall prevalence of diabetes was 9.7%. Currently, there are more than 92 million people suffering from diabetes, and another 100 million and 5000 people will become diabetics. China is becoming the country having the largest number of diabetic patients, instead of India.

Diabetes is mainly divided into insulin-dependent diabetes mellitus (type I diabetes), insulin-independent diabetes mellitus (type II diabetes), as well as other special types of diabetes. Type I diabetes mainly occurs in children and adolescents, the peak age is 12 years old, accounting for less than 10% of diabetics. Type II diabetes mainly occurs in adults, accounting for more than 90% of diabetics. The exact pathological mechanisms underlying diabetes is still unknown, there is no cure for diabetes. Currently, therapy for diabetes focuses on drug treatment and control. For a small portion of patients suffering from type II diabetes, diet and exercise therapy can be used to control the condition, whereas for the vast majority of patients, drug therapy is necessary. Drug therapy includes Chinese medicine and chemical medicine. Chemical medicine is predominant, and is divided into two categories: protein and polypeptide drugs as represented by insulin and analogues thereof, and small molecule anti-diabetic drugs for oral administration.

With the dramatic increase in the number of diabetic patients worldwide, the global diabetes drug market is also rapidly growing. According to statistics, in 2005 the diabetes drug market reached $18.6 billion, an increase of 11.5% compared to the previous year. In 2006, it was $21.2 billion, an increase of 14%. In 2007, it was $24.1 billion, an increase of 13.7%, ranking fifth in the global pharmaceutical market. 15 to 20 percent annual growth rate is predicted. Research and Markets reports that insulin and analogues thereof account for 40.1% of the total diabetes drug market, oral hypoglycemic drugs account for 58%, and other drugs share the remaining 1.9%.

A series of patent applications have disclosed some insulin analogues, which comprise amino acid substitutions at various sites of natural human insulin sequences. European Patent EP0425482B1 discloses an insulin analogue having a histidine (His) or tyrosine (Tyr) substitutions at position B25. European Patent EP0419504B1 discloses an insulin analogue having a substitution at position B3, and simultaneously having a glutamine (Gln) substitution at A5 or A15, or alternatively, an asparagine (Asn) substitution at A21 or A18. U.S. Pat. No. 5,008,241A discloses an insulin analogue having a specific amino acid substitution at A21, as well as a specific amino acid substitution at A4, A17, B13 or B21. U.S. Pat. No. 5,164,366A discloses an insulin analogue having amino acid deletion at one of positions B24, B25, B26 and B27. Chinese Patent CN1195777C discloses an insulin analogue having substitutions at positions A8, A9, A10, and B30. U.S. Pat. No. 7,193,035B2 discloses a crystalline insulin analogue having a substitution at position B3 and at least one substitution at one of positions B27, B28 and B29. Chinese Patent Application CN1780854A discloses an insulin analogue of A0 (Arg), A21 (Gly), B31 (Arg), and B32 (Arg).

Nevertheless, in order to achieve a better modification effect, to get a better efficacy, to decrease the binding activity between drugs and insulin-like growth factor-1 (IGF-1) receptor, and to provide more selective drugs, additional modified insulin analogues are still required for the treatment of diabetes.

SUMMARY OF THE INVENTION

Accordingly, the present invention is to provide novel drugs having excellent properties for diabetes treatment. More specifically, the present invention provides novel human insulin analogues and acylated derivatives thereof, and preparation methods for the analogues and derivatives, pharmaceutical compositions comprising the same, and use of the human insulin derivatives for the treatment of diabetes.

In one aspect, the present invention is directed to a human insulin analogue and a physiologically acceptable salt thereof, having an A chain and B chain as follows:

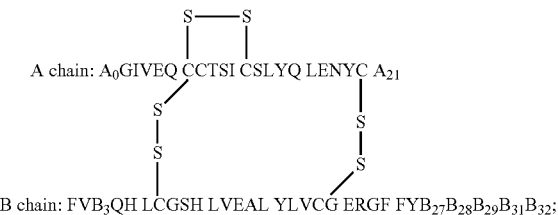

A chain: $A_0$GIVEQ CCTSI CSLYQ LENYC $A_{21}$

B chain: FV$B_3$QH LCGSH LVEAL YLVCG ERGF FY$B_{27}B_{28}B_{29}B_{31}B_{32}$;

wherein:
$A_0$ is R or omitted;
$A_{21}$ is N or G;
$B_3$ is K, D or N;
$B_{27}$ is E, T, D or K;
$B_{28}$ is E, D, P or K;
$B_{29}$ is E, K or P;
$B_{30}$ is K, R, E, T or omitted;
each of $B_{31}$ and $B_{32}$ is R, optionally omitted or both are omitted;
wherein,
when $A_0$ is omitted, $A_{21}$ is N, and $B_3$ is N:
$B_{31}B_{32}$ are omitted, and $B_{27}B_{28}B_{29}B_{30}$ are not TPKT, TKPT or TDKT;

or $B_{30}B_{31}B_{32}$ are omitted, and $B_{27}B_{28}B_{29}$ are not TPK;
or alternatively, when $A_0$ is omitted, $A_{21}$ is N, $B_3$ is K, and $B_{31}B_{32}$ are omitted,
$B_{27}B_{28}B_{29}B_{30}$ are not TEKT;
or alternatively, when $A_0$ is omitted, $A_{21}$ is G, and $B_3$ is N, $B_{27}B_{28}B_{29}B_{30}B_{31}B_{32}$ are not TPKTRR.

Preferably, only one amino acid residue of positions $B_3$, and $B_{27}$-$B_{30}$ is a lysine (K) residue.

When $A_0$ on A chain is omitted, and $B_3$ on B chain is N:
$B_{28}$ is preferably selected from E or D, $B_{29}$ is selected from E, K or P, $B_{30}$ is selected from R, E or omitted, and $B_{31}B_{32}$ are omitted; more preferably, when $B_{30}B_{31}B_{32}$ are omitted, $B_{28}B_{29}$ are KE.

When $B_3$ on B chain is D, $B_{28}$ and $B_{29}$ are preferably P or K, $B_{30}$ is T or omitted, $B_{31}$ and $B_{32}$ are R or omitted, most preferably $B_{28}B_{29}$ are PK.

When $A_0$ on A chain is omitted and $B_3$ on B chain is K:
$B_{28}$ and $B_{29}$ are preferably P or E, $B_{30}$ is E or R, $B_{31}$ is R or omitted, $B_{32}$ is omitted, most preferably, $B_{28}B_{29}$ are PE.

The present invention provides a human insulin analogue or a physiologically acceptable salt thereof, wherein the A chain and the B chain of the human insulin analogue are connected by a disulfide bond (A7-B7, A20-B19), and A6 and A11 on the A chain are connected by disulfide bond. The sequences are selected from, but not limited to, the following sequences:

| NO | Sequences of Insulin Analogue | Abbreviation of Insulin Analogue |
|----|-------------------------------|----------------------------------|
| 1 | A chain: RGIVEQCCTSICSLYQLENYCN<br>B chain: FVNQHLCGSHLVEALYLVCGERGFFYTPK | B(1-29),<br>R-A(1-21) |
| 2 | A chain: GIVEQCCTSICSLYQLENYCN<br>B chain: FVNQHLCGSHLVEALYLVCGERGFFYTKER | B(1-27)-K-E-R,<br>A(1-21) |
| 3 | A chain: GIVEQCCTSICSLYQLENYCN<br>B chain: FVNQHLCGSHLVEALYLVCGERGFFYTKE | B(1-27)-K-E,<br>A(1-21) |
| 4 | A chain: GIVEQCCTSICSLYQLENYCN<br>B chain: FVNQHLCGSHLVEALYLVCGERGFFYTKPE | B(1-27)-K-P-E,<br>A(1-21) |
| 5 | A chain: GIVEQCCTSICSLYQLENYCN<br>B chain: FVKQHLCGSHLVEALYLVCGERGFFYTPEE | B(1-2)-K-B(4-28)-<br>E-E, A(1-21) |
| 6 | A chain: GIVEQCCTSICSLYQLENYCN<br>B chain: FVNQHLCGSHLVEALYLVCGERGFFYTDKE | B(1-27)-D-K-E,<br>A(1-21) |
| 7 | A chain: GIVEQCCTSICSLYQLENYCG<br>B chainFVDQHLCGSHLVEALYLVCGERGFFYTPKTRR | B(1-2)-D-B(4-30)-<br>R-R, A(1-20)-G |
| 8 | A chain: RGIVEQCCTSICSLYQLENYCG<br>B chain: FVDQHLCGSHLVEALYLVCGERGFFYTPKTR | B(1-2)-D-B(4-30)-R,<br>R-A(1-20)-G |
| 9 | A chain: GIVEQCCTSICSLYQLENYCN<br>B chain: FVKQHLCGSHLVEALYLVCGERGFFYTPERR | B(1-2)-K-B(4-28)-<br>E-R-R, A(1-21) |
| 10 | A chain: GIVEQCCTSICSLYQLENYCN<br>B chain: FVDQHLCGSHLVEALYLVCGERGFFYTPK | B(1-2)-D-B(4-29),<br>A(1-21) |
| 11 | A chain: RGIVEQCCTSICSLYQLENYCN<br>B chain: FVDQHLCGSHLVEALYLVCGERGFFYTPK | B(1-2)-D-B(4-29),<br>R-A(1-21) |
| 12 | A chain: GIVEQCCTSICSLYQLENYCG<br>B chain: FVNQHLCGSHLVEALYLVCGERGFFYTKE | B(1-27)-K-E,<br>A(1-20)-G |
| 13 | A chain: GIVEQCCTSICSLYQLENYCG<br>B chain: FVKQHLCGSHLVEALYLVCGERGFFYTPEE | B(1-2)-K-B(4-28)-<br>E-E, A(1-20)-G |
| 14 | A chain: GIVEQCCTSICSLYQLENYCG<br>B chain: FVDQHLCGSHLVEALYLVCGERGFFYTPKR | B(1-2)-D-B(4-29)-R,<br>A(1-20)-G |

-continued

| NO | Sequences of Insulin Analogue | Abbreviation of Insulin Analogue |
|----|-------------------------------|----------------------------------|
| 15 | A chain: GIVEQCCTSICSLYQLENYCG<br>B chain: FVDQHLCGSHLVEALYLVCGERGFFYTPK | B(1-2)-D-B(4-29),<br>A(1-20)-G |
| 16 | A chain: RGIVEQCCTSICSLYQLENYCG<br>B chain: FVDQHLCGSHLVEALYLVCGERGFFYTPK | B(1-2)-D-B(4-29),<br>R-A(1-20)-G |
| 17 | A chain: GIVEQCCTSICSLYQLENYCG<br>B chain: FVNQHLCGSHLVEALYLVCGERGFFYTDKE | B(1-27)-D-K-E,<br>A(1-20)-G |

In another aspect, the present invention also provides a preferred example of the above human insulin analogue or a physiologically acceptable salt thereof, wherein the human insulin analogue is PEGylated so as to obtain a PEGylated insulin according to the present invention. The molecular weight of the PEG molecule is 5-100 kD, preferably 10-80 kD, more preferably 15-45 kD, and most preferably 20-40 kD. The PEG molecule is a branched-chain or straight-chain type.

The present invention also provides a preparation method for a human insulin analogue or physiologically acceptable salt thereof, comprising constructing an expression vector, expressing the vector transformed into host cells, isolating and purifying the expressed precursor, and releasing the insulin analogue from the expressed precursor via chemical and/or enzymatic methods. Optionally, the human insulin analogue is further PEGylated, the PEGylation method is preferably a chemically acylating modification method, which comprises synthesizing an acylating agent, acylating the amino group located on human insulin analogues, and removing the protecting group from the acylated group.

The expressed precursor has the following formula (I):

B-R1-A                                   (I)

wherein:
R1 is a peptide fragment having 0 to 5 amino acid residues, the peptide fragment consists of alanine (A), lysine (K), and arginine (R); and
A and B correspond to A chain and B chain of human insulin analogue, respectively.

Preferably, the precursor is selected from the group consisting of:

FVNQHLCGSHLVEALYLVCGERGFFYTDKEKRGIVEQCCTSICSL

YQLENYCN,

SEQ ID NO: 20
FVKQHLCGSHLVEALYLVCGERGFFYTPEEKRGIVEQCCTSICSL

YQLENYCG,

SEQ ID NO: 21
FVKQHLCGSHLVEALYLVCGERGFFYTPEEKRGIVEQCCTSICSL

YQLENYCN,
and

SEQ ID NO: 77
FVNQHLCGSHLVEALYLVCGERGFFYTDKEKRGIVEQCCTSICSL

YQLENYCG.

The present invention also provides a DNA encoding the expressed precursor.

The present invention also provides an expression vector comprising the DNA.

The present invention also provides a host cell transformed with the expression vector.

The host cell is preferably a bacterium, more preferably *Escherichia coli*.

Preferably the host cell is yeast, more preferably *Pichia pastoris* or *Saccharomyces cerevisiae*.

The present invention also provides an insulin derivative, wherein acylated insulin is formed by connecting an acylated group to the α-amino group at the N-terminus of the A chain or B chain of the insulin, or to the ε-amino group of a lysine (K) residue at B3, B27-B30, the acylated insulin has the following formula:

wherein S is insulin or an insulin analogue according to the first aspect;
-W-X—Y—Z is an acylated group of the insulin analogue, wherein, W is selected from
    a group having a di-acyl structure of —OC(CH2)mCO—, wherein m is an integer between 2 and 10, an amide bond is formed between one of the carboxyl groups on the structure and the α-amino group of the N-terminal amino acid residue of A-chain or B-chain of the parent insulin or analogue thereof, or the ε-amino group of a Lys residue existing in B-chain; and
    an α-amino acid residue with a carboxyl group on the side chain, or a peptide having 2 to 4 α-amino acids with a carboxyl group on the side chain, wherein an amide bond is formed between the residue or the peptide and the α-amino group at the N-terminus of A-chain or B-chain of the parent insulin or analogue thereof, or the ε-amino group of a Lys residue existing in B-chain;
X is selected from
    —CO—; and
    a diamino compound comprising a carboxyl group, wherein an amide bond is formed between one of the α-amino groups of the diamino compound and the carboxyl group of W;
    a) when W is an α-amino acid residue or a peptide having 2 to 4 α-amino acids, an amide bond is formed between the amino group of W and the —CO— of X;
    b) when W is a group having a di-acyl structure, the X group is linked to the di-acyl structure via one of its amino groups;
Y is selected from
    -A(CH$_2$)$_m$—, wherein m is an integer between 6 and 32, and A is omitted or is CO—;
    bivalent hydrocarbon chain comprising an acyl group, which comprises 1, 2 or 3 —CH═CH— groups and several —CH2- groups sufficient to obtain a total of 10-32 carbon atoms in the chain; and bivalent hydrocarbon chain having the formula of —B(CH$_2$)$_v$C$_6$H$_4$(CH$_2$)$_w$—, wherein B is absent or is CO—, v and w are integers or one of them is 0, making v and w in the range of 6 to 30;

a) when X is CO—, A or B is missing; or
b) when X is a diamino compound, A or B is CO—;

Z is selected from the group consisting of —OH, —NH$_2$, —COOH, —SO$_3$H, and —PO$_3$H.

Preferably, the present invention provides an insulin derivative, wherein the acylated group -W-X—Y—Z is connected to the ε-amino group at a lysine (K) residue of B3 or B27 to B30 of the parent insulin.

Preferably, the insulin derivative is as above, wherein the acylated group -W-X—Y—Z is connected to the α-amino group at the N-terminus selected from A chain and B chain of insulin.

Preferably, the present invention provides an insulin derivative, wherein S is a human insulin analogue selected from the group consisting of:

```
A chain:
                                      SEQ ID NO: 1
GIVEQCCTSICSLYQLENYCN B chain:
                                      SEQ ID NO: 10
FVNQHLCGSHLVEALYLVCGERGFFYTDKE A chain:
                                      SEQ ID NO: 1
GIVEQCCTSICSLYQLENYCN B chain:
                                      SEQ ID NO: 9
FVKQHLCGSHLVEALYLVCGERGFFYTPEE
and A chain:
                                      SEQ ID NO: 2
GIVEQCCTSICSLYQLENYCG B chain:
                                      SEQ ID NO: 16
FVKQHLCGSHLVEALYLVCGERGFFYTPEE
```

Preferably, the present invention provides an insulin derivative, wherein the acylated group -W-X—Y—Z is selected from the group consisting of:
N$^\alpha$—(HOOC(CH$_2$)$_{14}$CO)-γ-Glu;
N$^\alpha$—(HO(CH$_2$)$_{15}$CO)-γ-Glu; and
N$^\alpha$—(HOOC(CH$_2$)$_{14}$CO)—N$^\epsilon$-(3-acyl acid *)-Lys,
in which * is the connection point for the insulin.

Preferably, the present invention provides an insulin derivative selected from the group consisting of:
B28D-N$^{\epsilon B29}$—(N$^\alpha$—(HOOC(CH$_2$)$_{14}$CO)-γ-Glu)-B30E human insulin (code: HS061);
B28D-N$^{\epsilon B29}$—(N$^\alpha$—(HO(CH$_2$)$_{15}$CO)-γ-Glu)-B30E human insulin (code: HS062);
N$^\alpha$—(HOOC(CH$_2$)$_{14}$CO)—N$^\epsilon$—(OCCH$_2$CH$_2$CO-(B28D-N$^{\epsilon B29}$-B30E human insulin))-Lys-OH (code: HS067);
N$^{\epsilon B3}$—(N$^\alpha$—(HOOC(CH$_2$)$_{14}$CO)-γ-Glu)-B29E-B30E human insulin; (code: HS605)
N$^\alpha$—(HOOC(CH$_2$)$_{14}$CO)—N$^\epsilon$—(OCCH$_2$CH$_2$CO—(N$^{\epsilon B3}$-B29E-B30E human insulin))-Lys-OH (code: HS606);
N$^{\epsilon B3}$—(N$^\alpha$—(HOC(CH$_2$)$_{15}$CO)-γ-Glu)-B29E-B30E human insulin)) (code: HS607);
N$^{\epsilon B3}$—(N$^\alpha$—(HOOC(CH$_2$)$_{14}$CO)-γ-Glu)-B29E-B30E, A21G human insulin (code: HS608);
N$^\alpha$—(HOOC(CH$_2$)$_{14}$CO)—N$^\epsilon$—(OCCH$_2$CH$_2$CO—(N$^{\epsilon B3}$-B29E-B30E, A21G human insulin)-Lys-OH (code: HS609); and
N$^{\epsilon B3}$—(N$^\alpha$—(HOC(CH$_2$)$_{15}$CO)-γ-Glu)-B29E-B30E, A21G human insulin (code: HS610).

The present invention also provides a pharmaceutical formulation comprising an insulin analogue and/or pharmaceutically acceptable salts thereof according to the invention, or an insulin derivative as described above.

Preferably, the pharmaceutical formulation comprises a human insulin analogue or a physiologically acceptable salt thereof present in dissolved, amorphous and/or crystalline forms.

Preferably, the pharmaceutical formulation comprises a long-term adjuvant, the long-term adjuvant is present along with the medicament in a manner of co-crystallization.

The present invention also provides an injectable solution having insulin activity, wherein the solution comprises the pharmaceutical formulation present in dissolved form.

The present invention also provides use of the human insulin analogue and/or a physiologically acceptable salt thereof, or insulin derivative in the preparation of a medicament for the treatment of type II diabetes, hyperglycemia, obesity, or insulin resistance syndrome.

The present invention also provides use of the human insulin analogue and/or a physiologically acceptable salt thereof, in the preparation of a quick-acting and/or long-acting pharmaceutical formulation having insulin activity.

The present invention provides novel human insulin analogues with good modification effects and better pharmacological activity, and provides more drugs for clinical options for treatment of diabetes.

TERMS

As used herein, the single-letter code and the three-letter code for amino acids are as described in *J. Biol. Chem*, 243, (1968) p3558.

In the DNA sequences, A refers to adenine, C refers to cytosine, G refers to guanine, and T refers to thymine.

"Human insulin analogue" refers to human insulin, wherein one or more amino acid residues has been deleted and/or replaced with other amino acid residues. Alternatively, additional amino acid residues are introduced, i.e., the number of amino acid residues is more than 51.

"Insulin derivative" herein refers to acylated insulin formed by connecting an acylated group to the α-amino group at the N-terminus of the A chain or B chain of insulin, or to the ε-amino group at a lysine residue at B3 or B27-B30. The acylated insulin has the following formula: S-W-X—Y—Z, wherein each code is defined in the specification.

"PEGylated insulin" refers to PEGylated human insulin analogue, wherein the PEG molecule has a molecular weight of 5-100 kD, preferably 10-80 kD, more preferably 15-45 kD, most preferably 20-40 kD, wherein the PEG molecule is branched- or straight-chain type. In the present invention, PEGylated (20 kD) insulin means that each subunit of the human insulin analogue is conjugated with a 20 kD PEG molecule; PEGylated (30 kD) insulin means that each subunit of the human insulin analogue is conjugated with a 30 kD PEG molecule; PEGylated (branched type 40 kD) insulin means that each subunit of the human insulin analogue is conjugated with a 40 kD branched PEG molecule.

"Long-acting adjuvant" refers to protamine sulfate.

"A quick-acting pharmaceutical formulation having insulin activity" refers to the formulation comprising a human insulin analogue or a physiologically acceptable salt thereof having quick-acting insulin activity.

"A long-acting pharmaceutical formulation having insulin activity" refers to the formulation comprising a human insulin analogue or a physiologically acceptable salt thereof having long-acting insulin activity.

Sequences in the present invention are designed on the basis of amino acid sequences of natural human insulin. Full length human insulin comprises two chains of A and B. The A chain and B chain are linked via a disulfide bond, and there is another disulfide bond in the A chain. The human insulin has three disulfide bonds, marked with lines. Serial numbers of amino acids on each chain are indicated according to the following rules: for example, amino acid residues on positions 1-21 of A chain are labeled as A1, A2, A3 . . . ; amino acid residues on positions 1-30 of B chain are labeled as B1, B2, B3 . . . . In addition, if amino acid residues are added to the N-terminus of A chain or B chain, such amino acid residues are labeled as A0, A (−1), A (−2), and B (0), B (−1), B (−2) . . . , respectively. If amino acid residues are added to the C-terminus of A chain or B chain, such amino acid residues are labeled as A22, A23, . . . , and B31, B32, . . . , respectively. To represent a specific formula of human insulin analogue, the determined amino acid is presented by amino acid code, while the unknown substitution or deletion of amino acid is presented by the serial number of the position, as shown in the formula of the present invention.

In embodiments of the present invention, B (1-29) as used herein refers to a shortened B chain consisting of B1 to B29 of human insulin, B (1-30) refers to B chain consisting of B1 to B30 of human insulin, B (1-31) refers to B chain consisting of B1 to B31 of human insulin, B (1-32) refers to shortened B chain consisting of B1 to B32 of human insulin; A (1-21) refers to A chain of human insulin, A (0-21) refers to A chain of human insulin having an additional amino acid residue at position A0. According to a particular embodiment of the present invention, a substituted residue in the human insulin is represented with the serial number of human insulin. For example, B (1-2)-D-B-(4-30), A(1-21) human insulin refers to a human insulin analogue, wherein N is replaced with D at position 3 of B-chain. Unless indicated otherwise, the abbreviation of B (1-30), A (1-21) refers to natural human insulin; B (1-29), A (1-21) refers to human insulin analog having the deletion at position B30; B(1-2)-K-B(4-28)-E-E, A(1-21) means human insulin analog having a substitution K at position B3, and substitutions EE is positions B29B30 (Example 6). Furthermore, as in human insulin, B chain and A chain of a human insulin analogue are connected via interchain disulfide bonds formed between A (7) Cys and B (7) Cys, and between A (20) Cys and B (19) Cys. Simultaneously, A chain contains an intrachain disulfide bond formed between A (6) Cys and A (11) Cys.

According to the present invention, transformation of the recombinant DNA into a host cell is performed by conventional techniques well known to the skilled person in the art. The obtained transformant can be cultured by a conventional method to express polypeptide encoded by the gene according to the present invention. Dependent on the host cell used, the culture medium used can be selected from various conventional culture media. The host cells are cultured under conditions suitable for growing. Chemical and/or enzymatic methods used for releasing insulin analogue from the expressed precursor are conventional techniques well known to the skilled person in the art, such as the use of trypsin, carboxypeptidase B, lysine endopeptidase C, etc.

BRIEF DESCRIPTION

Figure 2:
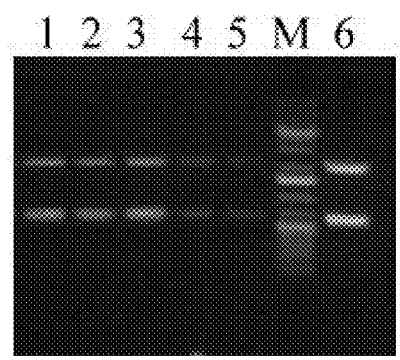

FIG. 1 displays a schematic diagram for cloning recombinant human insulin B (1-30), A (1-21) precursor;

FIG. 2 displays electrophoretic results after PCR amplification of the inserted recombinant human insulin B (1-30), A (1-21) precursor fragment.

Figure 3:
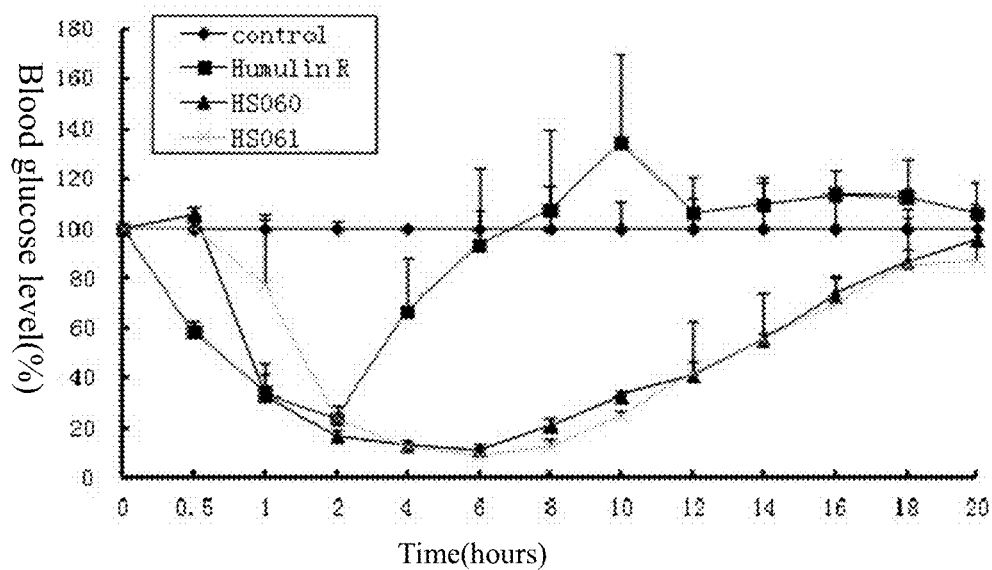
Figure 4:
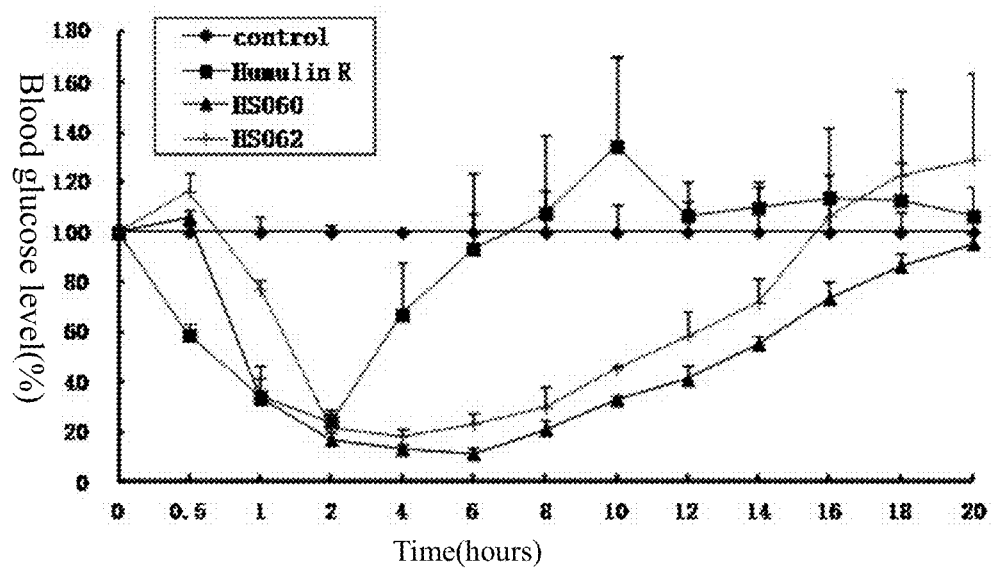
Figure 5:
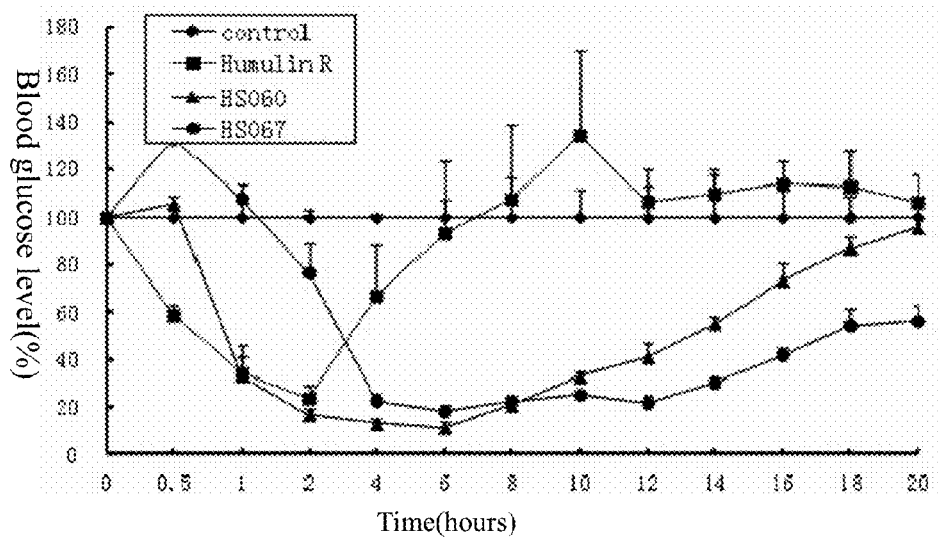
Figure 6:
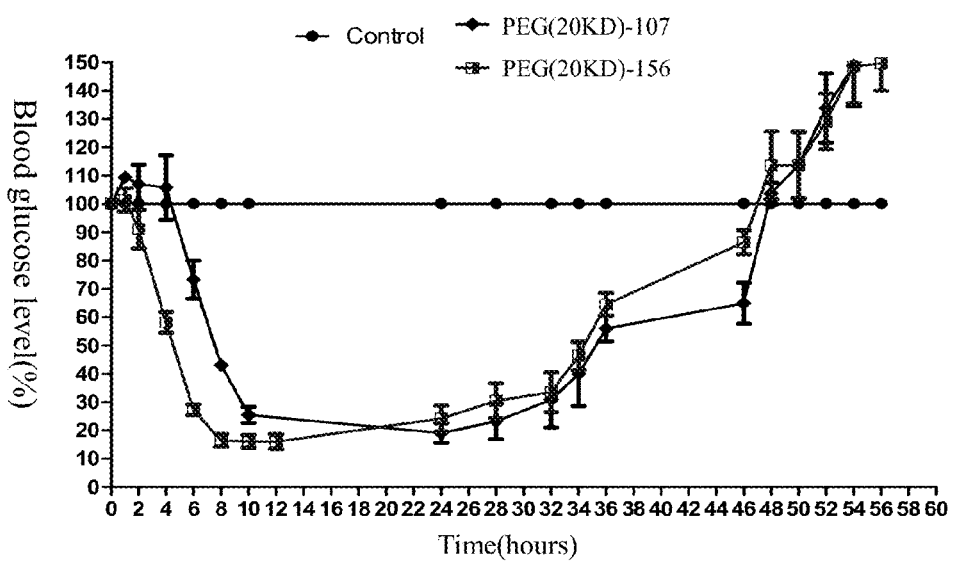
Figure 7:
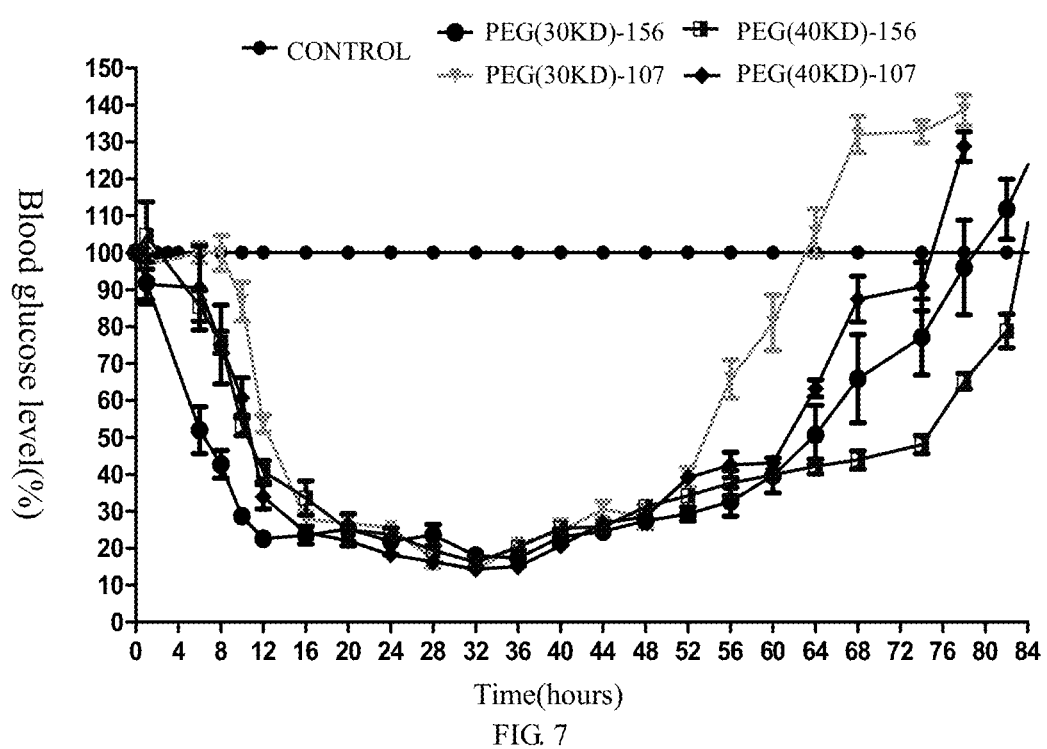

FIG. 3 displays the comparative results of in vivo long-lasting activity assay of HS061 and HS060;

FIG. 4 displays comparative results of in vivo long-lasting activity assay of HS062 and HS060;

FIG. 5 displays comparative results of in vivo long-lasting activity assay of HS067 and HS060;

FIG. 6 displays in vivo long-lasting activity assay of PEGylated (20 kD) B (1-27)-D-K-E, A (1-21) (PEG (20 kD)-156), and PEGylated (20 kD) B(1-2)-K-B(4-28) E-E, A(1-21) (PEG (20 kD)-107); and FIG. 7 displays in vivo long-lasting activity assay of PEG(30 kD)-107, PEG (40 kD)-107, PEG (30 kD)-156, and PEG (40 kD)-156.

DETAILED DESCRIPTION OF THE INVENTION

The present invention is further described by the following Examples which are not intended to limit the scope of the invention.

The reagent formulations used in the present invention are as follows:

YPD broth (1 L) (1% yeast extract, 2% peptone, 2% glucose):

1. 10 g yeast extract, 20 g peptone were dissolved in 900 mL water;
2. Autoclaved for 20 min;
3. 100 mL of 20% sterile glucose were added.

Basic glucose medium (1 L) (1.34% YNB; $4 \times 10^{-5}$% biotin; 2% glucose):

1. 800 mL water were autoclaved for 20 min, (in order to prepare an Agar Plate, 15 to 20 g agar can be added prior to autoclaving);
2. Cooled to 60° C., followed by adding 100 mL sterile 10×YNB, 2 mL sterile 0.02% biotin, and 100 mL of 20% sterile glucose.

BMMY liquid medium (1 L):

1. 10 g of yeast extract, 20 g peptone were dissolved in 700 mL of water;
2. Autoclaved for 20 min;
3. Cooled to room temperature, followed by adding and mixing the following substances:

100 mL sterile 1M potassium phosphate buffer, pH 6.0; 100 mL sterile 10×YNB, 2 mL sterile 0.02% biotin, 100 mL sterile 5% methanol.

Medium to induce expression (1 L) (BMGY):

1. 10 g of yeast extract, 20 g peptone were dissolved in 700 mL of water;
2. Autoclaved for 20 min;
3. Cooled to room temperature, followed by adding and mixing the following substances:

100 mL sterile 1M potassium phosphate buffer, pH6.0; 100 mL sterile 10×YNB, 2 mL sterile 0.02% biotin, 100 mL sterile 10% glycerol.

The Examples described herein were generally performed in accordance with conventional conditions, e.g., Sambrook et al, Molecular Cloning: A Laboratory Manual (New York: cold spring harbor laboratory press, 1989); *Pichia* yeast Expression Laboratory Manual (version: 10 Apr. 2009), or performed following the recommendation by the manufacturer of the product, if the specific conditions were not indicated. The reagents used herein were routinely purchased from the manufacturer. The Unit of molecular weight mentioned in the following examples of the present invention is daltons (Dalton).

EXAMPLES

Example 1

Preparation of Recombinant Human Insulin B(1-30), A(1-21) and B(1-29), R-A(1-21)

Step 1:
Cloning and Expression of Recombinant Human Insulin B(1-30), A(1-21) Precursors
1. Construction of an Expression Vector Having Recombinant Human Insulin B(1-30), A(1-21) Precursors:

The genes encoding for the recombinant human insulin B(1-30), A(1-21) precursors were synthesized by using three rounds of polymerase chain reaction (PCR). Five single-stranded DNA fragments were synthesized by Invitrogen and were used as primers, the sequences of which were as follows:

Primer 1:
SEQ ID NO: 45
5' GTGCGGGGAACGAGGCTTCTTCTACACACCCAAGACCAAGCGTG

GCATTG 3'

Primer 2:
SEQ ID NO: 46
5' GTAGAGGGAGCAGATGCTGGTACAGCATTGTTCCACAATGCCAC

GCTTGG 3'

Primer 3:
SEQ ID NO: 47
5' TGCGGCTCACACCTGGTGGAAGCTCTCTACCTAGTGTGCGGGGA

ACGAGG 3'

Primer 4:
SEQ ID NO: 48
5' CTGACTGAATTCTAGTTGCAGTAGTTCTCCAGCTGGTAGAGGGA

GCAGAT 3'

Primer 5:
SEQ ID NO: 49
5' ACTTGCTCGAGAAAAGATTTGTGAACCAACACCTGTGCGGCTCA

CACCTG 3'.

The first round of PCR was performed by using a KOD Synthesis Kit (TOYOBO, Cat KOD-201) 50 μL system: 5 μL 10×KOD buffer, 2 μL 2 mM dNTPs, 1.5 μL primer 1 (10 μM), 1.5 μL primer 2 (10 μM), 0.5 μL KOD plus, 2 μL 25 mM MgSO$_4$, and 38 μL ddH$_2$O. The amplification program was 94° C. 2 min; then 94° C. 30 sec, 55° C. 30 sec, 68° C. 30 sec, for 25 amplification cycles, followed by incubation at 68° C. for 2 min. A PCR product having 85 nucleotides was synthesized, then identified on a 1.2% agarose gel and recovered.

The second round of PCR was performed using a 50 μL PCR reaction: 5 μL 10×KOD buffer, 2 μL 2 mM dNTPs, 1 μL product 1, 1.5 μL primer 3 (10 μM), 1.5 μL primer 4 (10 μM), 0.5 μL KOD plus, 2 μL 25 mM MgSO$_4$, and 37 μL ddH$_2$O. The amplification program was 94° C. 2 min; then 94° C. 30 sec, 55° C. 30 sec, 68° C. 30 sec, for 25 amplification cycles, followed by incubation at 68° C. for 2 min. The obtained PCR product 2 having 155 nucleotides was identified on a 1.2% agarose gel and recovered.

The third round of PCR was performed in a 50 μL PCR reaction: 5 μL 10×KOD buffer, 2 μL 2 mM dNTPs, 1 μL product 2, 1.5 μL primer 4 (10 μM), 1.5 μL primer 5 (10 μM), 0.5 μL KOD plus, 2 μL 25 mM MgSO$_4$, and 37 μL ddH$_2$O. The program for the synthesis was 94° C. 2 min; then 94° C. 30 sec, 55° C. 30 sec, 68° C. 30 sec, for 25 amplification cycles, followed by incubation at 68° C. for 2 min. Product 3 was identified on a 1.2% agarose gel and recovered.

Product 3 was ligated into T vector by T vector kit (Takara, Cat. D103A), and then was double digested by EcoR I/Xho I (New England Biolabs, Cat. R0101S/R0146V). The obtained fragment was recovered on a 1.2% agarose gel, and then was ligated into the pPIC9K expression vector (Invitrogen, Cat. K1750-01) using T4 ligase (New England Biolabs, Cat. M0202S). The structure is shown in FIG. 1.

Sequence analysis of the resulting recombinant expression vector was conducted by Invitrogen. The product 3 was verified as a DNA fragment encoding the human insulin B (1-30), A (1-21) precursor, and the sequence is as follows:

SEQ ID NO: 32
TTTGTGAACCAACACCTGTGCGGCTCACACCTGGTGGAAGCTCTC

TACCTAGTGTGCGGGGAACGAGGCTTCTTCTACACACCCAAGACC

AAGCGTGGCATTGTGGAACAATGCTGTACCAGCATCTGCTCCCTC

TACCAGCTGGAGAACTACTGCAACTAG.

2. Transformation of the Expression Vector Comprising the Recombinant Human Insulin B (1-30), A (1-21) Precursor:

5-10 μg of expression vector comprising recombinant human insulin precursor obtained from the above steps were linearized with SalI (Takata, Cat. D1080a), then ⅒th volume of 3M sodium acetate and 2 volumes of anhydrous ethanol were added. After thoroughly mixing, the mixture was placed at −20° C. for 2 hrs. The mixture was centrifuged at high speed (13,000 rpm) for 5 min, the supernatant removed, and the pellet washed twice with 75% ethanol. The pellet was dried upside down, and dissolved with 10 μL ddH2O. 80 μL linearized plasmid and competent cells (*Pichia pastoris* GS115. Invitrogen, Cat. K1750-01) were added to an Electroporation Cuvette (Bio Rad, Cat. 1652086) on ice for 5 min. The parameters of the Electroporator (Bio Rad Micropulser) were set to 2 kV, 25Ω, and 200 uF. Electroporation was conducted. Then 1 mL cooled D-Sorbitol (Biological Engineering Co., Ltd.) was added quickly and mixed up, 100-300 μL mixture was plated on a MD culture plate, and cultured at 30° C. for 3 days until colonies were formed.

3. Screening Clones of Recombinant Human Insulin Precursor by Using G418:

Colonies on the MD culture plate were eluted with 3 mL YPD broth, resuspended, and the concentration of resuspended cells (1 OD$_{600}$=5×10$^7$ cells/mL) was measured with a spectrophotometer (Beckman, DU800). 1×10$^5$ cells were plated on YPD culture plates with various concentrations of G418 (GIBCO, Cat. 11811-031) (0.25. 0.5. 1.0, 2.0, or 4.0 mg/mL), and cultured at 30° C. for 5 days until colonies were formed. 30 single-clones were selected from the five plates with different G418 concentrations, and verified by PCR of recombinant fragments (Polymerase chain reaction).

4. Identification of Clones with Inserted Recombinant Human Insulin B(1-30), A(1-21) Precursor by PCR:

Fragments inserted into G418-resistant colonies were verified by PCR. 18 μL broth were placed in 1.5 mL tubes, and 2 μL cytase (5 U/μL) (Sigma, Cat. L2524) were added and incubated at 30° C. for 10 min. The sample was then placed at −80° C. for 10 min to complete lysis. The identification was performed by using a KOD kit (TOYOBO, Cat KOD-201.) 25 μL PCR system: 2.5 μL 10× reaction buffer, 1.5 μL 25 mM $MgCl_2$, 2.5 μL 2 mM dNTPs, 1 μL 5'AOX1 primer (10 pmol/μL), 1 μL 3'AOX1 primer (10 pmol/μL), 0.5 μL KOD polymerase, 15 μL dd$H_2$O, and 1 μL lysate buffer. The mixture was placed in a PCR instrument system (Eppendorf, 22331 type), and the amplification program was, 94° C. 30 sec, 55° C. 30 sec, 68° C. 4 min, for 25 amplification cycles, followed by incubation at 68° C. for 10 min. 10 μL of PCR products were identified on a 1.0% agarose gel (Sigma, A9539). The results are shown in FIG. 2, with two distinct amplified bands obviously observed. The larger band of 2.2 Kb corresponds to the AOX gene carried by GS115 per se, and the smaller one of 635 bp corresponds to the inserted foreign gene. Lane 6 of FIG. 2 corresponds to clone No. 1001-17. Clone no 1001-17 was chosen for further use.

5. Expression and Characterization of the Recombinant Human Insulin B (1-30), a (1-21) Precursor:

The single colony of Clone 1001-17 was cultured in 50 mL BMGY medium at 30° C., 250 rpm overnight. On the next day, the OD600 value detected should be between 2-6. At room temperature, the culture was centrifuged (Beckman Coulter) at low speed (1,500 g) for 5 min, and the cells were collected and resuspended in BMMY medium to an OD600 of 1.0. 1/200th of the total volume of 100% methanol was added to the medium with a final concentration of 0.5%. The medium was then cultured at 28° C., 250 rpm for 72 hr, and during the period of culture, 1/200th of the total volume of 100% methanol was added every 24 hr. After induction, the medium was centrifuged at low speed (1,500 g) and the supernatant was collected. The expression of Clone 1001-17 precursor protein was verified by SDS-PAGE (Invitrogen, Cat. No. 456-1083). The clone No. 1001-17 was selected for the next fermentation.

Step 2:

Fermentation of Recombinant Human Insulin B (1-30), A (1-21) Precursor

1. Strain: expression strain No. 1001-17.
2. Operation process for 5 L fermentor:
2.1 Activation and Culture of the Strain:

1 mL Glycerol Stock of the strain was inoculated in 100 mL BMGY medium, at 30° C., 220 r/min (rpm) for 20 hrs.

2.2 Inoculation:

Inoculum size was 5%, and 0.4% sterilized PTM1 solution was added. Fermentation was started.

2.3 the Initial Fermentation Stage:

After a period of adaptive phase (10-12 hr), strain fermentation enters into the exponential growth phase. Agitation speed and aeration were continuously increased to meet the requirement of DO>30% for cell growth. Agitation speed was increased by 50-100 rpm every time. 25% industrial ammonia was added via automatically feeding to fix pH to setting value.

2.4 Growth Phase in Glycerol Feeding:

When substrate in initial medium was consumed (18-24 hrs), 50% glycerol was added via feed-batch, at a restrictive rate.

2.5 Methanol Induction Phase:

After 4 to 6 hrs of glycerol transient cell growth phase, glycerol feeding was stopped. Starvation was maintained for 30 min to consume the rest of the glycerol completely. Then methanol was added to start induction. After 96 hrs, the fermentation was stopped.

Step 3:

Isolation and Purification of Fermentation Product

The obtained fermentation broth was ultrafiltrated conventionally, and purified by SP Sepharose FF (GE, cat. 17-0729-10) and Q Sepharose FF (GE, cat. 17-0510-10) column. The purified product was analyzed by HPLC (Waters e2695-2489 liquid meter, Column: phenomenex, Jupiter, C18, 250×4.6 mm, 5 nm, 300 Å), and the purity was greater than 90% purity. The sequence of the resulting expression precursor is as follows:

```
                                            SEQ ID NO: 22
FVNQHLCGSHLVEALYLVCGERGFFYTPKTKRGIVEQCCTSICSL

YQLENYCN
```

The molecular weight of the obtained product detected by LC-MS (liquid MS) is 6074, which is consistent with the theoretically predicted molecular weight of 6074.

Step 4:

Digestion and Purification of Fermentation Product

The above purified product was adjusted to pH9.0 with 50 mM Tris, digested by trypsin (sigma, Cat. T1426) and CPB (Sigma, C9584). The reaction process was analyzed by HPLC. After complete digestion, the pH value was adjusted to 2 with 1M HCL and the reaction was terminated. Two insulin products were prepared by reverse phase (Jupiter C4, 10 μm, 300 Å, 50×250 mm) as follows:

Product 1: recombinant human insulin B (1-30), A (1-21) (referred to as hI):

```
                                           SEQ ID NO: 5
        FVNQHLCGSHLVEALYLVCGERGFFYTPKT,

SEQ ID NO: 1
        GIVEQCCTSICSLYQLENYCN
```

The molecular weight of the obtained product detected by LC-MS was 5807, which is consistent with the theoretically predicted molecular weight of 5807.7.

Product 2: recombinant human insulin B (1-29), R-A (1-21):

```
                                          SEQ ID NO: 78
          FVNQHLCGSHLVEALYLVCGERGFFYTPK

SEQ ID NO: 4
              RGIVEQCCTSICSLYQLENYCN
```

The molecular weight of the obtained product detected by LC-MS was 5863, which is consistent with the theoretically predicted molecular weight of 5862.7.

Step 5:

Analysis of Disulfide Bond Structure in the Cleaved Products

The above-prepared product 1 and product 2 were digested with GluC (Sigma, P6181) at 37° C. for 4 hrs. 2 μl of 1M HCl was added to terminate the reaction. Product was analyzed by LC-MS. The results were as follows:

Analysis of disulfide bond structure in Human insulin B (1-30), A (1-21):

| Fragment No. | Peptide sequence | LC-MS Mol. wt. | Theoretical Mol. wt. |
|---|---|---|---|
| I | GIVE | 416 | 416.47 |
| II | QCCTSICSLYQLE FVNQHLCGSHLVE | 2969 | 2969.39 |
| III | NYCN ALYLVCGE | 1377 | 1377.55 |
| IV | RGFFYTPKT | 1116 | 1116.28 |

The above results confirmed that in recombinant human insulin B (1-30), A (1-21), the configurations of disulfide bonds were as follows: one is formed between A20 and B19; and the other two are formed between any two selected from A6 Cys, A7 Cys, A11 Cys and B7 Cys.

Analysis of disulfide bond structure in Human insulin B (1-29), R-A (1-21)

| Fragment No. | Peptide sequence | LC-MS Mol. wt. | Theoretical Mol. wt. |
|---|---|---|---|
| I | RGIVE | 573 | 572.66 |
| II | QCCTSICSLYQLE FVNQHLCGSHLVE | 2969 | 2969.39 |
| III | NYCN ALYLVCGE | 1377 | 1377.55 |
| IV | RGFFYTPK | 1015 | 1015.18 |

These results confirmed that the configurations of disulfide bonds in recombinant human insulin B (1-29), R-A (1-21) were as follows: one is formed between A20 and B19; and the other two are formed between any two selected from A6 Cys, A7 Cys, A11 Cys and B7 Cys.

Example 2

Preparation of Recombinant Human Insulin B (1-29), A (1-21)

Step 1:

Cloning and Expression of Recombinant Human Insulin B (1-29), A (1-21) Precursor 1. Construction of Expression Vector Comprising Recombinant Human Insulin B (1-29), A (1-21) Precursor:

B (1-29), A (1-21) was obtained via site-directed mutagenesis by using polymerase chain reaction (PCR). Two single-stranded DNA fragments were synthesized by Invitrogen and used as primers for site-directed mutagenesis. The sequences of the primers are as follows:

```
Primer 1:
                                       SEQ ID NO: 50
5' CTTCTACACACCCAAGCGTGGCATTGTGGAAC 3'

Primer 2:
                                       SEQ ID NO: 51
5' GTTCCACAATGCCACGCTTGGGTGTGTAGAAG 3'
```

The recombinant vector finally obtained from Example 1 was used as a template in the procedure of site-directed mutagenesis. KOD kit (TOYOBO, Cat KOD-201.) 254, system was used: 2.5 μL 10×KOD buffer, 2.5 μL 2 mM dNTPs, 1 μL primer 1 (10 μM), 1 μL primer 2 (10 μM), 0.5 μL KOD plus, 1 μL 25 mM MgSO₄, and 16 μL ddH₂O. The amplification program was as follows: 94° C. 2 min; then 94° C. 30 sec, 55° C. 30 sec, 68° C. 11 min, for 25 amplification cycles, followed by incubation for 11 min at 68° C. PCR product was digested for 1 hr by directly adding 1 μL of DpnI (NEB, Cat. R0176L), and was transformed into TOP10 competent cells to obtain the plasmid of interest. The resulting recombinant expression vector was delivered to Invitrogen for sequence analysis.

2. Result of Sequence Analysis:

The ligated recombinant plasmid was analyzed by Invitrogen. The sequences of the obtained DNA encoding the human insulin B (1-29), A (1-21) precursor were as follows:

```
                                       SEQ ID NO: 33
TTTGTGAACCAACACCTGTGCGGCTCACACCTGGTGGAAGCTCTCTAC

CTAGTGTGCGGGGAACGAGGCTTCTTCTACACACCCAAGCGTGGCATT

GTGGAACAATGCTGTACCAGCATCTGCTCCCTCTACCAGCTGGAGAAC

TACTGCAACTAG.
```

3. Transformation of the Expression Vector Comprising Recombinant Human Insulin B(1-29), A(1-21) Precursor Via Electroporation:

The Expression vector comprising recombinant human insulin precursor was transformed as described in Example 1.

4. Screening the Clone of Recombinant Human Insulin B(1-29), A(1-21) Precursor by Using G418:

The clone of recombinant human insulin precursor was screened as described in Example 1.

5. Identification of Clones with Inserted Fragments of Recombinant Human Insulin Precursor by Using PCR:

Inserted fragments of recombinant human insulin precursor were verified as described in Example 1. Clone 006-15 was selected for further use.

6. Expression and Characterization of Recombinant Human Insulin B(1-29), A(1-21) Precursor:

Recombinant human insulin precursor was expressed and identified as described in Example 1. The results showed that clone No. 006-15 expressed the protein of interest, and was selected for the following fermentation.

Step 2:

Fermentation of Recombinant Human Insulin B (1-29), A (1-21) Precursor

Clone No. 006-15 was selected for fermentation. The fermentation method was the same as that described in Example 1.

Step 3:

Isolation and Purification of Fermentation Product

The fermentation product was isolated and purified as described in Example 1. The sequence of the resulting precursor was as follows:

```
                                       SEQ ID NO: 23
FVNQHLCGSHLVEALYLVCGERGFFYTPKRGIVEQCCTSICSLYQ

LENYCN.
```

The molecular weight of the obtained product detected by LC-MS was 5844.7, and the theoretically predicted molecular weight is 5846.2.

Step 4:

Enzymatic Digestion and Purification of Fermentation Product

Method of enzymatic digestion and purification were as described in Example 1. After optimization of the enzymatic reaction system, enzymatically digested products prepared by reverse-phase were as follows:

Recombinant human insulin B (1-29), A (1-21) (referred to as Des (B30)-hI):

SEQ ID NO: 78
FVNQHLCGSHLVEALYLVCGERGFFYTPK,

SEQ ID NO: 1
GIVEQCCTSICSLYQLENYCN.

The molecular weight of the obtained product detected by LC-MS was 5578, which is consistent with the theoretically predicted molecular weight of 5578.

Step 5:

Analysis of Disulfide Bond Structure in the Cleaved Products

The structure of disulfide bonds in cleaved products was analyzed as described in Example 1.

Results from analysis of disulfide bond structure in Human insulin B(1-29), A(1-21) were as follows:

| Fragment No. | Peptide sequence | LC-MS Mol. wt. | Theoretical Mol. wt. |
|---|---|---|---|
| I | GIVE | 417 | 416.47 |
| II | QCCTSICSLYQLE FVNQHLCGSHLVE | 2971 | 2969.39 |
| III | NYCN ALYLVCGE | 1378 | 1377.55 |
| IV | RGFFYTPK | 1015 | 1015 |

These results confirmed that the configurations of disulfide bonds in the recombinant human insulin B (1-29), A (1-21) were as follows: one is formed between A20 and B19; and the other two are formed between any two selected from A6 Cys, A7 Cys, A11 Cys and B7 Cys.

Example 3

Preparation of Recombinant Human Insulin (1-27)-K-E-R, A(1-21)

Step 1:

Cloning and Expression of Recombinant Human Insulin (1-27)-K-E-R, A(1-21) Precursor 1. Construction of Expression Vector Comprising Recombinant Human Insulin (1-27)-K-E-R, A(1-21) Precursor:

B(1-27)-K-E-R, A(1-21) was mutated by using polymerase chain reaction (PCR). Two single-stranded DNA fragments were synthesized by Invitrogen and were used as primers for site-directed mutagenesis. The sequences of the primers are as follows:

Primer 1:
SEQ ID NO: 52
5' GGTTTCTTTTACACCAAGGAAAGAGCTGCTAAAGGTATCGT

TGAGC 3'

Primer 2:
SEQ ID NO: 53
5' GCTCAACGATACCTTTAGCAGCTCTTTCCTTGGTGTAAAAG

AAACC 3'

The recombinant vector finally obtained in Example 1 was used as template in the procedure of site-directed mutagenesis. KOD kit (TOYOBO, Cat KOD-201.) 254, system was used: 2.5 μL 10×KOD buffer, 2.5 μL 2 mM dNTPs, 1 μL primer 1 (10 μM), 1 μL primer 2 (10 μM), 0.5 μL KOD plus, 1 μL 25 mM MgSO$_4$, and 16 μL ddH$_2$O. The amplification program was as follows: 94° C. 2 min; then 94° C. 30 sec, 55° C. 30 sec, 68° C. 11 min, for 25 amplification cycles, followed by incubation for 11 min at 68° C. PCR product was digested for 1 hr by directly adding 1 μL of DpnI (NEB, Cat. R0176L), and then was transformed into TOP10 competent cells to obtain the plasmid of interest. The resulting recombinant expression vector was delivered to Invitrogen for sequence analysis.

2. Result of Sequence Analysis:

The ligated recombinant plasmid was analyzed by Invitrogen. The sequence of the DNA fragment encoding the human insulin B(1-27)-K-E-R, A(1-21) precursor was as follows:

SEQ ID NO: 34
TTCGTCAACCAGCACTTGTGTGGTTCCCATTTGGTTGAGGCTCTGTACT

TGGTCTGTGGAGAAAGAGGTTTCTTTTACACCAAGGAAAGAGCTGCTAA

AGGTATCGTTGAGCAATGTTGCACCTCTATTTGTTCCCTGTATCAGTTG

GAAAACTACTGCAACTAA.

3. Transformation of Expression Vector Comprising Recombinant Human Insulin B(1-27)-K-E-R, A(1-21) Precursor Via Electroporation:

Expression vector comprising recombinant human insulin precursor was transformed as described in Example 1.

4. Screening Clones of Recombinant Human Insulin B(1-27)-K-E-R, A(1-21) Precursor by Using G418:

Clones of recombinant human insulin precursor was screened as described in Example 1.

5. Identification of Clones with Inserted Recombinant Human Insulin Precursor Fragments by PCR:

Inserted fragments of recombinant human insulin precursor clones were verified as described in Example 1. Clone No. 064-6 was selected for further use.

6. Expression and Characterization of Recombinant Human Insulin B(1-27)-K-E-R, A(1-21) Precursor:

The method was the same as that described in Example 1. The results showed that clone No. 064-6 expressed the protein of interest, and was selected for the following fermentation.

Step 2:

Fermentation of Recombinant Human Insulin Precursor

Clone No. 064-6 was selected for fermentation. The fermentation method was as described in Example 1.

Step 3:

Isolation and Purification of Fermentation Product

The fermentation product was isolated and purified as described in Example 1. The sequence of the resulting precursor was as follows:

SEQ ID NO: 24
FVNQHLCGSHLVEALYLVCGERGFFYTKERAAKGIVEQCCTSICSLYQL

ENYCN.

The molecular weight of the obtained product detected by LC-MS was 6147, which is consistent with the theoretically predicted molecular weight of 6147.

Step 4:

Enzymatic Digestion and Purification of Fermentation Product

The above purified product was adjusted to pH 9.0 with 50 mM Tris, and digested by trypsin (sigma, Cat. T1426). The reaction progress was analyzed by HPLC. After complete digestion, the pH value was adjusted to 2 with 1M HCL to terminate the reaction. The digested products prepared by reverse phase (Jupiter C4, 10 µm, 300 Å, 50×250 mm) were as follows:

```
Human insulin B (1-27)-K-E-R, A (1-21):
                                        SEQ ID NO: 6
FVNQHLCGSHLVEALYLVCGERGFFYTKER,

SEQ ID NO: 1
GIVEQCCTSICSLYQLENYCN.
```

The molecular weight of the obtained product detected by LC-MS was 5894, which is consistent with the theoretically predicted molecular weight of 5894.7.

Step 5:
Analysis of Disulfide Bond Structure in Cleaved Products

The structure of disulfide bonds in cleaved products was analyzed as described in Example 1.

Results from analysis of disulfide bond structure in Human insulin B(1-27)-K-E-R, A(1-21) were as follows:

| Fragment No. | Peptide sequence | LC-MS Mol. wt. | Theoretical Mol. wt. |
|---|---|---|---|
| I | GIVE | 417 | 416.47 |
| II | QCCTSICSLYQLE FVNQHLCGSHLVE | 2971 | 2969.39 |
| III | NYCN ALYLVCGE | 1377 | 1377.55 |
| IV | RGFFYTKER | 1203 | 1203.37 |

These results confirmed that the configurations of disulfide bonds in recombinant human insulin B(1-27)-K-E-R, A(1-21) were as follows: one is formed between A20 and B19; and the other two are formed between any two selected from A6 Cys, A7 Cys, A11 Cys and B7 Cys.

Example 4

Preparation of Recombinant Human Insulin B(1-27)-K-E, A(1-21)

Step 1:
Cloning and Expression of Recombinant Human Insulin B(1-27)-K-E, A(1-21) Precursor 1. Construction of Expression Vector Comprising Recombinant Human Insulin Precursor:

B(1-27)-K-E, A(1-21) was obtained by site-directed mutation via polymerase chain reaction (PCR). Two single-stranded DNA fragments were synthesized by Invitrogen and used as primers for site-directed mutagenesis, and the sequences were as follows:

```
Primer 1:
                                        SEQ ID NO: 54
5' GGTTTCTTTTACACCAAGGAAAAAGAGGTATCGTTG 3'

Primer 2:
                                        SEQ ID NO: 55
5' CAACGATACCTCTTTTTTCCTTGGTGTAAAAGAAACC 3'.
```

The recombinant vector finally obtained in Example 1 was used as template in the site-directed mutagenesis procedure. KOD kit (TOYOBO, Cat KOD-201.) 25 µL system was used: 2.5 µL 10×KOD buffer, 2.5 µL 2 mM dNTPs, 1 µL primer 1 (10 µM), 1 µL primer 2 (10 µM), 0.5 µL KOD plus, 1 µL 25 mM MgSO₄, and 16 µL ddH₂O. The amplification program was as follows, 94° C. 2 min; then 94° C. 30 sec, 55° C. 30 sec, 68° C. 11 min, for 25 amplification cycles, followed by incubation for 11 min at 68° C. PCR product was digested for 1 hr by directly adding 1 µL of DpnI (NEB, Cat. R0176L), and then was transformed into TOP10 competent cells to obtain the plasmid of interest. The resulting recombinant expression vector was delivered to Invitrogen for sequence analysis.

2. Result of Sequence Analysis:
The ligated recombinant plasmid was analyzed by Invitrogen. The sequence of DNA encoding the human insulin B(1-27)-K-E, A(1-21) precursor was as follows:

```
                                        SEQ ID NO: 35
TTCGTCAACCAGCACTTGTGTGGTTCCCATTTGGTTGAGGCTCTGTACT

TGGTCTGTGGAGAAAGAGGTTTCTTTTACACCAAGGAAAAAGAGGTAT

CGTTGAGCAATGTTGCACCTCTATTTGTTCCCTGTATCAGTTGGAAAAC

TACTGCAACTAA.
```

3. Transformation of Expression Vector Comprising Recombinant Human Insulin B(1-27)-K-E, A(1-21) Precursor Via Electroporation:

Expression vector comprising recombinant human insulin precursor was transformed as in Example 1.

4. Screening Clones of Recombinant Human Insulin B(1-27)-K-E, A(1-21) Precursor by Using G418:

Recombinant human insulin precursor clones were screened as in Example 1.

5. Identification of Clones with Inserted Recombinant Human Insulin Precursor Fragments by PCR:

Inserted fragments of recombinant human insulin precursor were verified as described in Example 1. Clone No. 062-6 was selected for further use.

6. Expression and Characterization of Recombinant Human Insulin B(1-27)-K-E, A(1-21) Precursor:

Recombinant human insulin precursor was expressed and identified as in Example 1. The results showed that clone mo. 062-6 expressed the protein of interest, and was selected for the following fermentation.

Step 2:
Fermentation of Recombinant Human Insulin Precursor
Clone No. 062-6 was selected for fermentation. The fermentation method was as described in Example 1.

Step 3:
Isolation and Purification of Fermentation Product
The fermentation product was isolated and purified as described in Example 1. The resulting precursor was as follows:

```
                                        SEQ ID NO: 25
FVNQHLCGSHLVEALYLVCGERGFFYTKEKRGIVEQCCTSICSLYQLE

NYCN.
```

The molecular weight of the obtained product detected by LC-MS was 6004.91, which is consistent with the theoretically predicted molecular weight of 6006.3.

Step 4:
Enzymatic Digestion and Purification of Fermentation Product

Method of enzymatic digestion and purification was as described in Example 1. After optimization of the enzymatic reaction system, digested products prepared by reverse-phase were as follows:

```
Human insulin B(1-27)-K-E, A(1-21):
                                  SEQ ID NO: 7
FVNQHLCGSHLVEALYLVCGERGFFYTKE

SEQ ID NO: 1
GIVEQCCTSICSLYQLENYCN.
```

The molecular weight of the obtained product detected by LC-MS was 5738.54, which is consistent with the theoretically predicted molecular weight of 5738.8.

Step 5:

Analysis of Disulfide Bond Structure in Cleaved Products

The structure of disulfide bonds in cleaved products was analyzed as described in Example 1.

Results from analysis of Disulfide bond structure Human insulin B(1-27)-K-E, A(1-21) were as follows:

| Fragment No. | Peptide sequence | LC-MS Mol. wt. | Theoretical Mol. wt. |
|---|---|---|---|
| I | GIVE | 417 | 416.47 |
| II | QCCTSICSLYQLE FVNQHLCGSHLVE | 2968.8 | 2969.39 |
| III | NYCN ALYLVCGE | 1377.7 | 1377.55 |
| IV | RGFFYTKE | 1047.6 | 1047.18 |

These results confirmed that the configurations of the disulfide bonds of recombinant human insulin B(1-27)-K-E, A(1-21) were as follows: one is formed between A20 and B19; the other two are formed between any two selected from A6 Cys, A7 Cys, A11 Cys and B7 Cys.

Example 5

Preparation of Recombinant Human Insulin B(1-27)-K-P-E, A(1-21)

Step 1:

Cloning and Expression of Recombinant Human Insulin B(1-27)-K-P-E, A(1-21) Precursor 1. Construction of the Expression Vector Comprising Recombinant Human Insulin B(1-27)-K-P-E, A(1-21) Precursor:

B(1-27)-K-P-E, A(1-21) was mutated via polymerase chain reaction (PCR). Two single-stranded DNA fragments were synthesized by Invitrogen and used as primers for site-directed mutagenesis. The sequences of the primers were as follows:

```
Primer 1:
                                  SEQ ID NO: 56
5' GGTTTCTTTTACACCAAGCCTGAAAAAGAGGTATCGTTG 3'

Primer 2:
                                  SEQ ID NO: 57
5' CAACGATACCTCTTTTTTCAGGCTTGGTGTAAAAGAAACC 3'.
```

The recombinant vector finally obtained in Example 1 was used as template in the site-directed mutagenesis procedure. KOD kit (TOYOBO, Cat KOD-201.) 25 µL system was used: 2.5 µL 10×KOD buffer, 2.5 µL 2 mM dNTPs, 1 µL primer 1 (10 µM), 1 µL primer 2 (10 µM), 0.5 µL KOD plus, 1 µL 25 mM MgSO$_4$, and 16 µL ddH$_2$O. The amplification program was as follows, 94° C. 2 min; then 94° C. 30 sec, 55° C. 30 sec, 68° C. 11 min, for 25 amplification cycles, followed by incubation for 11 min at 68° C. PCR product was digested for 1 hr by directly adding 1 µL of DpnI (NEB, Cat. R0176L), then was transformed into TOP10 competent cells to obtain the plasmid or interest. The resulting recombinant expression vector was delivered to Invitrogen for sequence analysis.

2. Result of Sequence Analysis:

The ligated recombinant plasmid was analyzed by Invitrogen. Sequence of the obtained DNA encoding the human insulin B(1-27)-K-P-E, A(1-21) precursor was as follows:

```
                                  SEQ ID NO: 36
TTCGTCAACCAGCACTTGTGTGGTTCCCATTTGGTTGAGGCTCTGTACT

TGGTCTGTGGAGAAAGAGGTTTCTTTTACACCAAGCCTGAAAAAGAGG

TATCGTTGAGCAATGTTGCACCTCTATTTGTTCCCTGTATCAGTTGGAA

AACTACTGCAACTAA.
```

3. Transformation of Expression Vector Comprising Recombinant Human Insulin B(1-27)-K-P-E, A(1-21) Precursor Via Electroporation:

Expression vector comprising recombinant human insulin precursor was transformed as in Example 1.

4. Screening Clones of Recombinant Human Insulin B(1-27)-K-P-E, A(1-21) Precursor by Using G418:

Recombinant human insulin precursor clone was screened as in Example 1.

5. Inserted Fragments for Recombinant Human Insulin Precursor Clone Verified by PCR:

Inserted fragments of recombinant human insulin precursor clone were verified as in Example 1. Clone No. 061-5 was selected for further use.

6. Expression and Characterization of Recombinant Human Insulin B(1-27)-K-P-E, A(1-21) Precursor:

Recombinant human insulin precursor was expressed and identified as in Example 1. The results showed that clone No. 061-5 expressed the protein of interest, and was selected for the following fermentation.

Step 2:

Fermentation of Recombinant Human Insulin B(1-27)-K-P-E, A(1-21) Precursor

Clone No. 061-5 was selected for fermentation. The fermentation method was as described in Example 1.

Step 3:

Isolation and Purification of Fermentation Product

The fermentation product was isolated and purified as described in Example 1. The resulting expression product precursor was as follows:

```
                                  SEQ ID NO: 26
FVNQHLCGSHLVEALYLVCGERGFFYTKPEKRGIVEQCC

TSICSLYQLENYCN.
```

The molecular weight of the obtained product detected by LC-MS was 6102, which is consistent with the theoretically predicted molecular weight of 6102.

Step 4:

Enzymatic Digestion and Purification of Fermentation Product

Method of enzymatic digestion and purification is the same as described in Example 1. After optimization of the enzymatic reaction system, digested products prepared by reverse-phase were as follows:

```
Human insulin B(1-27)-K-P-E, A(1-21):
                                    SEQ ID NO: 8
FVNQHLCGSHLVEALYLVCGERGFFYTKPE,

SEQ ID NO: 1
GIVEQCCTSICSLYQLENYCN.
```

The molecular weight of the obtained product detected by LC-MS was 5835, which is consistent with the theoretically predicted molecular weight of 5835.7.

Step 5:
Analysis of Disulfide Bond Structure in Cleaved Products
The structure of disulfide bonds in cleaved products was analyzed as described in Example 1.
Results obtained from analysis of disulfide bond structure in Human insulin B(1-27)-K-P-E, A(1-21) were as follows:

| Fragment No. | Peptide sequence | LC-MS Mol. wt. | Theoretical Mol. wt. |
|---|---|---|---|
| I | GIVE | 416 | 416.47 |
| II | QCCTSICSLYQLE FVNQHLCGSHLVE | 2969 | 2969.39 |
| III | NYCN ALYLVCGE | 1376.8 | 1377.55 |
| IV | RGFFYTKPE | 1143.6 | 1143.28 |

These results confirmed that the configurations of the disulfide bonds of recombinant human insulin B(1-27)-K-P-E, A(1-21) were as follows: one is formed between A20 and B19; and the other two are formed between any two selected from A6 Cys, A7 Cys, A11 Cys and B7 Cys.

Example 6

Preparation of Recombinant Human Insulin B(1-2)-K-B(4-28)-E-E, A(1-21)

Step 1:
Coning and Expression of Recombinant Human Insulin B(1-2)-K-B(4-28)-E-E, A(1-21) Precursor
1. Construction of the Expression Vector Comprising Recombinant Human Insulin Precursor:
B(1-2)-K-B(4-28)-E-E, A(1-21) was mutated via site-directed mutagenesis by polymerase chain reaction (PCR). Single-stranded DNA fragments were synthesized by Invitrogen and used as primers for site-directed mutagenesis. The sequences of the primers were as follows:

```
Primer 1:
                                    SEQ ID NO: 58
5' GAGAAAAGATTCGTCAAGCAGCACTTGTGTGG 3'

Primer 2:
                                    SEQ ID NO: 59
5' CCACACAAGTGCTGCTTGACGAATCTTTTCTC 3'

Primer 3:
                                    SEQ ID NO: 60
5' GTTTCTTTTACACCCCTGAAGAAAAAGAGGTATCGTTG 3'

Primer 4:
                                    SEQ ID NO: 61
5' CAACGATACCTCTTTTTTCTTCAGGGGTGTAAAAGAAAC 3'.
```

The recombinant vector finally obtained in Example 1 was used as template in the site-directed mutagenesis procedure. KOD kit (TOYOBO, Cat KOD-201.) 25 μL system was used: 2.5 μL 10×KOD buffer, 2.5 μL 2 mM dNTPs, 1 μL primer 1 (10 μM), primer 2 (10 μM), 0.5 μL KOD plus, 1 μL 25 mM MgSO$_4$, and 16 μL ddH$_2$O. The amplification program was as follows: 94° C. 2 min; then 94° C. 30 sec, 55° C. 30 sec, 68° C. 11 min, for 25 cycles, followed by incubation for 11 min at 68° C. PCR product was digested for 1 hr by directly adding 1 μL of DpnI (NEB, Cat. R0176L), then was transformed into TOP10 competent cells to obtain the plasmid of interest. The resulting recombinant expression vector was delivered to Invitrogen for sequence analysis.

2. Result of Sequence Analysis.
The linked recombinant plasmid was analyzed by Invitrogen. Sequence of the obtained DNA encoding the human insulin B(1-2)-K-B(4-28)-E-E, A(1-21) precursor was as follows:

```
                                    SEQ ID NO: 37
TTCGTCAAGCAGCACTTGTGTGGTTCCCATTTGGT

TGAGGCTCTGTACTTGGTCTGTGGAGAAAGAGGTT

TCTTTTACACCCCTGAAGAAAAAGAGGTATCGTT

GAGCAATGTTGCACCTCTATTTGTTCCCTGTATCA

GTTGGAAAACTACTGCAACTAA.
```

3. Transformation for Expression Vector Comprising Recombinant Human Insulin B(1-2)-K-B(4-28)-E-E, A(1-21) Precursor Via Electroporation:
Expression vector comprising recombinant human insulin precursor was transformed as in Example 1.
4. Screening Clones of Recombinant Human Insulin B(1-2)-K-B(4-28)-E-E, A(1-21) Precursor by Using G418:
Recombinant human insulin precursor clones was screened as in Example 1.
5. Identification of Clones with Inserted Recombinant Human Insulin Precursor Fragment by PCR:
Inserted fragments of recombinant human insulin precursor were verified as in Example 1. Clone No. 070-4 was selected for further use.
6. Expression and Characterization of Recombinant Human Insulin B(1-2)-K-B(4-28)-E-E, A(1-21) Precursor:
Recombinant human insulin precursor was expressed and identified as in Example 1. The results showed that clone No. 070-4 expressed the protein of interest, and was selected for the following fermentation.
Step 2:
Fermentation of Recombinant Human Insulin B(1-2)-K-B(4-28)-E-E, A(1-21) Precursor
Clone No. 070-4 was selected for fermentation. The fermentation method was as described in Example 1.
Step 3:
Isolation and Purification of Fermentation Product
The fermentation product was isolated and purified as described in Example 1. The sequence of the resulting expression product precursor was as follows:

```
                                    SEQ ID NO: 21
FVKQHLCGSHLVEALYLVCGERGFFYTPEEKRGIV

EQCCTSICSLYQLENYCN.
```

The molecular weight of the obtained product detected by LC-MS was 6117, which is consistent with the theoretically predicted molecular weight of 6117.

Step 4:

Enzymatic Digestion and Purification of Fermentation Product

Method of Enzymatic digestion and purification was as described in Example 1. After optimization of the enzymatic reaction system, digested products prepared by reverse-phase were as follows:

```
Human insulin B(1-2)-K-B(4-28)-E-E, A(1-21):
                                       SEQ ID NO: 9
FVKQHLCGSHLVEALYLVCGERGFFYTPEE,

SEQ ID NO: 1
GIVEQCCTSICSLYQLENYCN.
```

The molecular weight of the obtained product detected by LC-MS was 5850, which is consistent with the theoretically predicted molecular weight of 5850.7.

Step 5:

Analysis of Disulfide Bond Structure in Cleaved Products

Structure of disulfide bond in cleaved products was analyzed as described in Example 1.

Results obtained from analysis of disulfide bond structure in Human insulin B(1-2)-K-B(4-28)-E-E, A(1-21) were as follows:

| Fragment No. | Peptide sequence | LC-MS Mol. wt. | Theoretical Mol. wt. |
|---|---|---|---|
| I | GIVE | 417 | 416.47 |
| II | QCCTSICSLYQLE FVKQHLCGSHLVE | 2982.8 | 2983.46 |
| III | NYCN ALYLVCGE | 1376.5 | 1377.55 |
| IV | RGFFYTPEE | 1145.5 | 1144.3 |

These results confirmed the configurations of the disulfide bonds of recombinant human insulin B(1-2)-K-B(4-28)-E-E, A(1-21) were as follows: one is formed between A20 and B19; and the other two are formed between any two selected from A6 Cys, A7 Cys, A11 Cys and B7 Cys.

Example 7

Preparation of Recombinant Human Insulin B(1-27)-D-K-E, A(1-21) and B(1-27)-D-K-E, A(1-20)-G Part I: Cloning and Expression of Recombinant Human Insulin B(1-27)-D-K-E, A(1-21)

Step 1.

Construction of the Expression Vector Comprising Recombinant Human Insulin Precursor:

B(1-27)-D-K-E, A(1-21) was mutated via site-directed mutagenesis by using polymerase chain reaction (PCR). Single-stranded DNA fragments were synthesized by Invitrogen and used as primers for site-directed mutagenesis. The sequences of the primers were as follows:

```
Primer 1:
                                        SEQ ID NO: 62
5' GGTTTCTTTTACACCGATAAGGAAAAAGAGGTATCGTTG 3'

Primer 2:
                                        SEQ ID NO: 63
5' CAACGATACCTCTTTTTTCCTTATCGGTGTAAAAGAAACC 3'.
```

The recombinant vector finally obtained in Example 1 was used as template in the site-directed mutagenesis procedure. KOD kit (TOYOBO, Cat KOD-201.) 25 μL system was used: 2.5 μL 10×KOD buffer, 2.5 μL 2 mM dNTPs, 1 μL primer 1 (10 μM), 1 μL primer 2 (10 μM), 0.5 μL KOD plus, 1 μL 25 mM MgSO$_4$, and 16 μL ddH$_2$O. The amplification program was as follows: 94° C. 2 min; then 94° C. 30 sec, 55° C. 30 sec, 68° C. 11 min, for 25 amplification cycles, followed by incubation for 11 min at 68° C. PCR product was digested for 1 hr by directly adding 1 μL of DpnI (NEB, Cat. R0176L), then was transformed into TOP10 competent cells to obtain the plasmid of interest. The resulting recombinant expression vector was delivered to Invitrogen for sequence analysis.

2. Result of Sequence Analysis.

The ligated recombinant plasmid was analyzed by Invitrogen. The sequence of the obtained DNA encoding the human insulin B(1-27)-D-K-E, A(1-21) precursor was as follows:

```
                                        SEQ ID NO: 38
TTCGTCAACCAGCACTTGTGTGGTTCCCATTTGGTTGA

GGCTCTGTACTTGGTCTGTGGAGAAAGAGGTTTCTTTT

ACACCGATAAGGAAAAAGAGGTATCGTTGAGCAATGT

TGCACCTCTATTTGTTCCCTGTATCAGTTGGAAAACTA

CTGCAACTAA.
```

3. Transformation of Expression Vector Comprising Recombinant Human Insulin B(1-27)-D-K-E, A(1-21) Precursor Via Electroporation:

Expression vector comprising recombinant human insulin precursor B(1-27)-D-K-E, A(1-21) was transformed as in Example 1.

4. Screening Clones of Recombinant Human Insulin B(1-27)-D-K-E, A(1-21) Precursor by Using G418:

Recombinant human insulin precursor clones were screened as in Example 1.

5. Identification of Clones with Inserted Recombinant Human Insulin Precursor by PCR:

Inserted fragments of recombinant human insulin precursor clone were verified as in Example 1. Clone No. 068-4 was selected for further use.

6. Expression and Characterization of Recombinant Human Insulin B(1-27)-D-K-E, A(1-21) Precursor:

Recombinant human insulin precursor was expressed and identified as in Example 1. The results showed that clone No. 068-4 expressed the protein of interest, and was selected for the following fermentation.

Step 2:

Fermentation of Recombinant Human Insulin B(1-27)-D-K-E, A(1-21) Precursor

Clone No. 068-4 was selected for fermentation. The fermentation method was as described in Example 1.

Step 3:

Isolation and Purification of Fermentation Product

The fermentation product was isolated and purificated as described in Example 1. The resulting expression product precursor was as follows:

```
                                        SEQ ID NO: 19
FVNQHLCGSHLVEALYLVCGERGFFYTDKEKRGIVE

QCCTSICSLYQLENYCN.
```

The molecular weight of the obtained product detected by LC-MS was 6119.99, which is consistent with the theoretically predicted molecular weight of 6119.5.

Step 4:

Enzymatic Digestion and Purification of Fermentation Product

Methods of enzymatic digestion and purification were as described in Example 1. After optimization of the enzymatic reaction system, digested products prepared by reverse-phase were as follows:

```
Human insulin B(1-27)-D-K-E, A(1-21):
                                    SEQ ID NO: 10
FVNQHLCGSHLVEALYLVCGERGFFYTDKE,

SEQ ID NO: 1
GIVEQCCTSICSLYQLENYCN.
```

The molecular weight of the obtained product detected by LC-MS was 5853.6. which is consistent with the theoretically predicted molecular weight of 5853.

Step 5:

Analysis of Disulfide Bond Structure in Cleaved Products

The structure of disulfide bonds in cleaved products were analyzed as described in Example 1.

Results obtained from analysis of disulfide bond structure in Human insulin B(1-27)-D-K-E, A(1-21) were as follows:

| Fragment NO | Peptide sequence | LC-MS Mol. wt. | Theoretical Mol. wt. |
|---|---|---|---|
| I | GIVE | 417.2 | 416.47 |
| II | QCCTSICSLYQLE FVNQHLCGSHLVE | 2968.8 | 2969.39 |
| III | NYCN ALYLVCGE | 1378.3 | 1377.55 |
| IV | RGFFYTDKE | 1162.6 | 1162.27 |

These results confirmed that the configurations of the disulfide bonds of recombinant human insulin B(1-27)-D-K-E, A(1-21) were as follows: one is formed between A20 and B19; and the other two are formed between any two selected from A6 Cys, A7 Cys, A11 Cys and B7 Cys.

Part II: Preparation of Recombinant Human Insulin B (1-27)-D-K-E, A (1-20)-G

Steps 1 to 3 of the preparation of recombinant human insulin B (1-27)-D-K-E, A (1-21) were repeated, except that the primer and the template used were as follows:

1. The primers for site-directed mutagenesis in Step 1 have the sequences as follows:

```
Primer 1:
                                    SEQ ID NO: 66
5' GTTGGAAAACTACTGCGGTTAAGAATTCCCTAGG 3'

Primer 2:
                                    SEQ ID NO: 67
5' CCTAGGGAATTCTTAACCGCAGTAGTTTTCCAAC 3'.
```

Recombinant vector comprising B(1-27)-D-K-E, A(1-21) (SEQ ID NO: 38) was the template in site-directed mutagenesis procedure.

2. Clone No. 115-1 was selected for fermentation. The fermentation method was as described in Example 1.

3. The fermentation product was isolated and purified as described in Example 1.

The resulting expression product precursor was as follows:

```
                                    SEQ ID NO: 77
FVNQHLCGSHLVEALYLVCGERGFFYTDKEKRGI

VEQCCTSICSLYQLENYCG.
```

4. Methods of enzymatic digestion and purification were as described in Example 1. After optimization of the enzymatic reaction system, digested products prepared by reverse-phase were as follows:

```
Human insulin B(1-27)-D-K-E, A(1-20)-G:
                                    SEQ ID NO: 10
FVNQHLCGSHLVEALYLVCGERGFFYTDKE,

SEQ ID NO: 2
GIVEQCCTSICSLYQLENYCG.
```

5. The structure of disulfide bonds in cleaved products was analyzed as described in Example 1. The results confirmed that the product obtained in the example has the correct configuration.

Example 8

Preparation of Recombinant Human Insulin B(1-2)-D-B(4-30)-R-R, A(1-20)-G and B(1-2)-D-B(4-30)-R, R-A(1-20)-G Step 1:

Cloning and Expression of Recombinant Human Insulin B(1-2)-D-B(4-30)-R-R, A(1-20)-G and B(1-2)-D-B(4-30)-R, R-A(1-20)-G Precursors 1. Construction of the Expression Vector Comprising Recombinant Human Insulin Precursors:

B(1-2)-D-B(4-30)-R-R, A(1-20)-G and B(1-2)-D-B(4-30)-R, R-A(1-20)-G precursors were mutated via site-directed mutagenesis by using polymerase chain reaction (PCR). Four single-stranded DNA fragments were synthesized by Invitrogen and used as primers for site-directed mutagenesis. The sequences of the primers were as follows:

```
Primer 1:
                                    SEQ ID NO: 64
5' GGTTTCTTTTACACCCCTAAGACTAGAAGAGGTATCGTTGAG 3'

Primer 2:
                                    SEQ ID NO: 65
5' CTCAACGATACCTCTTCTAGTCTTAGGGGTGTAAAAGAAACC 3'

Primer 3:
                                    SEQ ID NO: 66
5' GTTGGAAAACTACTGCGGTTAAGAATTCCCTAGG 3'

Primer 4:
                                    SEQ ID NO: 67
5' CCTAGGGAATTCTTAACCGCAGTAGTTTTCCAAC 3'.
```

KOD kit (TOYOBO, Cat KOD-201.) 25 µL system was used in the site-directed mutagenesis procedure: 2.5 µL 10×KOD buffer, 2.5 µL 2 mM dNTPs, 1 µL primer 1 (10 µM), 1 µL primer 2 (10 µM), 0.5 µL KOD plus, 1 µL 25 mM MgSO$_4$, and 16 µL ddH$_2$O. The amplification program was as follows: 94° C. 2 min; then 94° C. 30 sec, 55° C. 30 sec, 68° C. 11 min, for 25 amplification cycles, followed by incubation for 11 min at 68° C. PCR product was digested for 1 hr by directly adding 1 µL of DpnI (NEB, Cat. R0176L), then was transformed into TOP10 competent cells to obtain the plasmid of interest. The resulting recombinant expression vector was delivered to Invitrogen for sequence analysis.

2. Results of Sequence Analysis.

The ligated recombinant plasmids were analyzed by Invitrogen. The sequences of the obtained DNA fragments encoding the human insulin B(1-2)-D-B(4-30)-R-R, A(1-20)-G and B(1-2)-D-B(4-30)-R, R-A(1-20)-G precursors were as follows:

SEQ ID NO: 39
TTCGTCGATCAGCACTTGTGTGGTTCCCATTTGGTTGAGGCTCTGTACTT

GGTCTGTGGAGAAAGAGGTTTCTTTTACACCCCTAAGACTAGAAGAGGTA

TCGTTGAGCAATGTTGCACCTCTATTTGTTCCCTGTATCAGTTGGAAAAC

TACTGCGGTTAA.

3. Transformation of Expression Vector Comprising Recombinant Human Insulin B(1-2)-D-B(4-30)-R-R, A(1-20)-G and B(1-2)-D-B(4-30)-R, R-A(1-20)-G Precursors via electroporation:

Expression vector comprising recombinant human insulin precursor was transformed as in Example 1.

4. Screening Clones of Recombinant Human Insulin B(1-2)-D-B(4-30)-R-R, A(1-20)-G and B(1-2)-D-B(4-30)-R, R-A(1-20)-G Precursors by Using G418:

Clones of recombinant human insulin precursors were screened as in Example 1.

5. Identification of Clones with Inserted Fragments of Recombinant Human Insulin Precursor by PCR:

Inserted fragments of recombinant human insulin precursor were verified as in Example 1. Clone No. 073-16 was selected for further use.

6. Expression and Characterization of Recombinant Human Insulin B(1-2)-D-B(4-30)-R-R, A(1-20)-G and B(1-2)-D-B(4-30)-R, R-A(1-20)-G Precursors:

Recombinant human insulin precursor was expressed and identified as in Example 1. The results showed that clone No. 073-16 expressed the protein of interest, and was selected for the following fermentation.

Step 2:

Fermentation of Recombinant Human Insulin Precursor

Clone No. 073-16 was selected for fermentation. The fermentation method was as described in Example 1.

Step 3:

Isolation and Purification of Fermentation Product

The fermentation product was isolated and purified as described in Example 1. The resulting product was as follows:

SEQ ID NO: 27
FVDQHLCGSHLVEALYLVCGERGFFYTPKTRRGIVEQCCTSICSLYQLEN

YCG.

The molecular weight of the obtained product detected by LC-MS was 6046.3, which is consistent with the theoretically predicted molecular weight of 6045.96.

Step 4:

Enzymatic Digestion and Purification of Fermentation Product

Methods of Enzymatic digestion and purification were as described in Example 3. After optimization of the enzymatic reaction system, digested products prepared by reverse-phase were as follows:

Product 1: human insulin B(1-2)-D-B(4-30)-R-R, A(1-20)-G:

SEQ ID NO: 11
FVDQHLCGSHLVEALYLVCGERGFFYTPKTRR,

SEQ ID NO: 2
GIVEQCCTSICSLYQLENYCG.

The molecular weight of the obtained product detected by LC-MS was 6064.8, which is consistent with the theoretically predicted molecular weight of 6063.96.

Product 2: human insulin B(1-2)-D-B(4-30)-R, R-A(1-20)-G:

SEQ ID NO: 12
FVDQHLCGSHLVEALYLVCGERGFFYTPKTR,

SEQ ID NO: 3
RGIVEQCCTSICSLYQLENYCG.

The molecular weight of the obtained product detected by LC-MS was 6064.8, which is consistent with the theoretically predicted molecular weight of 6063.96.

Step 5:

Analysis of Disulfide Bond Structure in Cleaved Products

The structure of disulfide bonds in cleaved products was analyzed as described in Example 1.

Results obtained from analysis of disulfide bond structure in Human insulin B(1-2)-D-B(4-30)-R-R, A(1-20)-G:

| Fragment NO | Peptide sequence | LC-MS Mol. wt. | Theoretical Mol. wt. |
| --- | --- | --- | --- |
| I | GIVE | 417.2 | 416.47 |
| II | QCCTSICSLYQLE FVNQHLCGSHLVE | 2970.3 | 2969.39 |
| III | NYCG ALYLVCGE | 1377 | 1377.55 |
| IV | RGFFYTPKTRR | 1428.0 | 1428.6 |

These results confirmed that the configurations of the disulfide bonds of recombinant human insulin B(1-2)-D-B(4-30)-R-R, A(1-20)-G were as follows: one is formed between A20 and B19; and the other two are formed between any two selected from A6 Cys, A7 Cys, A11 Cys and B7 Cys.

Results from analysis of Human insulin B (1-2)-D-B (4-30)-R, R-A (1-20)-G disulfide structure:

| Fragment No. | Peptide sequence | LC-MS Mol. wt. | Theoretical Mol. wt. |
| --- | --- | --- | --- |
| I | RGIVE | 573.4 | 572.66 |
| II | QCCTSICSLYQLE FVNQHLCGSHLVE | 2970.3 | 2969.39 |
| III | NYCG ALYLVCGE | 1320.6 | 1320.5 |
| IV | RGFFYTPKTR | 1272.6 | 1272.47 |

These results confirmed that the configurations of the disulfide bonds in recombinant human insulin B(1-2)-D-B(4-30)-R, R-A(1-20)-G were as follows: one is formed between A20 and B19; and the other two are formed between any two selected from A6 Cys, A7 Cys, A11 Cys and B7 Cys.

Example 9

Preparation of Recombinant Human Insulin B(1-2)-K-B(4-28)-E-R-R, A(1-21)

Step 1:
Cloning and Expression of Recombinant Human Insulin B(1-2)-K-B(4-28)-E-R-R, A(1-21) Precursor
1. Construction of the Expression Vector Comprising Recombinant Human Insulin Precursor:

B(1-2)-K-B(4-28)-E-R-R, A(1-21) were mutated via site-directed mutagenesis by using polymerase chain reaction (PCR). Two single-stranded DNA fragments were synthesized by Invitrogen and used as primers for site-directed mutagenesis. The sequences of the primers were as follows:

```
Primer 1:
                                     SEQ ID NO: 68
5' CTTTTACACCCCTGAAAGAAGAGGTATCGTTGAG 3'

Primer 2:
                                     SEQ ID NO: 69
5' CTCAACGATACCTCTTCTTTCAGGGGTGTAAAAG 3'.
```

The recombinant vector finally obtained in Example 6 was used as template in the site-directed mutagenesis procedure. KOD kit (TOYOBO, Cat KOD-201.) 25 μL system was used: 2.5 μL 10×KOD buffer, 2.5 μL 2 mM dNTPs, 1 μL primer 1 (10 μM), 1 μL primer 2 (10 μM), 0.5 μL KOD plus, 1 μL 25 mM MgSO$_4$, and 16 μL ddH$_2$O. The amplification program was as follows: 94° C. 2 min; then 94° C. 30 sec, 55° C. 30 sec, 68° C. 11 min, for 25 amplification cycles, followed by incubation for 11 min at 68° C. PCR product was digested for 1 hr by directly adding 1 μL of DpnI (NEB, Cat. R0176L), then was transformed into TOP10 competent cells to obtain the plasmid of interest. The resulting recombinant expression vector was delivered to Invitrogen for sequence analysis.

2. Result of Sequence Analysis.
The linked recombinant plasmid was analyzed by Invitrogen. The DNA sequence encoding the human insulin B(1-2)-K-B(4-28)-E-R-R, A(1-21) precursor was as follows:

```
                                     SEQ ID NO: 40
TTCGTCAAGCAGCACTTGTGTGGTTCCCATTTGGTTGAGGCTCTGTACTT

GGTCTGTGGAGAAAGAGGTTTCTTTTACACCCCTGAAAGAAGAGGTATCG

TTGAGCAATGTTGCACCTCTATTTGTTCCCTGTATCAGTTGGAAAACTAC

TGCAACTAA.
```

3. Transformation of Expression Vector Comprising Recombinant Human Insulin B(1-2)-K-B(4-28)-E-R-R, A(1-21) Precursor Via Electroporation:
Expression vector comprising recombinant human insulin precursor was transformed as in Example 1.

4. Screening Clones of Recombinant Human Insulin B(1-2)-K-B(4-28)-E-R-R, A(1-21) Precursor by Using G418:
Recombinant human insulin precursor clones was screened as in Example 1.

5. Identification of Clones with Inserted Fragments of Recombinant Human Insulin Precursor by PCR:
Clones with inserted fragments of recombinant human insulin precursor were verified as in Example 1. Clone No. 072-16 was selected for further use.

6. Expression and Characterization of Recombinant Human Insulin B(1-2)-K-B(4-28)-E-R-R, A(1-21) Precursor:
Recombinant human insulin precursor was expressed and identified as in Example 1. The results showed that clone No. 072-16 expressed the protein of interest, and was selected for the following fermentation.

Step 2:
Fermentation of Recombinant Human Insulin B(1-2)-K-B(4-28)-E-R-R, A(1-21) Precursor
Clone No. 072-16 was selected for fermentation. The fermentation method was as described in Example 1.

Step 3:
Isolation and Purification of Fermentation Product
The fermentation product was isolated and purified as described in Example 1. The resulting expression product was as follows:

```
                                     SEQ ID NO: 28
FVKQHLCGSHLVEALYLVCGERGFFYTPERRGIVEQCCTSICSLYQLEN

YCN.
```

The molecular weight of the obtained product detected by LC-MS was 6015.1, which is consistent with the theoretically predicted molecular weight of 6015.93.

Step 4:
Enzymatic Digestion and Purification of Fermentation Product
Methods of enzymatic digestion and purification were as described in Example 3. After optimization of the enzymatic reaction system, digested products prepared by reverse-phase were as follows:

```
Human insulin B(1-2)-K-B(4-28)-E-R-R, A(1-21):
                                     SEQ ID NO: 13
FVKQHLCGSHLVEALYLVCGERGFFYTPERR,

SEQ ID NO: 1
GIVEQCCTSICSLYQLENYCN.
```

The molecular weight of the obtained product detected by LC-MS was 6064.8, which is consistent with the theoretically predicted molecular weight of 6063.96.

Step 5:
Analysis of Disulfide Bond Structure in Cleaved Products
The structure of disulfide bonds in cleaved products was analyzed as described in Example 1.
Results obtained from analysis of disulfide bond structure in Human insulin B(1-2)-K-B(4-28)-E-R-R, A(1-21) were as follows:

| Fragment No. | Peptide sequence | LC-MS Mol. wt. | Theoretical Mol. wt. |
|---|---|---|---|
| I | GIVE | 417.2 | 416.47 |
| II | QCCTSICSLYQLE FVKQHLCGSHLVE | 2983.41 | 2983.46 |

-continued

| Fragment No. | Peptide sequence | LC-MS Mol. wt. | Theoretical Mol. wt. |
|---|---|---|---|
| III | NYCN ALYLVCGE | 1378.3 | 1377.55 |
| IV | RGFFYTPE | 1016.1 | 1016.6 |

These results confirmed that the configurations of the disulfide bonds of recombinant human insulin B(1-2)-K-B (4-28)-E-R-R, A(1-21) were as follows: one is formed between A20 and B19; and the other two are formed between any two selected from A6 Cys, A7 Cys, A11 Cys and B7 Cys.

Example 10

Preparation of Recombinant Human Insulin B(1-2)-D-B(4-29), A(1-21) and B(1-2)-D-B(4-29), R-A(1-21)

Step 1:

Cloning and Expression of Recombinant Human Insulin B(1-2)-D-B(4-29), A(1-21) and B(1-2)-D-B(4-29), R-A(1-21) Precursors 1. Construction of the Expression Vector Comprising Recombinant Human Insulin Precursors:

B(1-2)-D-B(4-29), A(1-21) and B(1-2)-D-B(4-29), R-A (1-21) were mutated via site-directed mutagenesis by using polymerase chain reaction (PCR). Two single-stranded DNA fragments were synthesized by Invitrogen and used as primers for site-directed mutagenesis, the sequences of the primers were as follows:

```
Primer 1:
                                     SEQ ID NO: 70
5' CTTTTACACCCCTAAGAGAGGTATCGTTGAGCAATG 3'

Primer 2:
                                     SEQ ID NO: 71
5' CATTGCTCAACGATACCTCTCTTAGGGGTGTAAAAG 3.'
```

KOD kit (TOYOBO, Cat KOD-201.) 25 µL system was used in the site-directed mutagenesis procedure: 2.5 µL 10×KOD buffer, 2.5 µL 2 mM dNTPs, 1 µL primer 1 (10 µM), 1 µL primer 2 (10 µM), 0.5 µL KOD plus, 1 µL 25 mM MgSO$_4$, and 16 µL ddH$_2$O. The amplification program was as follows: 94° C. 2 min; then 94° C. 30 sec, 55° C. 30 sec, 68° C. 11 min, for 25 amplification cycles, followed by incubation for 11 min at 68° C. PCR product was digested for 1 hr by directly adding 1 µL of DpnI (NEB, Cat. R0176L), then was transformed into TOP10 competent cells to obtain the plasmid of interest. The resulting recombinant expression vector was delivered to Invitrogen for sequence analysis.

2. Results of Sequence Analysis.

The ligated recombinant plasmids were analyzed by Invitrogen. Sequences of the obtained DNA encoding the human insulin B(1-2)-D-B(4-29), A(1-21) and B(1-2)-D-B(4-29), R-A(1-21) precursors were as follows:

```
                                     SEQ ID NO: 41
TTCGTCGATCAGCACTTGTGTGGTTCCCATTTGGTTGAGGCTCTGTACTT

GGTCTGTGGAGAAAGAGGTTTCTTTTACACCCCTAAGAGAGGTATCGTTG

AGCAATGTTGCACCTCTATTTGTTCCCTGTATCAGTTGGAAAACTACTGC

AACTAA.
```

3. Transformation of Expression Vector Comprising Recombinant Human Insulin B(1-2)-D-B(4-29), A(1-21) and B(1-2)-D-B(4-29), R-A(1-21) Precursor Via Electroporation:

Expression vector comprising recombinant human insulin precursor was transformed as in Example 1.

4. Screening Clones of Recombinant Human Insulin B(1-2)-D-B(4-29), A(1-21) and B(1-2)-D-B(4-29), R-A(1-21) Precursor by Using G418:

Recombinant human insulin precursor clones were screened as in Example 1.

5. Identification of Clones with Inserted Fragments of Recombinant Human Insulin Precursor by PCR:

Inserted fragments of recombinant human insulin precursor clone were verified as in Example 1. Clone No. 087-1 was selected for further use.

6. Expression and Characterization of Recombinant Human Insulin B(1-2)-D-B(4-29), A(1-21) and B(1-2)-D-B (4-29), R-A(1-21) Precursor:

Recombinant human insulin precursor was expressed and identified as in Example 1. The results showed that clone No. 087-1 expressed the protein of interest, and was selected for the following fermentation.

Step 2:

Fermentation of Recombinant Human Insulin B(1-2)-D-B(4-29), A(1-21) and B(1-2)-D-B(4-29), R-A(1-21) Precursor Clone No. 087-1 was selected for fermentation. The fermentation method was as described in Example 1.

Step 3:

Isolation and Purification of Fermentation Product

The fermentation product was isolated and purified as described in Example 1. The resulting expression product was as follows:

```
                                     SEQ ID NO: 29
FVDQHLCGSHLVEALYLVCGERGFFYTPKRGIVEQCCTSICSLYQ

LENYCN.
```

The molecular weight of the obtained product detected by LC-MS was 5846.2, which is consistent with the theoretically predicted molecular weight of 5845.74.

Step 4:

Enzymatic Digestion and Purification of Fermentation Product

Methods of enzymatic digestion and purification were as described in Example 3. After optimization of the enzymatic reaction system, digested products prepared by reverse-phase were as follows:

```
Human insulin B(1-2)-D-B(4-29), A(1-21):
                                     SEQ ID NO: 14
FVDQHLCGSHLVEALYLVCGERGFFYTPK,

SEQ ID NO: 1
GIVEQCCTSICSLYQLENYCN.
```

The molecular weight of the obtained product detected by LC-MS was 5707.53, which is consistent with the theoretically predicted molecular weight of 5708.

The product from Step 3 was digested with Lys-C(Sigma, P3428). Digested product 2 obtained by reverse-phase was as follows:

```
Human insulin B (1-2)-D-B (4-29), R-A (1-21):
                                    SEQ ID NO: 14
FVDQHLCGSHLVEALYLVCGERGFFYTPK,

SEQ ID NO: 4
RGIVEQCCTSICSLYQLENYCN.
```

The molecular weight of the obtained product detected by LC-MS was 5864.5, which is consistent with the theoretically predicted molecular weight of 5863.72.

Step 5:

Analysis of Disulfide Bond Structure in Cleaved Products

The structure of disulfide bonds in cleaved products was analyzed as described in Example 1.

Results obtained from analysis of disulfide bond structure in Human insulin B(1-2)-D-B(4-29), A(1-21) were as follows:

| Fragment No. | Peptide sequence | LC-MS Mol. wt. | Theoretical Mol. wt. |
|---|---|---|---|
| I | GIVE | 417.2 | 416.47 |
| II | QCCTSICSLYQLE FVDQHLCGSHLVE | 2970.8 | 2970.37 |
| III | NYCN ALYLVCGE | 1377.8 | 1377.55 |
| IV | RGFFYTPK | 1015.6 | 1015.18 |

These results confirmed that the configurations of the disulfide bonds of recombinant human insulin B(1-2)-D-B (4-29), A(1-21) were as follows: one is formed between A20 and B19; and the other two are formed between any two selected from A6 Cys, A7 Cys, A11 Cys and B7 Cys.

Results from analysis of Human insulin B (1-2)-D-B (4-29), R-A (1-21) disulfide bond structure:

| Fragment No. | Peptide sequence | LC-MS Mol. wt. | Theoretical Mol. wt. |
|---|---|---|---|
| I | RGIVE | 573.3 | 572.66 |
| II | QCCTSICSLYQLE FVDQHLCGSHLVE | 2970.3 | 2970.37 |
| III | NYCN ALYLVCGE | 1377.8 | 1377.55 |
| IV | RGFFYTPK | 1015.4 | 1015.18 |

These results confirmed that the configurations of the disulfide bonds of recombinant human insulin B(1-2)-D-B (4-29), R-A(1-21) were as follows: one is formed between A20 and B19; and the other two are formed between any two selected from A6 Cys, A7 Cys, A11 Cys and B7 Cys.

Example 11

Preparation of Recombinant Human Insulin B(1-27)-K-E, A(1-20)-G

Step 1:

Cloning and Expression of Recombinant Human Insulin B(1-27)-K-E, A(1-20)-G Precursor 1. Construction of the Expression Vector Comprising Recombinant Human Insulin Precursor:

B(1-27)-K-E, A(1-20)-G was mutated via site-directed mutagenesis by using polymerase chain reaction (PCR). Two single-stranded DNA fragments were synthesized by Invitrogen and used as primers for site-directed mutagenesis. The sequences of the primers were as follows:

```
Primer 1:
                                    SEQ ID NO: 72
5' GTTGGAAAACTACTGCGGTTAAGAATTCCCTAGG 3'

Primer 2:
                                    SEQ ID NO: 73
5' CCTAGGGAATTCTTAACCGCAGTAGTTTTCCAAC 3'.
```

The recombinant vector finally obtained in Example 4 was used as template in the site-directed mutagenesis procedure. KOD kit (TOYOBO, Cat KOD-201.) 25 µL system was used: 2.5 µL 10×KOD buffer, 2.5 µL 2 mM dNTPs, 1 µL primer 1 (10 µM), primer 2 (10 µM), 0.5 µL KOD plus, 1 µL 25 mM MgSO$_4$, and 16 µL ddH$_2$O. The amplification program was as follows: 94° C. 2 min; then 94° C. 30 sec, 55° C. 30 sec, 68° C. 11 min, for 25 amplification cycles, followed by incubation for 11 min at 68° C. PCR product was digested for 1 hr by directly adding 1 µL of DpnI (NEB, Cat. R0176L), then was transformed into TOP10 competent cells to obtain the plasmid of interest. The resulting recombinant expression vector was delivered to Invitrogen for sequence analysis.

2. Result of Sequence Analysis.

The linked recombinant plasmid was analyzed by Invitrogen. The sequence of the obtained DNA encoding the human insulin B(1-27)-K-E, A(1-20)-G precursor was as follows:

```
                                    SEQ ID NO: 42
TTCGTCAACCAGCACTTGTGTGGTTCCCATTTGGTTGAGGCTCTGTACT

TGGTCTGTGGAGAAAGAGGTTTCTTTTACACCAAGGAAAAAAGAGGTAT

CGTTGAGCAATGTTGCACCTCTATTTGTTCCCTGTATCAGTTGGAAAAC

TACTGCGGTTAAGAATTCCCTAG.
```

3. Transformation for Expression Vector of Recombinant Human Insulin B(1-27)-K-E, A(1-20)-G Precursor Via Electroporation:

Expression vector of recombinant human insulin B(1-27)-K-E, A(1-20)-G precursor was transformed as in Example 1.

4. Screening Clones of Recombinant Human Insulin B(1-27)-K-E, A(1-20)-G Precursor by Using G418:

Recombinant human insulin precursor clone was screened as in Example 1.

5. Identification of Clones with Inserted Fragments of Recombinant Human Insulin B(1-27)-K-E, A(1-20)-G Precursor by PCR:

Clones inserted with fragments of recombinant human insulin precursor B(1-27)-K-E, A(1-20)-G were verified as in Example 1. Clone No. 094-4 was selected for further use.

6. Expression and Characterization of Recombinant Human Insulin B(1-27)-K-E, A(1-20)-G Precursor:

Recombinant human insulin precursor was expressed and identified as in Example 1. The results showed that clone No. 094-4 expressed the protein of interest, and was selected for the following fermentation.

Step 2:
Fermentation of Recombinant Human Insulin Precursor
Clone No. 094-4 was selected for fermentation. The fermentation method was as described in Example 1.

Step 3:
Isolation and Purification of Fermentation Product
The fermentation product was isolated and purified as described in Example 1. The resulting B(1-27)-K-E, A(1-20)-G precursor was as follows:

```
                                       SEQ ID NO: 30
FVNQHLCGSHLVEALYLVCGERGFFYTKEKRGIVEQCCTSICSLYQ

LENYCG.
```

The molecular weight of the obtained product detected by LC-MS was 5948, which is consistent with the theoretically predicted molecular weight of 5947.85.

Step 4:
Enzymatic Digestion and Purification of Fermentation Product

Methods of enzymatic digestion and purification were as described in Example 1.

After optimization of the enzymatic reaction system, digested products prepared by reverse-phase were as follows:

```
    Human insulin B(1-27)-K-E, A(1-20)-G:
                                       SEQ ID NO: 15
    FVNQHLCGSHLVEALYLVCGERGFFYTKE,

SEQ ID NO: 2
    GIVEQCCTSICSLYQLENYCG.
```

The molecular weight of the obtained product detected by LC-MS was 5681, which is consistent with the theoretically predicted molecular weight of 5681.49.

Step 5:
Analysis of Disulfide Bond Structure in Cleaved Products
The structure of disulfide bonds in cleaved products was analyzed as described in Example 1.

Results obtained from analysis of disulfide bond structure in Human insulin B(1-27)-K-E, A(1-20)-G were as follows:

| Fragment No. | Peptide sequence | LC-MS Mol. wt. | Theoretical Mol. wt. |
|---|---|---|---|
| I | GIVE | 416 | 416.47 |
| II | QCCTSICSLYQLE FVNQHLCGSHLVE | 2969 | 2969.39 |
| III | NYCG ALYLVCGE | 1320 | 1320.5 |
| IV | RGFFYTKE | 1047 | 1047.18 |

These results confirmed that the configurations of the disulfide bonds of recombinant human insulin B(1-27)-K-E, A(1-20)-G were as follows: one is formed between A20 and B19; and the other two are formed between any two selected from A6 Cys, A7 Cys, A11 Cys and B7 Cys.

Example 12

Preparation of Recombinant Human Insulin B(1-2)-K-B(4-28)-E-E, A(1-20)-G

Step 1:
Cloning and Expression of Recombinant Human Insulin B(1-2)-K-B(4-28)-E-E, A(1-20)-G Precursor 1. Construction of the Expression Vector Comprising Recombinant Human Insulin B(1-2)-K-B(4-28)-E-E, A(1-20)-G Precursor:

B(1-2)-K-B(4-28)-E-E, A(1-20)-G precursor was mutated via site-directed mutagenesis by using polymerase chain reaction (PCR). Two single-stranded DNA fragments were synthesized by Invitrogen and used as primers for site-directed mutagenesis, the sequences of the primers were as follows:

```
Primer 1:
                                       SEQ ID NO: 74
    5' GTTGGAAAACTACTGCGGTTAAGAATTCCCTAGG 3'

Primer 2:
                                       SEQ ID NO: 75
    5' CCTAGGGAATTCTTAACCGCAGTAGTTTTCCAAC 3'.
```

The recombinant vector finally obtained in Example 6 was used as template in the site-directed mutagenesis procedure. KOD kit (TOYOBO, Cat KOD-201) 25 µL system was used: 2.5 µL 10×KOD buffer, 2.5 µL 2 mM dNTPs, 1 µL primer 1 (10 µM), 1 µL primer 2 (10 µM), 0.5 µL KOD plus, 1 µL 25 mM MgSO$_4$, and 16 µL ddH$_2$O. The amplification program was as follows: 94° C. 2 min; then 94° C. 30 sec, 55° C. 30 sec, 68° C. 11 min, for 25 amplification cycles, followed by incubation for 11 min at 68° C. PCR product was digested for 1 hr by directly adding 1 µL of DpnI (NEB, Cat. R0176L), then was transformed into TOP10 competent cells to obtain the plasmid of interest. The resulting recombinant expression vector was delivered to Invitrogen for sequence analysis.

2. Result of Sequence Analysis.

The ligated recombinant plasmid was analyzed by Invitrogen. The sequence of the obtained DNA encoding the human insulin B(1-2)-K-B(4-28)-E-E, A(1-20)-G precursor was as follows:

```
                                       SEQ ID NO: 43
TTCGTCAAGCAGCACTTGTGTGGTTCCCATTTGGTTGAGGCTCTGTACT

TGGTCTGTGGAGAAAGAGGTTTCTTTTACACCCCTGAAGAAAAAGAGG

TATCGTTGAGCAATGTTGCACCTCTATTTGTTCCCTGTATCAGTTGGAA

AACTACTGCGGTTAAGAATTCCCTAGG.
```

3. Transformation of Expression Vector Comprising Recombinant Human Insulin B(1-2)-K-B(4-28)-E-E, A(1-20)-G Precursor Via Electroporation:

Expression vector comprising recombinant human insulin B(1-2)-K-B(4-28)-E-E, A(1-20)-G precursor was transformed as in Example 1.

4. Screening Clones of Recombinant Human Insulin B(1-2)-K-B(4-28)-E-E, A(1-20)-G Precursor by Using G418:

Clones with recombinant human insulin B(1-2)-K-B(4-28)-E-E, A(1-20)-G precursor were screened as in Example 1.

5. Identification of Clones with Inserted Fragments of Recombinant Human Insulin B(1-2)-K-B(4-28)-E-E, A(1-20)-G Precursor by PCR:

Clones with inserted fragments of recombinant human insulin precursor were verified as in Example 1. Clone 093-15 was selected for further use.

6. Expression and Characterization of Recombinant Human Insulin B(1-2)-K-B(4-28)-E-E, A(1-20)-G Precursor:

Recombinant human insulin B(1-2)-K-B(4-28)-E-E, A(1-20)-G precursor was expressed and identified as in Example 1. The results showed that clone No. 093-15 expressed the protein of interest, and was selected for following fermentation.

Step 2:

Fermentation of Recombinant Human Insulin Precursor

Clone No. 093-15 was selected for fermentation. The fermentation method was as described in Example 1.

Step 3:

Isolation and Purification of Fermentation Product

The fermentation product was isolated and purificated as described in Example 1. The resulting expression product was as follows:

```
                                              SEQ ID NO: 20
FVKQHLCGSHLVEALYLVCGERGFFYTPEEKRGIVEQCCTSICSLYQLE
NYCG.
```

The molecular weight of the obtained product detected by LC-MS was 6060, which is consistent with the theoretically predicted molecular weight of 6060.

Step 4:

Enzymatic Digestion and Purification of Fermentation Product

Methods of enzymatic digestion and purification were as described in Example 1. After optimization of the enzymatic reaction system, digested products prepared by reverse-phase were as follows:

```
Human insulin B(1-2)-K-B(4-28)-E-E, A(1-20)-G:
                                     SEQ ID NO: 16
FVKQHLCGSHLVEALYLVCGERGFFYTPEE,

SEQ ID NO: 2
GIVEQCCTSICSLYQLENYCG.
```

The molecular weight of the obtained product detected by LC-MS was 5793, which is consistent with the theoretically predicted molecular weight of 5793.6.

Step 5:

Analysis of Disulfide Bond Structure in Cleaved Products

The structure of disulfide bonds in cleaved products was analyzed as described in Example 1.

Results obtained from analysis of disulfide bond structure in Human insulin B(1-2)-K-B(4-28)-E-E, A(1-20)-G were as follows:

| Fragment No. | Peptide sequence | LC-MS Mol. wt. | Theoretical Mol. wt. |
| --- | --- | --- | --- |
| I | GIVE | 416 | 416.47 |
| II | QCCTSICSLYQLE FVKQHLCGSHLVE | 2982.6 | 2983.46 |
| III | NYCG ALYLVCGE | 1319.9 | 1320.5 |
| IV | RGFFYTPEK | 1144.8 | 1345.24 |

These results confirmed that the configurations of the disulfide bonds of recombinant human insulin B(1-2)-K-B(4-28)-E-E, A(1-20)-G were as follows: one is formed between A20 and B19; and the other two are formed between any two selected from A6 Cys, A7 Cys, A11 Cys and B7 Cys.

Example 13

Preparation of Recombinant Human Insulin B(1-2)-D-B(4-29)-R, A(1-20)-G, B(1-2)-D-B(4-29), A(1-20)-G and B(1-2)-D-B(4-29), R-A(1-20)-G Step 1:

Cloning and Expression of Recombinant Human Insulin B(1-2)-D-B(4-29)-R, A(1-20)-G, B(1-2)-D-B(4-29), A(1-20)-G and B(1-2)-D-B(4-29), R-A(1-20)-G Precursors 1. Construction of the Expression Vector Comprising Recombinant Human Insulin Precursors:

B(1-2)-D-B(4-29)-R, A(1-20)-G, B(1-2)-D-B(4-29), A(1-20)-G and B(1-2)-D-B(4-29), R-A(1-20)-G were mutated via site-directed mutagenesis by using polymerase chain reaction (PCR). Two single-stranded DNA fragments were synthesized by Invitrogen and used as primers for site-directed mutagenesis. The sequences of the primers were as follows:

```
Primer 1:
                                       SEQ ID NO: 76
5' GTTGGAAAACTACTGCGGTTAAGAATTCCCTAGG 3'

Primer 2:
                                       SEQ ID NO: 67
5' CCTAGGGAATTCTTAACCGCAGTAGTTTTCCAAC 3'.
```

The recombinant vector finally obtained in Example 10 was used as template in the site-directed mutagenesis procedure. KOD kit (TOYOBO, Cat KOD-201.) 25 µL system was applied: 2.5 µL 10×KOD buffer, 2.5 µL 2 mM dNTPs, 1 µL primer 1 (10 µM), primer 2 (10 µM), 0.5 µL KOD plus, 1 µL 25 mM MgSO$_4$, and 16 µL ddH$_2$O. The amplification program was as follows: 94° C. 2 min; then 94° C. 30 sec, 55° C. 30 sec, 68° C. 11 min, for 25 amplification cycles, followed by incubation for 11 min at 68° C. PCR product was digested for 1 hr by directly adding 1 µL of DpnI (NEB, Cat. R0176L), then was transformed into TOP10 competent cells to obtain the plasmid of interest. The resulting recombinant expression vector was delivered to Invitrogen for sequence analysis.

2. Result of Sequence Analysis.

The ligated recombinant plasmids were analyzed by Invitrogen. Sequences of the obtained DNA encoding the human insulin B(1-2)-D-B(4-29)-R, A(1-20)-G, B(1-2)-D-B(4-29), A(1-20)-G and B(1-2)-D-B(4-29), R-A(1-20)-G precursors were as follows:

```
                                                    SEQ ID NO: 44
TTCGTCGATCAGCACTTGTGTGGTTCCCATTTGGTTGAGGCTCTGTACT

TGGTCTGTGGAGAAAGAGGTTTCTTTTACACCCCTAAGAGAGGTATCGT

TGAGCAATGTTGCACCTCTATTTGTTCCCTGTATCAGTTGGAAAACTAC

TGCGGTTAAGAATTCCCTAGG.
```

3. Transformation of Expression Vector of Recombinant Human Insulin B(1-2)-D-B(4-29)-R, A(1-20)-G,B(1-2)-D-B(4-29), A(1-20)-G and B(1-2)-D-B(4-29), R-A(1-20)-G Precursors Via Electroporation:

Expression vector of recombinant human insulin precursor was transformed as Example 1.

4. Screening Clones of Recombinant Human Insulin B(1-2)-D-B(4-29)-R, A(1-20)-G, B(1-2)-D-B(4-29), A(1-20)-G and B(1-2)-D-B(4-29), R-A(1-20)-G Precursors by Using G418:

Clones with recombinant human insulin precursor were screened as in Example 1.

5. Identification of Clones with Inserted Fragments of Recombinant Human Insulin B(1-2)-D-B(4-29)-R, A(1-20)-G,B(1-2)-D-B(4-29), A(1-20)-G and B(1-2)-D-B(4-29), R-A(1-20)-G Precursors by PCR:

Clones with inserted fragments of recombinant human insulin precursor were verified as in Example 1. Clone No. 096-4 was selected for further use.

6. Expression and Characterization of Recombinant Human Insulin B(1-2)-D-B(4-29)-R, A(1-20)-G, B(1-2)-D-B(4-29), A(1-20)-G and B(1-2)-D-B(4-29), R-A(1-20)-G Precursor:

Recombinant human insulin precursor was expressed and identified as in Example 1. The results showed that clone No. 096-4 expressed the protein of interest, and was selected for the following fermentation.

Step 2:

Fermentation of Recombinant Human Insulin B(1-2)-D-B(4-29)-R, A(1-20)-G,B(1-2)-D-B(4-29), A(1-20)-G and B(1-2)-D-B(4-29), R-A(1-20)-G Precursor Clone No. 096-4 was selected for fermentation. The fermentation method was as described in Example 1.

Step 3:

Isolation and Purification of Fermentation Product

The fermentation product was isolated and purified as described in Example 1. The resulting expression product precursor was as follows:

```
                                                    SEQ ID NO: 31
FVDQHLCGSHLVEALYLVCGERGFFYTP KRGIVEQCCTSICSLYQLEN

YCG.
```

The molecular weight of the obtained product detected by LC-MS was 5789, which is consistent with the theoretically predicted molecular weight of 5788.67.

Step 4:

Enzymatic Digestion and Purification of Fermentation Product

Methods of enzymatic digestion and purification were as described in Example 3. After optimization of the enzymatic reaction system, digested products prepared by reverse-phase were as follows:

```
Human insulin B(1-2)-D-B(4-29)-R, A(1-20)-G:
                                                    SEQ ID NO: 17
FVDQHLCGSHLVEALYLVCGERGFFYTPKR,

SEQ ID NO: 2
GIVEQCCTSICSLYQLENYCG.
```

The molecular weight of the obtained product detected by LC-MS was 5807, which is consistent with the theoretically predicted molecular weight of 5806.67.

Enzymatic digestion and purification methods were as in Example 1. After optimization of the enzymatic reaction system, the digested product 2 obtained by reverse-phase preparative were as follows:

```
Human insulin B(1-2)-D-B(4-29), A(1-20)-G:
                                                    SEQ ID NO: 18
FVDQHLCGSHLVEALYLVCGERGFFYTPK,

SEQ ID NO: 2
GIVEQCCTSICSLYQLENYCG.
```

The molecular weight of the obtained product detected by LC-MS was 5651, which is consistent with the theoretically predicted molecular weight of 5650.48.

The product from Step 3 (096-4 fermentation) was digested using the same enzymatic method as described in Example 10. The digested product prepared by reverse-phase was as follows:

```
Human insulin B(1-2)-D-B(4-29), R-A(1-20)-G:
                                                    SEQ ID NO: 18
FVDQHLCGSHLVEALYLVCGERGFFYTPK,

SEQ ID NO: 3
RGIVEQCCTSICSLYQLENYCG.
```

The molecular weight of the obtained product detected by LC-MS was 5807, which is consistent with the theoretically predicted molecular weight of 5806.7.

Step 5:

Analysis of Disulfide Bond Structure in Cleaved Products

The structure of disulfide bonds in cleaved products was analyzed as described in Example 1.

Results obtained from analysis of disulfide bond structure in Human insulin B(1-2)-D-B(4-29)-R, A(1-20)-G were as follows:

| Fragment NO | Peptide sequence | LC-MS Mol. wt. | Theoretical Mol. wt. |
|---|---|---|---|
| I | GIVE | 416 | 416.47 |
| II | QCCTSICSLYQLE FVDQHLCGSHLVE | 2970 | 2970.3 |
| III | NYCG ALYLVCGE | 1320 | 1320.5 |
| IV | RGFFYTPKR | 1171 | 1171.37 |

These results confirmed that the configurations of the disulfide bonds of recombinant human insulin B(1-2)-D-B(4-29)-R, A(1-20)-G were as follows: one is formed between A20 and B19; and the other two are formed between any two selected from A6 Cys, A7 Cys, A11 Cys and B7 Cys.

Results from Analysis of Human insulin B (1-2)-D-B (4-29), A (1-20)-G disulfide Structure:

| Fragment No. | Peptide sequence | LC-MS Mol. wt. | Theoretical Mol. wt. |
|---|---|---|---|
| I | GIVE | 416 | 416.47 |
| II | QCCTSICSLYQLE FVDQHLCGSHLVE | 2970 | 2970.3 |
| III | NYCG ALYLVCGE | 1320 | 1320.5 |
| IV | RGFFYTPK | 1015 | 1015.18 |

These results confirmed that the configurations of the disulfide bonds of recombinant human insulin B(1-2)-D-B (4-29)-R, A(1-20)-G were as follows: one is formed between A20 and B19; and the other two are formed between any two selected from A6 Cys, A7 Cys, A11 Cys and B7 Cys.

Results from Analysis of Human insulin B (1-2)-D-B(4-29), R-A (1-20)-G disulfide structure:

| Fragment No. | Peptide sequence | LC-MS Mol. wt. | Theoretical Mol. wt. |
|---|---|---|---|
| I | RGIVE | 573 | 572.66 |
| II | QCCTSICSLYQLE FVDQHLCGSHLVE | 2970 | 2970.3 |
| III | NYCG ALYLVCGE | 1320 | 1320.5 |
| IV | RGFFYTPK | 1015 | 1015.18 |

These results confirmed that the configurations of the disulfide bonds of recombinant human insulin B(1-2)-D-B (4-29)-R, A(1-20)-G were as follows: one is formed between A20 and B19; and the other two are formed between any two selected from A6 Cys, A7 Cys, A11 Cys and B7 Cys.

Example 14

Preparation of B28D-N$^{\epsilon B29}$—(N$^{\alpha}$—(HOOC (CH$_2$)$_{14}$CO)-γ-Glu)-B30E Human Insulin (HS061)

1. Preparation of Methyl Hexadecandioyl-Glu (OSu)-OMe

Hexadecanedioic acid (5.0 g, 17.48 mmol) was dissolved in anhydrous methanol (50 mL), cooled with liquid nitrogen to −10° C., then thionyl chloride was added dropwise (3.2 mL, 43.7 mmol) at −10° C. for 20 min, and the reaction solution was slowly warmed to reflux for 4 hrs. The reaction was terminated, and the reaction solution was cooled to room temperature and concentrated to dryness to obtain 5.15 g (94%) of hexadecanedioic acid dimethyl ester.

Hexadecanedioic acid dimethyl ester (5.0 g, 15.92 mmol) was dissolved in anhydrous methanol (50 mL). Barium hydroxide octahydrate (Ba(OH)$_2$.8H$_2$O) (5.0 g, 15.8 mmol) dissolved in methanol was added dropwise into hexadecanedioic acid dimethyl ester, and the reaction solution was slowly warmed to 30° C. and the mixture was stirred for 24 hr. After methanol was removed via vacuum concentration, the residue was dissolved in ethyl acetate and washed three times with 0.1M hydrochloride acid (HCl). The organic phase was collected and dried over anhydrous sodium sulfate, filtered, and concentrated under vacuum and dried in vacuum to obtain 4.55 g (yield 95%) hexadecanedioic acid monomethyl ester.

Hexadecanedioic acid monomethyl ester (2.0 g, 6.67 mmol) was dissolved in dichloromethane (DCM) (50 mL), followed by addition of N-hydroxysuccinamide (HOSu) (0.92 g, 8.0 mmol), then N,N-dicyclohexylcarbodiimide (DCC) (2.06 g, 10 mmol) was added, and stirred for 24 hr at room temperature. The reaction solution was filtered, the organic phase was washed three times with 200 mL 0.1M HCl, and then dried over anhydrous sodium sulfate, filtered and concentrated under vacuum to obtain 2.45 g (92%) methyl cetane diacid succinimide ester.

H-Glu-OMe (0.81 g, 5.04 mmol) was dissolved in 5 mL of purified water, and the obtained solution was added to tetrahydrofuran (THF) (50 mL) solution dissolved with methyl cetane diacid succinimide ester (1.0 g, 2.52 mmol). Diisopropylethylamine (DIEA) (0.65 g, 5.04 mmol) was added to the obtained mixture and stirred at room temperature for 24 hrs. The reaction solution was filtered and concentrated under vacuum. The residue was dissolved in ethyl acetate, and the organic phase was washed three times with 200 mL 0.1M HCl. Then the organic phase was collected and dried over anhydrous sodium sulfate, filtered, concentrated under vacuum, and purified by reverse phase high performance liquid chromatography. 0.7 g (63%) methyl hexadecandioyl-Glu-OMe (ESI-MS: 444.3 ([M+H]+)) was obtained after concentration.

Methyl hexadecandioyl-Glu-OMe (0.3 g, 0.677 mmol) was dissolved in DCM (20 mL), then HOSu (85.7 mg, 0.745 mmol) and DCC (0.167 g, 0.812 mmol) were added, stirred at room temperature for 24 hrs, filtered, washed with 0.1M HCl and the organic phase was collected, dried over anhydrous sodium sulfate, filtered and concentrated under vacuum, and dried in vacuum to obtain 0.3 g (82%) methyl hexadecandioyl-Glu (OSu)-OMe, which has the following structural formula:

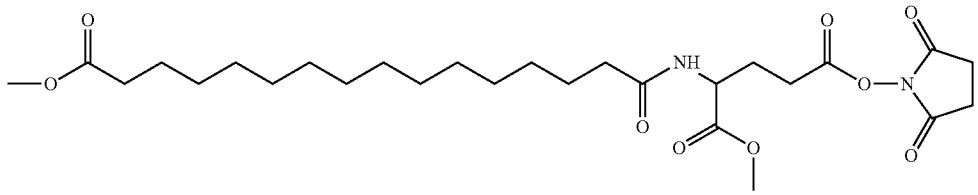 [SMILES: COC(=O)CCCCCCCCCCCCCCC(=O)NC(CCC(=O)ON1C(=O)CCC1=O)C(=O)OC]

2. Preparation of B28D-N$^{\epsilon B29}$—(N$^{\alpha}$—(HOOC (CH$_2$)$_{14}$CO)-γ-Glu)-B30E Human Insulin Precursor Recombinant human insulin B(1-27)-D-K-E, A(1-21) (50 mg, 8.5 mmol) (Example 7) was dissolved in 10 mL of 10 mM HCl. The pH value of the solution was adjusted to about 10.5 with 0.2M NaOH. Methyl hexadecandioyl-Glu (OSu)-OMe (13.9 mg, 25.6 mmol) was dissolved in 10 mL of acetonitrile and then added to the above B(1-27)-D-K-E, A(1-21) human insulin solution to start reaction for 40 min. The reaction process was controlled by RP-HPLC. 40 min later, the pH value of the solution was adjusted to about 2.2 with 10% HCl, the reaction was terminated, and crude precursor solution was obtained.

3. Purification of B28D-N$^{\epsilon B29}$—(N$^{\alpha}$—(HOOC(CH$_2$)$_{14}$CO)-γ-Glu)-B30E Human Insulin Precursor The above crude precursor solution was diluted with water to make the content of the organic phase about 30% (v:v). After being filtered through a 0.45 μm membrane, the solution was purified by RP-HPLC, wherein the reverse phase column was Luna C18, 250×25 mm, 5 μm, 100 Å, mobile phase A was 0.1% TFA/H$_2$O, and mobile phase B was 0.1% TFA/ACN. The desired product was eluted and collected with a gradient phase B from 38% to 68% at a flow rate of 20 mL/min over 60 min, ESI-MS: 1570.8 ([M+4H]4+) to obtain the purified precursor solution.

4. Saponification of B28D-N$^{\epsilon B29}$—(N$^{\alpha}$—(HOOC(CH$_2$)$_{14}$CO)-γ-Glu)-B30E Human Insulin Precursor Acetonitrile was removed from the purified precursor solution via vacuum concentration. Then the pH value of the solution was adjusted to 8.0 with 10% NaOH solution and saponified by adding an equal volume of 0.2M ice-cooled NaOH. The saponified product was analyzed by RP-HPLC. The reaction was terminated by adding 10% HCl.

5. Purification and Lyophilization of Saponified Human Insulin B28D-N$^{\epsilon B29}$—(N$^{\alpha}$—(HOOC(CH$_2$)$_{14}$CO)-γ-Glu)-B30E Precursor Solution The above saponified precursor solution was diluted with acetonitrile to make the content of the organic phase about 30% (v:v). After being filtered through a 0.45 μm membrane, the solution was purified with RP-HPLC, wherein the reverse phase column was Luna C18, 250×25 mm, 5 μm, 100 Å, mobile phase A was 0.1% TFA/H$_2$O, and mobile phase B was 0.1% TFA/ACN. The desired product was eluted and collected with a gradient phase B from 35% to 65% at a flow rate of 20 mL/min over 60 min, lyophilized and 3.6 mg of product (purity 97.9%) was obtained. The resulting product has a structure as follows:

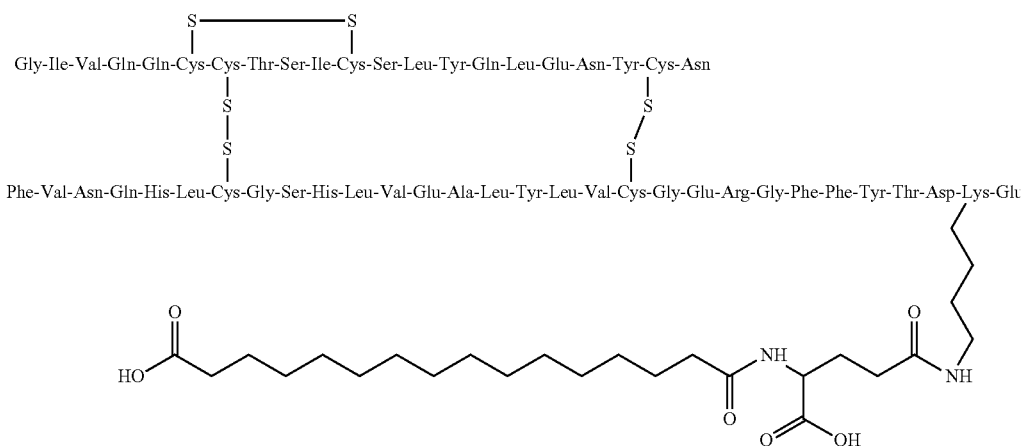

6. Confirmation of the Structure of Human Insulin B28D-N$^{\epsilon B29}$—(N$^{\alpha}$—(HOOC(CH$_2$)$_{14}$CO)-γ-Glu)-B30E The molecular weight of human insulin B28D-N$^{\epsilon B29}$—(N$^{\alpha}$—(HOOC(CH$_2$)$_{14}$CO)-γ-Glu)-B30E detected by ESI-MS assay was 6251.65, which is consistent with the theoretically predicted molecular weight of 6251.16.

Human insulin B28D-N$^{\epsilon B29}$—N$^{\alpha}$—(HOOC(CH$_2$)$_{14}$CO)-γ-Glu)-B30E was digested with trypsin. The digested products were analyzed by LC-MS. The results showed that the molecular weights of the two fragments F1 and F2 were 4865 and 1403, respectively, consistent with the theoretical molecular weight of the digested products. Fragment F2 corresponds to the modified B-chain fragment. Modified sites were proven to be the same as expected.

Example 15

Preparation of Human Insulin B28D-N$^{\epsilon B29}$—(N$^{\alpha}$—(HO(CH$_2$)$_{15}$CO)-γ-Glu)-B30E (HS062)

1. 16-hydroxy hexadecanoyl-Glu (OSu)-OMe 16-hydroxy hexadecanoic acid (3.0 g, 11.03 mmol) was dissolved in DCM (50 mL), then O—(N-succinimidyl)-1,1,3,3-tetramethyluronium tetrafluoroborate ester and N, N-diisopropylethylamine (1.71 g, 13.2 mmol) were added. The reaction solution was stirred at room temperature for 24 hrs. After filtration, the organic phase was washed three times with 0.1M HCl and dried over anhydrous sodium sulfate. The organic phase was concentrated under vacuum, and 3.5 g (70%) 16-hydroxy hexadecane succinimide ester were obtained.

H-Glu-OMe (3.4 g, 21.64 mmol) dissolved in 5 mL of purified water was added to THF solution (50 mL) dissolved with 16-hydroxyl hexadecane succinimide ester. DIEA (2.8 g, 21.64 mmol) was added and stirred at room temperature for 24 hrs. The reaction solution was filtered and concentrated under vacuum. The residue was dissolved in ethyl acetate, and the organic phase was washed three times with 200 mL 0.1M HCl. The organic phase was collected and dried over anhydrous sodium sulfate, filtered, concentrated under vacuum and purified by reverse phase high performance liquid chromatography. After final concentration, 2.5 g (45%) 16-hydroxy hexadecanoyl-Glu-OMe, ESI-MS: 417 ([M+H]+) were obtained.

16-hydroxy hexadecanoyl-Glu-OMe (1.0 g, 24 mmol) was dissolved in DCM (20 mL), then HOSu (0.305 g, 2.65 mmol) and EDC.HCl (0.69 g, 3.61 mmol) were added, stirred at room temperature for 24 hrs, filtered, washed with 0.1M HCl. The organic phase was collected, dried over anhydrous sodium sulfate, filtered and concentrated under vacuum, dried in vacuum, and 0.9 g of 16-hydroxy hexadecanoyl-Glu (OSu)-OMe (purity was 73%) were obtained, which has the following structural formula:

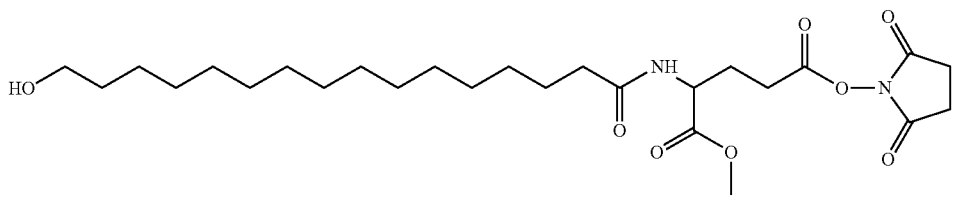 [SMILES: COC(=O)C(CCC(=O)ON1C(=O)CCC1=O)NC(=O)CCCCCCCCCCCCCCCO]

2. Preparation of Human Insulin B28D-N$^{\epsilon B29}$—(N$^{\alpha}$—(HO(CH$_2$)$_{15}$CO)-γ-Glu)-B30E Precursor Recombinant human insulin B(1-27)-D-K-E, A(1-21) (50 mg, 8.5 mmol) was dissolved in 10 mL of 10 mM HCl. The pH value of the solution was adjusted to about 10.5 with 0.2M NaOH. 16-hydroxy hexadecanoyl-Glu (OSu)-OMe (13.2 mg, 25.5 mmol) was dissolved in 10 mL of acetonitrile and then added to the above B(1-27)-D-K-E, A(1-21) human insulin solution to start reacting for 40 min. The reaction process was monitored by RP-HPLC. 40 min later, the pH value of the solution was adjusted to about 2.2 with 10% HCl. Then the reaction was terminated, and crude precursor solution was obtained.

3. Purification of Human Insulin B28D-N$^{\epsilon B29}$—N$^{\alpha}$—(HO(CH$_2$)$_{15}$CO)-γ-Glu)-B30E Precursor The above crude precursor solution was diluted with water to make the content of the organic phase about 30% (v:v), and after being filtered through a 0.45 μm membrane, the solution was purified with RP-HPLC, wherein the reverse phase column was Luna C18, 250×25 mm, 5 μm, 100 Å, mobile phase A was 0.1% TFA/H$_2$O, and mobile phase B was 0.1% TFA/ACN. The desired product was eluted and collected with a gradient phase B from 35% to 65% at a flow rate of 20 mL/min over 60 min, ESI-MS: 1563.4 ([M+4H]4+), the purified precursor solution was obtained.

4. Saponification of Human Insulin B28D-N$^{\epsilon B29}$—N$^{\alpha}$—(HO(CH$_2$)$_{15}$CO)-γ-Glu)-B30E Precursor Acetonitrile was removed from the purified precursor solution via vacuum concentration. Then the pH value of the solution was adjusted to 8.0 with 10% NaOH solution and saponified for 50 min by adding an equal volume of 0.2M ice-cooled NaOH. The saponified product was analyzed by RP-HPLC. After 50 min, the reaction was terminated by adding 10% HCl.

5. Purification and Lyophilization of Human Insulin B28D-N$^{\epsilon B29}$—(N$^{\alpha}$—(HO(CH$_2$)$_{15}$CO)-γ-Glu)-B30E Precursor The above saponified precursor solution was diluted with acetonitrile to make the content of the organic phase about 30% (v:v). After being filtered through a 0.45 μM membrane, the solution was purified with RP-HPLC, wherein the reverse phase column was Luna C18, 250×25 mm, 5 μm, 100 Å, mobile phase A was 0.1% TFA/H$_2$O, and mobile phase B was 0.1% TFA/ACN. The desired product was eluted and collected with a gradient phase B from 35% to 65% at a flow rate of 20 mL/min over 60 min, lyophilized, and 10 mg product was obtained (purity 94.3%). The resulting product has a structural formula as follows:

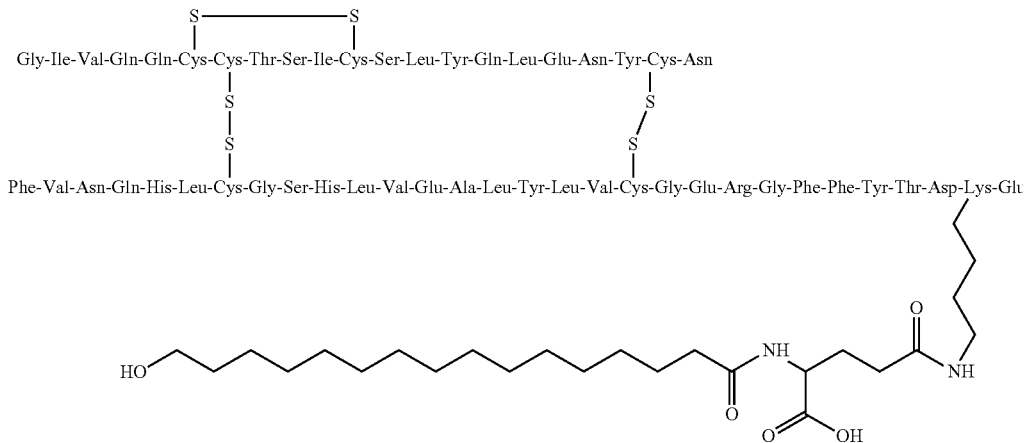

6. Confirmation of the Structure of Human Insulin B28D-N$^{\epsilon B29}$—(N$^{\alpha}$—(HO(CH$_2$)$_{15}$CO)-γ-Glu)-B30E The molecular weight of human insulin B28D-N$^{\epsilon B29}$—(N$^{\alpha}$—(HO(CH$_2$)$_{15}$CO)-γ-Glu)-B30E detected by ESI-MS was 6237.52, which is consistent with the theoretically predicted molecular weight of 6237.17.

Human insulin B28D-N$^{\epsilon B29}$—(N$^{\alpha}$—(HOC(CH$_2$)$_{15}$CO)-γ-Glu)-B30E was digested with trypsin. The digested products were analyzed by LC-MS. The results showed the molecular weights of the two fragments F1 and F2 were 4865 and 1389, respectively, consistent with the theoretical molecular weight of the digested products. Fragment F2 corresponds to modified B-chain fragment. Modified sites were proven to be the same as expected.

Example 16

Preparation of N$^{\alpha}$—(HOOC(CH$_2$)$_{14}$CO)—N$^{\epsilon}$—(OCCH$_2$CH$_2$CO—(B28D-N$^{\epsilon B29}$-B30E Human Insulin))-Lys-OH (HS067)

1. Preparation of N$^{\alpha}$-(Methyl Hexadecandioyl)-Nε-(3-Acyl Propionic Acid-OSu) Lysine Methyl Ester H-Lys(Fmoc)-OMe (4.33 g, 11.29 mmol) dissolved in 5 mL of purified water was added to a THF (50 mL) solution dissolved with methyl-hexadecanoic acid succinimidyl ester (3.0 g, 7.55 mmol). DIEA (1.46 g, 11.29 mmol) was added and stirred at room temperature for 24 hrs. The reaction solution was filtered and concentrated under vacuum. The residue was dissolved in ethyl acetate, and the organic phase was washed three times with 200 mL 0.1M HCl. Then the organic phase was collected and dried over anhydrous sodium sulfate. After filtration and vacuum concentration, the product was crystallized by using 200 mL of acetonitrile:water=10:1 (v:v). 5.0 g (99.6%) methyl hexadecandioyl-Lys (Fmoc)-OMe were obtained.

Methyl hexadecandioyl-Lys (Fmoc)-OMe (5.0 g, 7.52 mmol) was dissolved in THF (80 mL), and then hexahydropyridine (20 mL) was added and stirred at room temperature for 20 min. The solution was concentrated under vacuum. The resulting solid was dissolved in ethyl acetate (100 mL), washed with water three times, and the organic phase was dried over anhydrous sodium sulfate for 30 min. After filtration and concentration under vacuum, the resulting solid was dissolved in chloroform (100 mL), into which succinic anhydride (11.34 g, 113.4 mmol) and N, N-diisopropylethylamine (14.1 g, 113.4 mmol) were added, and the reaction mixture was stirred at room temperature for 2 hrs. 100° C. purified water (100 mL) was added into the reaction solution three times, for washing. The organic phase was dried over anhydrous sodium sulfate for 30 min. After filtration and vacuum concentration, the obtained solid was purified by reverse phase HPLC. After concentration, 3.45 g (84.7%) $N^\alpha$-(methyl hexadecandioyl)-$N^\epsilon$-(3-acyl propionic acid) Lys methyl ester, ESI-MS: 543.6 ([M+H]+) were obtained.

$N^\alpha$-(methyl hexadecandioyl)-$N^\epsilon$-(3-acyl propionic acid) lysine methyl ester (0.5 g, 0.9 mmol) was dissolved in DCM (50 mL). HOSu (0.116 g, 2.0 mmol) and EDC.HCl (0.265 g, 2.0 mmol) were added, then stirred at room temperature for 48 hrs, filtered, then washed with 0.1M HCl, and the organic phase was collected. The organic phase was dried over anhydrous sodium sulfate for 30 min. After filtration and vacuum concentration, 0.36 g (63%) $N^\alpha$-(methyl hexadecandioyl)-$N^\epsilon$-(3-acyl propionic acid-OSu)lysine methyl ester were obtained, which has a structural formula as shown below:

2. Preparation of $N^\alpha$—(HOOC(CH$_2$)$_{14}$CO)—$N^\epsilon$—(OCCH$_2$CH$_2$CO-(B28D-$N^{\epsilon B29}$-B30E Human Insulin))-Lys-OH Precursor Recombinant human insulin B(1-27)-D-K-E, A(1-21) (50 mg, 8.5 mmol) was dissolved in 10 mL of 10 mM HCl, then the pH value was adjusted to about 10.5 with 0.2M NaOH. $N^\alpha$-(methyl hexadecandioyl)-$N^\epsilon$-(3-acyl propionic acid-OSu) lysine methyl ester (16.4 mg, 25.6 mmol) dissolved in 10 mL of acetonitrile was added into the above B(1-27)-D-K-E, A(1-21) human insulin solution to start the reaction. The reaction process was monitored by RP-HPLC. The pH value of the solution was adjusted to about 2.2 with 10% HCl After 40 min, the reaction was terminated and crude precursor solution was obtained.

3. Purification of $N^\alpha$—(HOOC(CH$_2$)$_{14}$CO)—$N^\epsilon$—(OCCH$_2$CH$_2$CO-(B28D-$N^{\epsilon B29}$-B30E Human Insulin))-Lys-OH Precursor The above crude precursor solution was diluted with water to make the content of the organic phase about 30% (v:v). After being filtered through a 0.45 μm membrane, the solution was purified with RP-HPLC, wherein the reverse phase column was Luna C18, 250×25 mm, 5 nm, 100 Å, mobile phase A was 0.1% TFA/H$_2$O, and mobile phase B was 0.1% TFA/ACN. The desired product was eluted and collected with a gradient phase B from 38% to 68% at a flow rate of 20 mL/min over 60 min, (ESI-MS: 1595 ([M+4H] 4+)), and a purified precursor solution was obtained.

4. Saponification of $N^\alpha$—(HOOC(CH$_2$)$_{14}$CO)—$N^\epsilon$—(OCCH$_2$CH$_2$CO-(B28D-$N^{\epsilon B29}$-B30E Human Insulin))-Lys-OH Precursor Acetonitrile was removed from the purified precursor solution via vacuum concentration. Then the pH value of the solution was adjusted to 8.0 with 10% NaOH solution and an equal volume of 0.2M ice-cooled NaOH was added to start saponification. The saponified product was analyzed by RP-HPLC. After 50 min, the reaction was terminated by adding 10% HCl.

5. Purification and Lyophilization of Saponified $N^\alpha$—(HOOC(CH$_2$)$_{14}$CO)—$N^\epsilon$—(OCCH$_2$CH$_2$CO-(B28D-$N^{\epsilon B29}$-B30E Human Insulin))-Lys-OH Precursor Solution The above saponified precursor solution was diluted with acetonitrile to make the content of the organic phase about 30% (v:v). After being filtered through a 0.45 μm membrane, the solution was purified with RP-HPLC, wherein the reverse phase column was Luna C18, 250×25 mm, 5 μm, 100 Å, mobile phase A was 0.1% TFA/H$_2$O, and mobile phase B was 0.1% TFA/ACN. The desired product was eluted and collected with a gradient phase B from 35% to 65% at a flow rate of 20 mL/min over 60 min, and 4.0 mg of product (purity 94.5%) was obtained. The obtained product has the following structure:

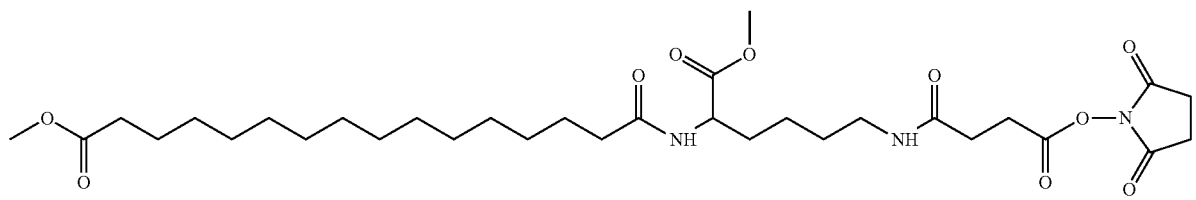 [SMILES: COC(=O)CCCCCCCCCCCCCCC(=O)NC(CCCCNC(=O)CCC(=O)ON1C(=O)CCC1=O)C(=O)OC]

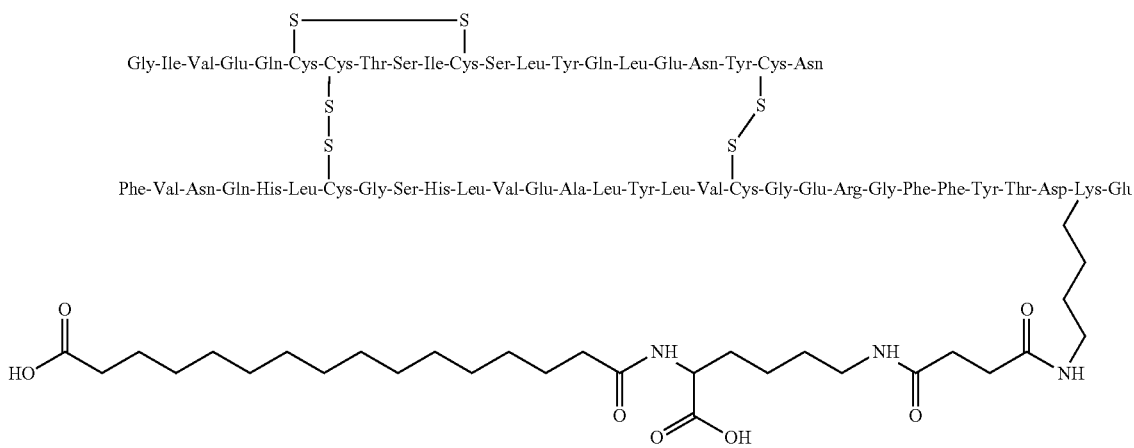

6. Confirmation of the Structure of $N^\alpha$—(HOOC(CH$_2$)$_{14}$CO)—$N^\epsilon$—(OCCH$_2$CH$_2$CO-(B28D-$N^{\epsilon B29}$-B30E Human Insulin))-Lys-OH The molecular weight of $N^\alpha$—(HOOC(CH$_2$)$_{14}$CO)—$N^\epsilon$—(OCCH$_2$CH$_2$CO-(B28D-$N^{\epsilon B29}$-B30E human insulin))-Lys-OH detected by ESI-MS was 6350.68, which is consistent with the theoretically predicted molecular weight of 6350.28.

$N^\alpha$—(HOOC(CH$_2$)$_{14}$CO)—$N^\alpha$—(OCCH$_2$CH$_2$CO-(B28D-$N^{\epsilon B29}$-B30E human insulin))-Lys-OH was digested with trypsin. The digested products were analyzed by LC-MS. The results showed the molecular weight of the two fragments F1 and F2 were 4865 and 1502, respectively, consistent with the theoretical molecular weight of the digested products. Fragment F2 corresponds to the modified B-chain fragment. Modified sites were proven to be the same as expected.

Example 17

Preparation of Human Insulin $N^{\epsilon B29}$—($N^\alpha$—(HOOC(CH$_2$)$_{14}$CO)-γ-Glu)-Des(B30) (HS060)

The preparation procedure of the present example was the same as that for the preparation of human insulin $N^{\epsilon B3}$—($N^\alpha$—(HOOC(CH$_2$)$_{14}$CO)-γ-Glu)-B29E-B30E, as described in Example 14, except that human insulin B(1-27)-D-K-E, A(1-21) (Sequence 6) used in Example 14 was replaced with recombinant human insulin Des (B30) (50 mg, 8.76 mmol) (Example 2).

The molecular weight of $N^{\epsilon B29}$—($N^\alpha$—(HOOC(CH$_2$)$_{14}$CO)-γ-Glu)-Des(B30) human insulin detected by ESI-MS was 6103.9, which is consistent with the theoretically predicted molecular weight of 6103.5.

Human insulin $N^{\epsilon B29}$—($N^\alpha$—(HOOC(CH$_2$)$_{14}$CO)-γ-Glu)-Des(B30) was digested with trypsin. The digested products were analyzed by LC-MS. The results showed the molecular weights of the two fragments F1 and F2 were 4865 and 1256, respectively, consistent with the theoretical molecular weight of the digested products. Fragment F2 corresponds to modified B-chain fragment. Modified sites were proven to be the same as expected. The resulting product has the following structure:

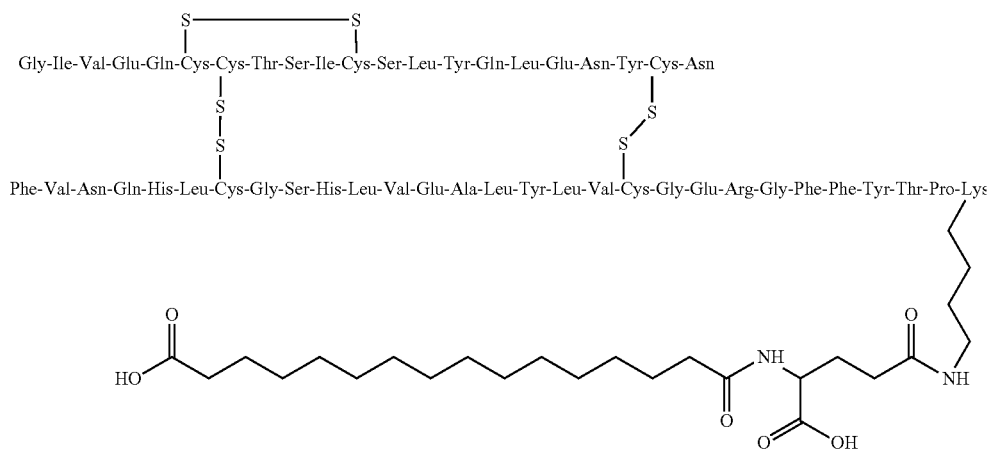

Example 18

Preparation of Human Insulin $N^{\epsilon B3}$—($N^{\alpha}$—(HOOC(CH$_2$)$_{14}$CO)-γ-Glu)-B29E-B30E (HS065)

The preparation procedure of the present example was the same as that for the preparation of $N^{\epsilon B3}$—($N^{\alpha}$—(HOOC(CH$_2$)$_{14}$CO)-γ-Glu)-B29E-B30E, as described in Example 14, except that human insulin B(1-27)-D-K-E, A(1-21) used in Example 14 was replaced with recombinant human insulin B(1-2)-K-B(4-28)-E-E, A(1-21) (27.2 mg, 4.65 mmol) (Example 6).

The molecular weight of human insulin $N^{\epsilon B29}$—($N^{\alpha}$—(HOOC(CH$_2$)$_{14}$CO)-γ-Glu)-B29E-B30E detected by ESI-MS was 6249, which is consistent with the theoretically predicted molecular weight of 6248.23.

Human insulin $N^{\epsilon B29}$—($N^{\alpha}$—(HOOC(CH$_2$)$_{14}$CO)-γ-Glu)-B29E-B30E was digested with trypsin. The digested products were analyzed by LC-MS. The results showed the molecular weights of the two fragments F1 and F2 were 5277.2 and 989, respectively, consistent with the theoretical molecular weight of the digested products. Fragment F1 corresponds to modified B-chain fragment. Modified sites were proven to be the same as expected. The resulting product has the structure as follows:

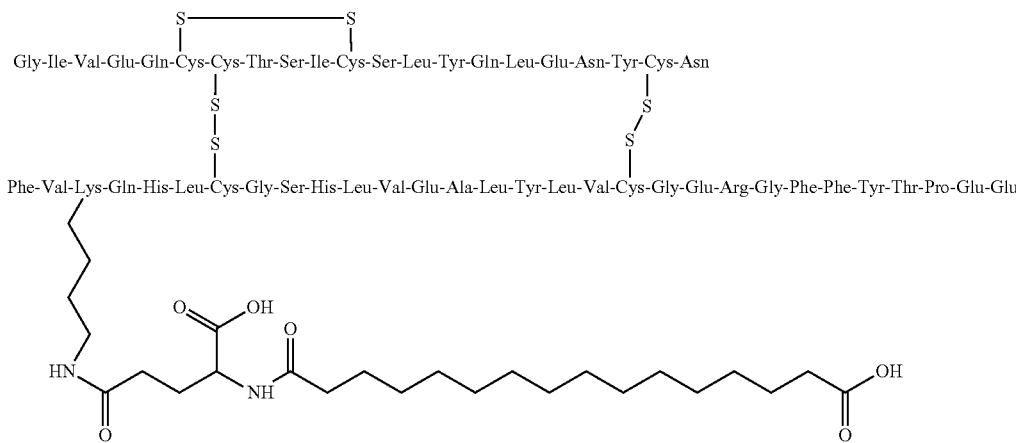

Example 19

Preparation of $N^{\alpha}$—(HOOC(CH$_2$)$_{14}$CO)—$N^{\epsilon}$—(OCCH$_2$CH$_2$CO—($N^{\epsilon B3}$-B29E-B30E Human Insulin))-Lys-OH (HS606)

The preparation procedure of the present example was the same as that for the preparation of $N^{\alpha}$—(HOOC(CH$_2$)$_{14}$CO)—$N^{\epsilon}$—(OCCH$_2$CH$_2$CO—($N^{\epsilon B3}$-B29E-B30E human insulin))-Lys-OH, as described in Example 16, except that human insulin B(1-27)-D-K-E, A(1-21) used in Example 16 was replaced with recombinant human insulin B(1-2)-K-B(4-28)-E-E, A(1-21) (25 mg, 4.27 mmol) (Example 6).

The molecular weight of $N^{\alpha}$—(HOOC(CH$_2$)$_{14}$CO)—$N^{\epsilon}$—(OCCH$_2$CH$_2$CO—($N^{\epsilon B3}$-B29E-B30E human insulin))-Lys-OH detected by ESI-MS was 6248, which is consistent with the theoretically predicted molecular weight of 6247.4.

$N^{\alpha}$—(HOOC(CH$_2$)$_{14}$CO)—$N^{\epsilon}$—(OCCH$_2$CH$_2$CO—($N^{\epsilon B3}$-B29E-B30E human insulin))-Lys-OH was digested with trypsin. The digested products were analyzed by LC-MS. The results showed the molecular weights of the two fragments F1 and F2 were 5376.3 and 989, respectively, consistent with the theoretical molecular weight of the digested products. Fragment F1 corresponds to modified B-chain fragment. Modified sites were proven to be the same as expected. The resulting product has the following structure:

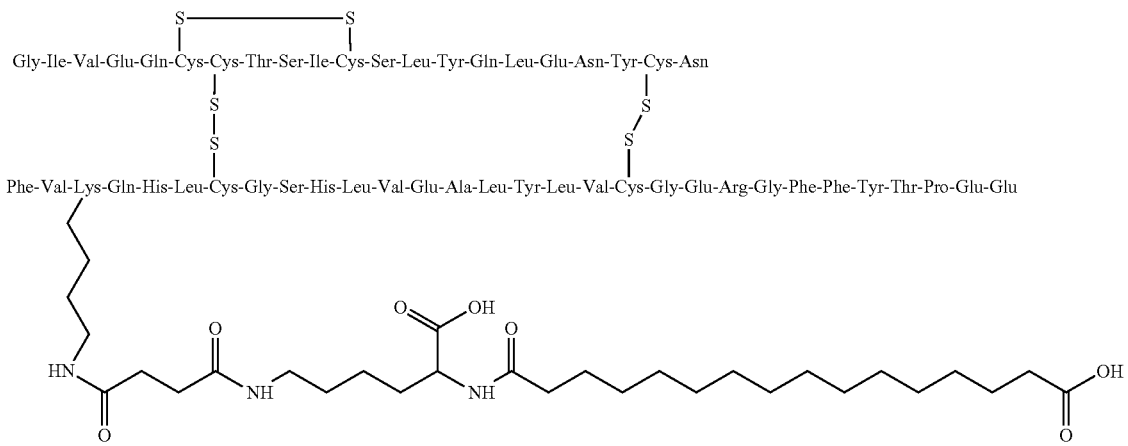

Example 20

Preparation of Human Insulin $N^{\epsilon B3}$—($N^{\alpha}$—(HOC(CH$_2$)$_{15}$CO)-γ-Glu)-B29E-B30E (HS607)

The preparation procedure of the present example was the same as that for the preparation of human insulin $N^{\epsilon B3}$—($N^{\alpha}$—(HOC(CH$_2$)$_{15}$CO)-γ-Glu)-B29E-B30E, as described in Example 15, except that human insulin B(1-27)-D-K-E, A(1-21) used in Example 15 was replaced with recombinant human insulin B(1-2)-K-B(4-28)-E-E, A(1-21) (27.2 mg, 4.65 mmol) (Example 6).

The molecular weight of human insulin $N^{\epsilon B3}$—($N^{\alpha}$—(HOC(CH$_2$)$_{15}$CO)-γ-Glu)-B29E-B30E detected by ESI-MS was 6236, which is consistent with the theoretically predicted molecular weight of 6234.3.

Human insulin $N^{\epsilon B3}$—($N^{\alpha}$—(HOC(CH$_2$)$_{15}$CO)-γ-Glu)-B29E-B30E was digested with trypsin. The digested products were analyzed by LC-MS. The results showed the molecular weights of the two fragments F1 and F2 were 5263.2 and 989, respectively, consistent with the theoretical molecular weight of the digested products. Fragment F1 corresponds to modified B-chain fragment. Modified sites were proven to be the same as expected. The resulting product has the following structure:

Example 21

Preparation of Human Insulin $N^{\epsilon B3}$—($N^{\alpha}$—(HOOC(CH$_2$)$_{14}$CO)-γ-Glu)-B29E-B30E, A21G (HS608)

The preparation procedure of the present example was the same as that for the preparation of $N^{\epsilon B3}$—($N^{\alpha}$—(HOOC(CH$_2$)$_{14}$CO)-γ-Glu)-B29E-B30E, A21G, as described in Example 14, except that human insulin B(1-27)-D-K-E, A(1-21) used in Example 14 was replaced with recombinant human insulin B(1-2)-K-B(4-28)-E-E, A(1-20)-G (24.3 mg, 4.19 mmol) (Example 12).

The molecular weight of human insulin $N^{\epsilon B3}$—($N^{\alpha}$—(HOOC(CH$_2$)$_{14}$CO)-γ-Glu)-B29E-B30E, A21G detected by ESI-MS was 6192.5, which is consistent with the theoretically predicted molecular weight of 6190.5.

Human insulin $N^{\epsilon B3}$—($N^{\alpha}$—(HOOC(CH$_2$)$_{14}$CO)-γ-Glu)-B29E-B30E, A21G was digested with trypsin. The digested products were analyzed by LC-MS. The results showed the molecular weights of the two fragments F1 and F2 were 5219.5 and 989, respectively, consistent with the theoretical molecular weight of the digested products. Fragment F1 corresponds to modified B-chain fragment. Modified sites were proven to be the same as expected. The resulting product has the following structure:

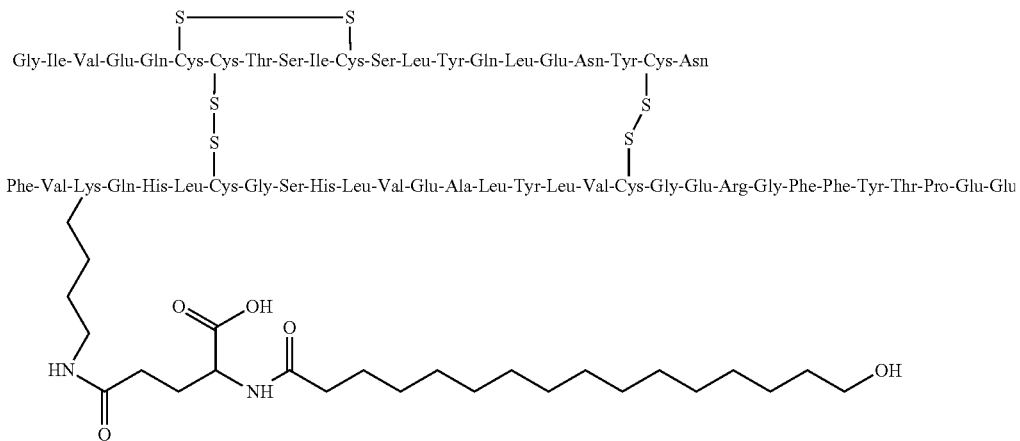

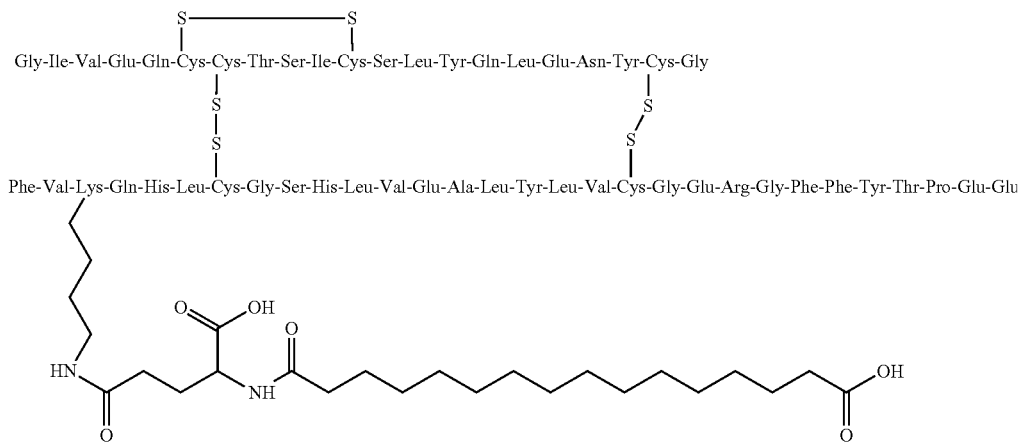

Example 22

Preparation of $N^\alpha$—(HOOC(CH$_2$)$_{14}$CO)—$N^\epsilon$—(OCCH$_2$CH$_2$CO—($N^{\epsilon B3}$-B29E-B30E, A21G Human Insulin))-Lys-OH (HS609)

The preparation procedure of the present example was the same as that for the preparation of $N^\alpha$—(HOOC(CH$_2$)$_{14}$CO)—$N^\epsilon$—(OCCH$_2$CH$_2$CO—($N^{\epsilon B3}$-B29E-B30E, A21G human insulin))-Lys-OH as described in Example 16, except that human insulin B(1-27)-D-K-E, A(1-21) used in Example 16 was replaced with human insulin B(1-2)-K-B(4-28)-E-E, A(1-20)-G (24.1 mg, 4.16 mmol) (Example 12).

The molecular weight of $N^\alpha$—(HOOC(CH$_2$)$_{14}$CO)—$N^\epsilon$—(OCCH$_2$CH$_2$CO—($N^{\epsilon B3}$-B29E-B30E, A21G human insulin))-Lys-OH detected by ESI-MS was 6289, which is consistent with the theoretically predicted molecular weight of 6289.6.

$N^\alpha$—(HOOC(CH$_2$)$_{14}$CO)—$N^\epsilon$—(OCCH$_2$CH$_2$CO—($N^{\epsilon B3}$-B29E-B30E, A21G human insulin))-Lys-OH was digested with trypsin. The digested products were analyzed by LC-MS. The results showed the molecular weights of the two fragments F1 and F2 were 5318.5 and 989, respectively, consistent with the theoretical molecular weight of the digested products. Fragment F1 corresponds to the modified B-chain fragment. Modified sites were proven to be the same as expected. The resulting product has the following structure:

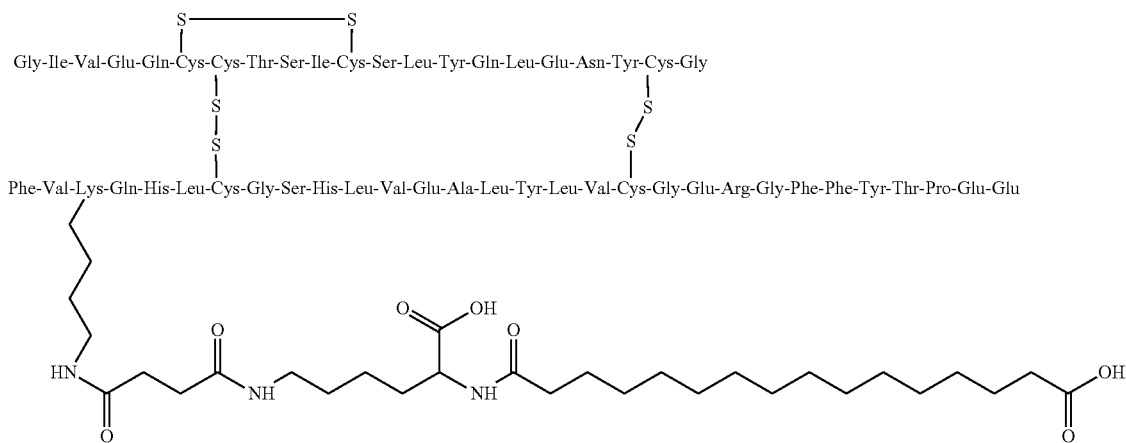

Example 23

Preparation of Human Insulin $N^{\epsilon B3}$—($N^\alpha$—(HOC(CH$_2$)$_{15}$CO)-γ-Glu)-B29E-B30E, A21G (HS610)

The preparation procedure of the present example was the same as that for the preparation of human insulin $N^{\epsilon B3}$—($N^\alpha$—(HOC(CH$_2$)$_{15}$CO)-γ-Glu)-B29E-B30E, A21G as described in Example 15, except that human insulin B(1-27)-D-K-E, A(1-21) used in Example 15 was replaced with recombinant human insulin B(1-2)-K-B(4-28)-E-E, A(1-20)-G (24.8 mg, 4.28 mmol) (Example 12).

The molecular weight of human insulin $N^{\epsilon B3}$—($N^\alpha$—(HOC(CH$_2$)$_{15}$CO)-γ-Glu)-B29E-B30E, A21G detected by ESI-MS was 6177, which is consistent with the theoretically predicted molecular weight of 6176.5.

Human insulin $N^{\epsilon B3}$—$(N^\alpha$—$(HOC(CH_2)_{15}CO)$-γ-Glu)-B29E-B30E, A21G was digested with trypsin. The digested products were analyzed by LC-MS. The results showed the molecular weights of the two fragments F1 and F2 were 5205.4 and 989, respectively, consistent with the theoretical molecular weight of the digested products. Fragment F1 corresponds to the modified B-chain fragment. Modified sites were proven to be the same as expected. The resulting product has the following structure:

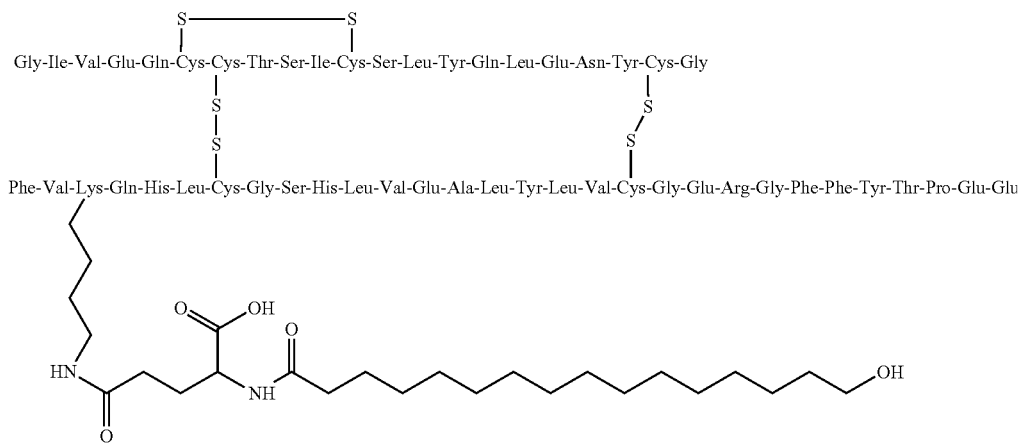

Example 24

Preparation of PEGylated (20 KD)-Insulin

1. Pegylation (20 KD) of Insulin B(1-27)-D-K-E, A(1-21)

50 mg of insulin B(1-27)-D-K-E, A(1-21) were dissolved in 25 ml of water, and the pH value was adjusted to 11.40 with 1.0M $Na_2CO_3$. Then, 500 mg of m-PEG-OSu solution were slowly added (m-PEG-OSu was dissolved in a mixed solvent having 10 ml acetonitrile and 6 ml THF), and the reaction solution was stirred at room temperature for 2 hrs. Then, the pH value of the reaction system was adjusted to 6.0 with 0.1M HCl to quench the reaction, and the organic solvent was removed under reduced pressure. The reaction was terminated, and purification was performed by using a GE SP-Sepharose cation exchange gel. The final reaction product was diluted 10-fold with solution A (solution A, 20 mM Gly pH3.0; solution B, 20 mM Gly pH3.0, 1M NaCl) and loaded. The column was equilibrated with solution A in 5 volumes, and eluted in a linear gradient from 0 to 100% B for 20 column volumes. Eluted peaks were collected, then desalted and concentrated in a 10 kD entrapped ultrafiltration tube, the desired product was obtained, referred as PEG (20 kD)–156.

2. Identification of the PEG (20 kD) Modified Position of Insulin B(1-27)-D-K-E, A(1-21)

Before and after PEGylation, the insulin B(1-27)-D-K-E, A(1-21) and PEGylated B(1-27)-D-K-E, A(1-21) were digested with GLu-C, respectively, and subjected to LC-MS analysis. The digested products are as follows:

| F-I | F-II | F-III | F-IV |
|---|---|---|---|
| GIVE | QCCTSICSLYQLE FVNQHLCGSHLVE | NYCN ALYLVCGE | RGFFYTDKE |

The enzymatically digested products were compared via HPLC analysis. It was found that enzymatically digested fragments F-I, F-II and F-III were not altered before and after enzymatic digestion, whereas the hydrophobicity of F-IV fragment, which was obtained from enzymatically digested PEGylated insulin B(1-27)-D-K-E, A(1-21) was dramatically increased. Such data demonstrated that the PEGylated position was on B29K, the structure of which is as follows:

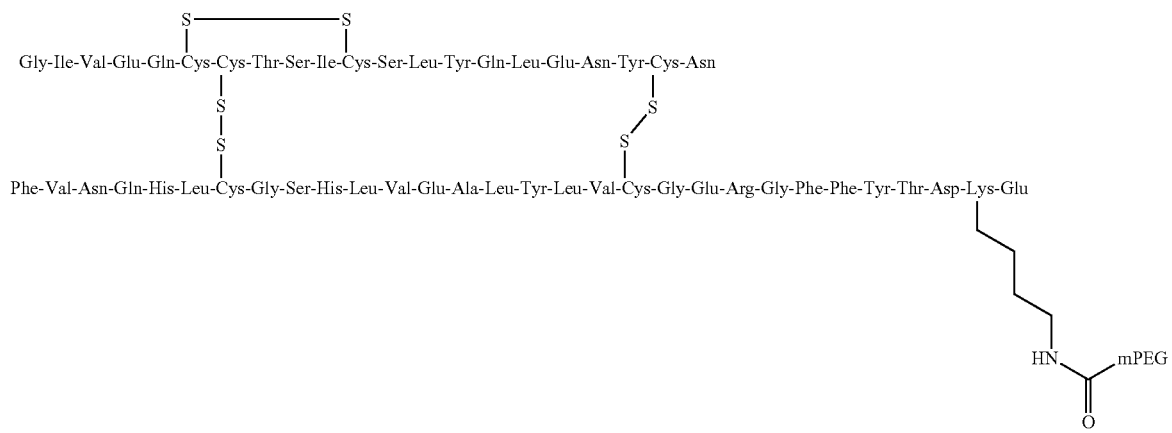

3. PEGylated insulin B(1-2)-K-B(4-28)-E-E, A(1-21) was prepared as described in the above Step 1, the target product was obtained, referred as PEG (20 KD)-107. The resulting product was identified using the method shown in Step 2, and DTT (10 mM) was used for reduction of the obtained product. No change was detected in the A-chain. Hydrophobicity of the B-chain was greatly increased. The data demonstrated that the modified position is on position B3K. The molecular structure of the modified product obtained was as follows:

Gly pH3.0; solution B, 20 mM Gly pH3.0, 1M NaCl) and loaded. The column was equilibrated with solution A in 5 volumes, and eluted in a linear gradient from 0 to 100% B for 20 column volumes. Eluted peaks were collected, then desalted and concentrated in a 10 kD entrapped ultrafiltration tube, and the desired product was obtained, referred to as PEG (30 KD)-156.

2. Identification of the PEG (30 kD) Modified Position of Insulin B(1-27)-D-K-E, A(1-21)

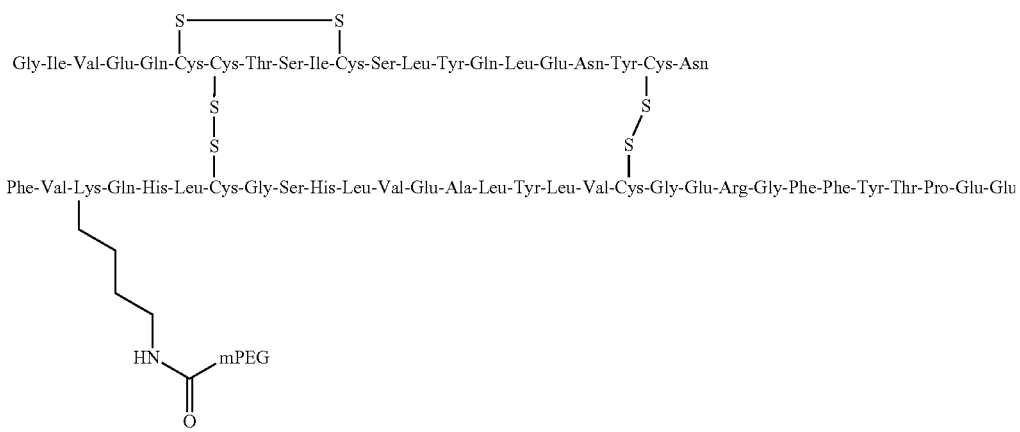

Example 25

Preparation of PEGylated (30 kD)-Insulin

1. PEGylation (30 kD) of Insulin B(1-27)-D-K-E, A(1-21)

50 mg of insulin B(1-27)-D-K-E, A(1-21) were dissolved in 25 mL of water, the pH value was adjusted to 11.40 with 1.0M $Na_2CO_3$, then 750 mg of m-PEG-OSu(30K) solution (m-PEG-OSu was dissolved in a mixed solvent of 10 ml acetonitrile and 6 ml THF) was added slowly, and the reaction solution was stirred at room temperature for 2 hrs. Then the pH value of the reaction system was adjusted to 6.0 with 0.1M HCl to quench the reaction, and the organic solvent was removed under reduced pressure. The reaction was terminated, and purification was performed by GE SP-Sepharose cation exchange gel. The final reaction product was diluted 10-fold with solution A (solution A, 20 mM Before and after PEGylation, the insulin B(1-27)-D-K-E, A(1-21) and PEGylated B(1-27)-D-K-E, A(1-21) were digested with GLu-C, respectively. The digested products were as follows:

| F-I | F-II | F-III | F-IV |
|---|---|---|---|
| GIVE | QCCTSICSLYQLE FVNQHLCGSHLVE | NYCN ALYLVCGE | RGFFYTDKE |

Each digested product was analyzed by HPLC. The results showed that no change was detected in fragments FI, F-II and F-III before and after PEGylation. However, hydrophobicity of digested product fragment F-IV significantly increased. The data demonstrated that the PEGylation position is on B29K, the structure of which is as follows:

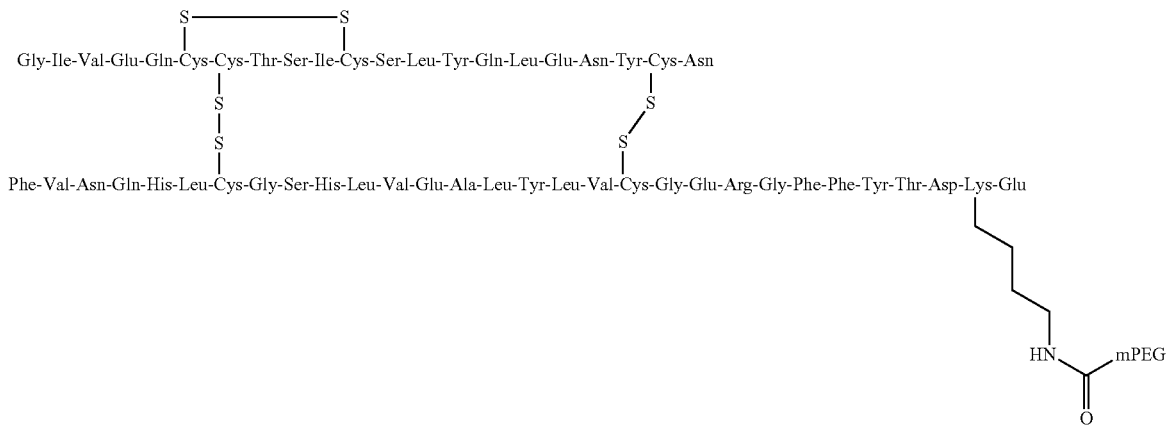

3. PEGylated (30 kD) insulin B(1-2)-K-B(4-28)-E-E, A(1-21) was prepared as described in above Step 1, and the target product was obtained, referred to as PEG (30 kD)-107. The resulting product was identified using the method shown in Step 2, and DTT (10 mM) was used for reduction of the obtained product. No change was detected in the A-chain. Hydrophobicity of the B-chain was greatly increased. It was demonstrated that the modified position was on position B3K. The molecular structure of the modified product obtained was as follows:

mM Gly pH3.0; solution B, 20 mM Gly pH3.0, 1M NaCl), and loaded, the column was equilibrated with solution A in 5 volumes, and eluted in a linear gradient from 0 to 100% B for 20 column volumes. Eluted peaks were collected, then desalted and concentrated in a 10 kD entrapped ultrafiltration tube, and the desired product was obtained, referred as PEG (40 kD)-156.

2. Identification of the PEG (40 kD) Modified Position of Insulin B(1-27)-D-K-E, A(1-21)

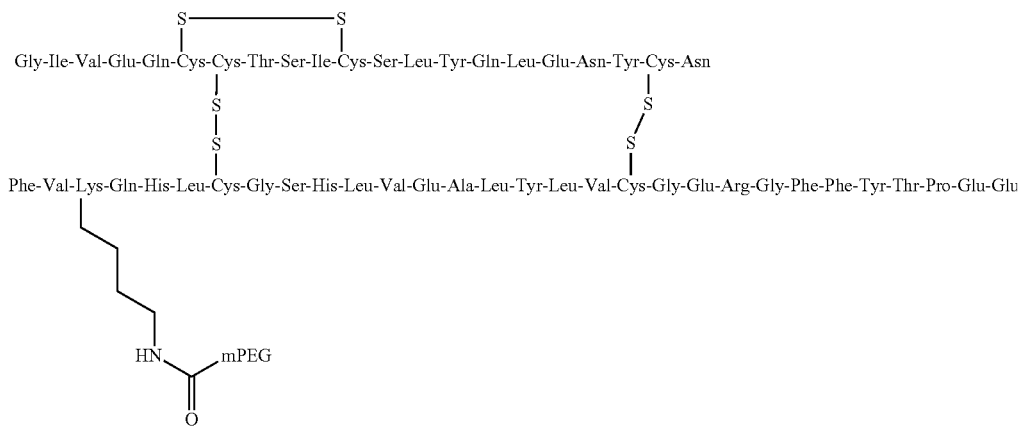

Example 26

Preparation of PEGylated (Branched 40 kD) Insulin

1. PEGylation (40 kD) of Insulin B(1-27)-D-K-E, A(1-21))

50 mg of B(1-27)-D-K-E, A(1-21) insulin was dissolved in 25 ml of water, and the pH value of the solution was adjusted to 11.40 with 1.0M $Na_2CO_3$. Then 1000 mg of m-PEG-OSu(40K) solution (m-PEG-OSu was dissolved in mixed solvent of 10 ml acetonitrile and 6 ml THF) was added slowly, and the reaction was stirred at room temperature for 2 hrs. Then the pH value of the reaction system was adjusted to 6.0 with 0.1M HCl to quench the reaction, and the organic solvent was removed under reduced pressure. The reaction was terminated and purification was performed by GE SP-Sepharose cation exchange gel. The final reaction product was diluted 10-fold with solution A (solution A, 20

Before and after PEGylation, the insulin B(1-27)-D-K-E, A(1-21) and PEGylated B(1-27)-D-K-E, A(1-21) were digested with GLu-C, respectively. The digested products were as follows:

| F-I | F-II | F-III | F-IV |
|-----|------|-------|------|
| GIVE | QCCTSICSLYQLE FVNQHLCGSHLVE | NYCN ALYLVCGE | RGFFYTDKE |

Digested products were analyzed by HPLC. The results showed that no change in fragments FI, F-II and F-III were detected before and after PEGylation. However, hydrophobicity of digested product fragment F-IV significantly increased. The data demonstrated that the PEGylated site was on B29K, the structure of which is as follows:

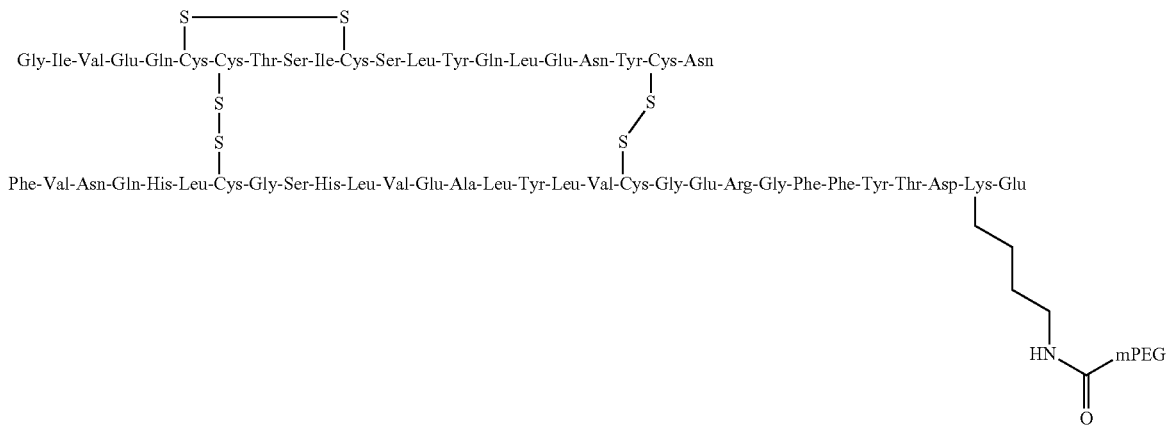

3. PEGylated (40 kD) insulin B(1-2)-K-B(4-28)-E-E, A(1-21) was prepared as described in above Step 1, and the target product was obtained, referred to as PEG (40 kd)-107. The resulting product was identified using the method shown in Step 2, and DTT (10 mM) was used for reduction of the product. No change was detected in the A-chain. Hydrophobicity of the B-chain was greatly increased. It confirmed that the modified position was on B3K. The molecular structure of the modified product obtained was as follows:

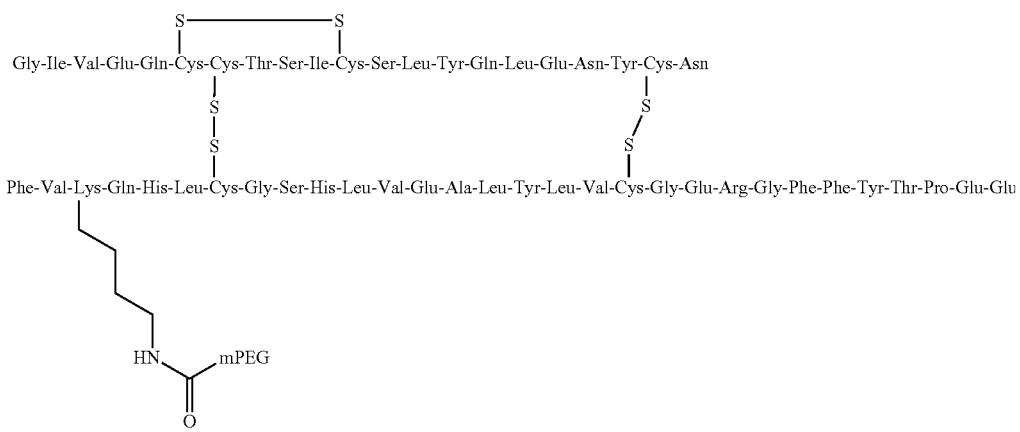

BIOLOGICAL ASSAYS

Test Example 1

Binding Assay of Human Insulin Analogue to the Insulin Receptor (IR) or Insulin-Like Growth Factor Receptor 1 (IGF1-R)

The relative binding affinity of human insulin analogue according to the present invention to the insulin receptor or insulin-like growth factor receptor 1 was detected by competitive receptor binding assay.

Membranes expressing insulin receptor and insulin-like growth factor-1 receptor were extracted from IM-9 and H19-7 cells (ATCC). $5 \times 10^8$ cells were collected, washed with PBS and resuspended in lysis buffer (50 mM Tris-HCl, pH7.8, 150 mM NaCl, protease inhibitors (Roche)) to a cell density of $6 \times 10^7$ cells/mL. Samples were placed on ice. Samples were homogenized by an electric homogenizer at 25000 rpm for sec twice, then centrifuged at low speed (2000 g, 15 min), and the supernatant was collected. Precipitated fraction was resuspended in an appropriate amount of the lysis buffer. The above step was repeated three times and the supernatant from each time was pooled. The pooled supernatant was centrifuged at high speed (4° C., 35000 rpm, 60 min), then the resulting supernatant was discarded, the precipitated fraction was resuspended in an appropriate amount of the cell lysis buffer, and experimental membrane proteins were obtained. Membrane protein extracted from the IM-9 cell was insulin receptor, referred to as IM-9 cell membrane protein. Membrane protein extracted from H19-7 cell was insulin-like growth factor-1 receptor, referred to as H19-7 cell membrane proteins. The protein concentration was quantified by the Bradford method.

In the insulin receptor binding experiment, to each well of a 96-well plate 40 μL of 125 pM [$^{125}$I] isotope insulin (Perkin Elmer, Cat. No 420010UC), 3 μg of IM-9 cell membrane protein (50 μL), and 10 μL gradient dilutions of human insulin analogues to be tested were added. All of the above solutions were prepared in a reaction solution (50 mM Tris-HCl, pH7.8, 150 mM NaCl, 0.1% BSA). The above mixture was gently stirred at room temperature for 1 hr. Incubated membrane proteins were collected by FilterMate Havester (Perkin Elmer, Cat No S/N: DA12073369) to the membrane of MicroBeta Filtermat B (Perkin Elmer, Cat No 1450-521), which was pre-wetted with 0.3% PEI, then washed with the reaction solution three times and dried in an oven at 60° C. for 1 hr. The dried filter membrane was put into a good seal membrane, added with 15 mL of scintillation fluid, and sealed. Finally, the result was read by Microbeta Plate Counter (Perkin Elmer, Cat. No. 1450).

In insulin-like growth factor-1 receptor binding experiments, 40 μL of 125 pM [$^{125}$I] isotope IGF-1, 9 μg of H19-7 cell membrane protein (50 μL), and 10 μL gradient dilutions of human insulin analogues to be tested were added to each well of a 96 well-plate. The remaining steps were the same as those in insulin receptor binding experiments.

Data obtained in the above experiments were nonlinear fitted using Graphpad Prism. $IC_{50}$ values (nM) were obtained in competitive binding experiments of human insulin analogues to insulin receptor or insulin-like growth factor-1 receptor. The results are shown in the table below.

TABLE 1

Binding assay for insulin and analogues thereof to the insulin receptor (IR) or insulin-like growth factor receptor 1 (IGF1-R)

| Sequence NO | Example | Human insulin abbreviation | IR | IGF1-R |
|---|---|---|---|---|
| hI | 1 | B(1-30), A(1-21) | 0.46 | 316.5 |
| Des(B30)-hI | 2 | B(1-29), A(1-21) | 0.92 | 134.5 |
| 5 | 6 | B(1-2)-K-B(4-28)-E-E, A(1-21) | 0.45 | 1058 |
| 6 | 7 | B(1-27)-D-K-E, A(1-21) | 0.19 | 120.9 |
| 13 | 12 | B(1-2)-K-B(4-28)-E-E, A(1-20)-G | 0.24 | >2000 |

Note:
hI, human insulin andDes (B30)-hI, human insulin lacking B30, were both used as positive control.

The data demonstrated that insulin analogues of the present invention have comparative binding affinity as positive controls, wherein the binding affinity of B(1-2)-K-B(4-28)-E-E, A(1-20)-G with IR is 1.9-fold as potent as that of positive control (hI), and its affinity to IGF1-R is decreased to one-tenth lower than that of hI.

Test Example 2

In Vivo Activity Evaluation of Human Insulin Analogues

1. ICR male mice used in this experiment were purchased from SINO-BRITSH SIPPR/BK LAB. ANIMAL LTD., CO, 18-20 g. Mice were fed three days in a laboratory environment, with a temperature of 20-25° C. and humidity of 40-60%.

2. The drug used in this experiment, Humulin R (Lilly Egypt, HRE046. 100 IU/mL), was formulated to 1 IU/mL with 0.05N HCl (0.05 mg/kg), then diluted with 0.9% NaCl to solutions in concentrations of 0, 0.01, 0.02, 0.04, 0.08, 0.16, 0.32, 0.64 IU/mL.

3. 40 male mice were fasted for 16 hrs before this experiment. In the beginning, these mice were weighed and the basic blood glucose levels were measured (cut off the tails and the blood glucose levels were detected by using Roche Glucometer and the corresponding test strips, similarly hereafter). On the basis of blood glucose values, mice were randomly divided into eight groups, with five mice per group. The administration dosages to each group were as follows: 0, 0.1, 0.2, 0.4, 0.8, 1.6, 3.2 IU/kg (administration volume was 100 μL per 20 g body weight).

4. Blood glucose level (mmol/L) of each mouse was determined at 1 hr after administration.

5. Data analysis: The measured blood glucose level was expressed as a percentage of the blood glucose level before administration. Drug reaction (hypoglycemic) curves were plotted with Graphpad Prism 5, and an $ED_{50}$ value (IU/kg or mg/kg) was obtained. $ED_{50}$ value means the dosage of drug for subcutaneous injection required for reaching 50% of maximum hypoglycemic effect.

6. $ED_{50}$ values of insulin analogues are shown in the table below:

TABLE 2

In vivo activity assay of human insulin analogues

| Sequence NO | Corresponding example | Human insulin abbreviation | relative activity |
|---|---|---|---|
| hI | 1 | B(1-30), A(1-21) | 1.11 |
| Des(B30)-hI | 2 | B(1-29), A(1-21) | 1.00 |
| 1 | 1 | B(1-29), R-A(1-21) | 0.96 |
| 2 | 3 | B(1-27)-K-E-R, A(1-21) | 1.29 |
| 3 | 4 | B(1-27)-K-E, A(1-21) | 0.81 |
| 4 | 5 | B(1-27)-K-P-E, A(1-21) | 0.81 |
| 5 | 6 | B(1-2)-K-B(4-28)-E-E, A(1-21) | 1.53 |
| 6 | 7 | B(1-27)-D-K-E, A(1-21) | 1.61 |
| 9 | 9 | B(1-2)-K-B(4-28)-E-R, A(1-21) | 1.47 |
| 11 | 10 | B(1-2)-D-B(4-29), R-A(1-21) | 1.46 |
| 12 | 11 | B(1-27)-K-E, A(1-20)-G | 0.90 |
| 13 | 12 | B(1-2)-K-B(4-28)-E-E, A(1-20)-G | 1.64 |
| 14 | 13 | B(1-2)-D-B(4-29)-R, A(1-20)-G | 1.09 |
| 15 | 13 | B(1-2)-D-B(4-29), A(1-20)-G | 1.48 |
| 16 | 13 | B(1-2)-D-B(4-29), R-A(1-20)-G | 0.91 |
| 17 | 7 | B(1-27)-D-K-E, A(1-20)-G | 1.34 |

Note:
The relative activity refers to ratio of $ED_{50}$ value of human insulin analogue versus $ED_{50}$ value of Des (B30)-hI. Des(B30)-hI was used as a control for each experiment, and the $ED_{50}$ value of Des(B30)-hI was set to 1.

These above results indicated that the in vivo activity of human insulin analogues according to the present invention was comparable to that of the positive control. In vivo activity of some human insulin analogues, such as B(1-2)-K-B(4-28)-E-E, A(1-20)-G, was increased by more than 50% compared with hI (human insulin) or Des (B30)-hI (human insulin lacking B30), and was significantly superior to the positive control.

Test Example 3

In Vivo Long-Acting Activity Assay of Insulin Derivatives

Sprague-Dawley (SD) rats, male, used in this experiment were purchased from SINO-BRITSH SIPPR/BK LAB. ANIMAL LTD., CO, License number: SCXK (Shanghai) 2008-0016, 18-20 g. The rats were fed in an environment of SPF level. ICR male mice were fed three days in a laboratory environment, at temperature of 20-25° C., and humidity of 40-60%. The mice were fasted for 8 hrs before the experiment. 100 mg/kg STZ was intraperitoneally injected to establish rat models sufferring from diabetes. Two days later, fasting blood glucose values were measured. Rats, whose blood glucose values were greater than 11.1 mmol/L, were considered as rats sufferring from diabetes. At the beginning of the experiment, rats were weigh, and the blood glucose levels were measured (cut off tails and the blood glucose levels were detected by using Roche Glucometer and the corresponding test strips, similarly hereafter). On the basis of blood glucose values, rats were randomly divided into groups, 43 rats per group. The drug to be used was prepared in required concentrations. After subcutaneous injection of drugs, blood glucose levels were measured at multiple time points. IP (Index of Prolongation) was calculated according to blood glucose level.

Positive Control:

1. Humulin R: a Recombinant human insulin injection purchased from Lilly.

2. Detemir: a detemir insulin injection purchased from Novo Nordisk.

3. HS060 is Degludec, a molecule in phase III clinical trial of Novo Nordisk, human insulin $N^{\epsilon B29}$—($N^{\alpha}$—(HOOC$(CH_2)_{14}$CO)-γ-Glu)-Des(B30), see Example 17.

Compounds to be tested were insulin derivatives of the acylated human insulin analogues, indicated as follows:

1. HS061, B28D-$N^{\epsilon B29}$—($N^{\alpha}$—(HOOC$(CH_2)_{14}$CO)-γ-Glu)-B30E, see Example 14.

2. HS062, B28D-$N^{\epsilon B29}$—($N^{\alpha}$—(HO$(CH_2)_{15}$CO)-γ-Glu)-B30E, see Example 15.

3. HS067, $N^{\alpha}$—(HOOC$(CH_2)_{14}$CO)—$N^{\epsilon}$—(OCCH$_2$CH$_2$CO-(B28D-$N^{\epsilon B29}$-B30E human insulin))-Lys-OH, see Example 16.

The results shown in Table 3 demonstrate that the long-acting activities of HS061 (IP: 117.9), HS062 (IP: 112.3), HS067 (IP: 132.9) are all better than that of Detemir (IP: 100) and HS060 (IP: 105.9) (both are controls). Specifically, HS067 maintained basic blood glucose level up to 12 hrs in this model (results are shown in FIG. 5).

TABLE 3

Results of in vivo long-lasting activities of HS060, HS061, HS062 and HS067

| | | | | | group | | | |
|---|---|---|---|---|---|---|---|---|
| | | control | Humulin R | Detemir | HS060 | HS061 | HS062 | HS067 |
| dosage (mg/kg) | | 0 | 0.04 | 0.2 | 0.1 | 0.1 | 0.1 | 0.1 |
| animal | | 3 | 3 | 3 | 3 | 3 | 3 | 3 |
| Weight (g) | | 193 ± 17.0 | 172 ± 7.4 | 186 ± 9.0 | 183 ± 11.2 | 183 ± 12.6 | 200 ± 14.1 | 191 ± 9.0 |
| AOC | | | 21.0 | 69.2 | 76.9 | 74.4 | 65.4 | 57.5 |
| IP | | | 0 | 100 | 105.9 | 117.9 | 112.3 | 132.9 |
| Blood glucose | 0 h | 100.00 | 100.00 | 100.00 | 100.00 | 100.00 | 100.00 | 100.00 |
| level (%) | 0.5 h | 100.00 | 58.65 | 72.21 | 105.83 | 100.16 | 116.28 | 132.78 |
| | 1 h | 100.00 | 34.12 | 35.57 | 33.24 | 77.25 | 77.15 | 108.07 |
| | 2 h | 100.00 | 23.83 | 14.45 | 16.71 | 23.94 | 21.37 | 76.69 |
| | 4 h | 100.00 | 66.89 | 16.32 | 13.01 | 12.54 | 18.06 | 22.72 |
| | 6 h | 100.00 | 93.29 | 23.80 | 11.20 | 8.89 | 23.16 | 18.27 |
| | 8 h | 100.00 | 107.72 | 34.77 | 20.82 | 12.48 | 29.75 | 22.43 |
| | 10 h | 100.00 | 134.46 | 51.42 | 32.85 | 25.16 | 45.34 | 25.33 |
| | 12 h | 100.00 | 106.64 | 39.68 | 40.85 | 41.51 | 58.35 | 21.84 |
| | 14 h | 100.00 | 109.79 | 58.06 | 55.11 | 55.36 | 71.81 | 30.36 |
| | 16 h | 100.00 | 113.82 | 74.84 | 73.35 | 70.05 | 106.55 | 41.82 |
| | 18 h | 100.00 | 112.82 | 91.67 | 86.46 | 85.21 | 122.73 | 54.38 |
| | 20 h | 100.00 | 106.38 | 99.05 | 95.47 | 87.27 | 129.23 | 56.30 |

Test Example 4

Binding Assay of PEGylated Insulin to Insulin Receptor (IR)

1. The test method was the same as described in Test Example 1.
2. Compounds to be tested:
PEGylated (20 kD) insulin: PEG (20 kD)-107 represents the PEGylated insulin B(1-2)-K-B(4-28)-E-E, A(1-21), wherein the molecular weight of PEG is 20 kD; PEG (20 kD)-156 represents PEGylated insulin B(1-27)-D-K-E, A(1-21), wherein the molecular weight of PEG is 20 kD. Particularly, see Example 24.
3. In competitive binding assay, $IC_{50}$ values (nM) of PEGylated (20 kD) insulin binding to insulin receptor are shown in Table 4. It shows that the preferred sequence according to this invention can still bind to insulin receptor (IR) after PEGylation.

TABLE 4

Binding assay of PEGylated insulin to insulin receptor (IR)

| Sequence NO | Corresponding example | Human insulin abbreviation | IR(nM) |
|---|---|---|---|
| 6 | 24 | PEG (20KD) -107 | 18.8 |
| 5 | 24 | PEG (20KD) -156 | 71.8 |

Test Example 5

In Vivo Long-Acting Activity Assay of PEGylated Insulin

1. Test methods were the same as described in Test Example 3.
2. Compounds to be tested:
1). PEGylated (20 kD) insulin: PEG (20 kD)-107 represents the PEGylated insulin B(1-2)-K-B(4-28)-E-E, A(1-21), wherein molecular weight of PEG is 20 kD; PEG (20 kD)-156 represents PEGylated (20 kD)insulin B(1-27)-D-K-E, A(1-21). Particularly, see Example 24.

2). PEGylated (30 kD) insulin: PEG (30 kD)-107 represents the PEGylated (30 kD) insulin B(1-2)-K-B(4-28)-E-E, A(1-21); PEG(30 kD)-156 represents PEGylated insulin (k) B(1-27)-D-K-E, A(1-21). Particularly, see Example 25.

3). PEG (40 kD) insulin: PEG (40 kD)-107 represents the PEGylated (branched 40 kD) insulin B(1-2)-K-B(4-28)-E-E, A(1-21); PEG(40 kD)-156 represents PEGylated (branched 40 kD) insulin B(1-27)-D-K-E, A(1-21). Particularly see Example 26.

3. Test Results

1). Results of in vivo evaluation for long-acting activity of PEGylated (20 kD) insulin were shown in the following Table 5 and FIG. 6.

TABLE 5

Results of in vivo evaluation for long-acting activity of PEGylated (20 kD) insulin B(1-27)-D-K-E, A(1-21) and B(1-2)-K-B(4-28)-E-E, A(1-21)

| | | | group | | | |
|---|---|---|---|---|---|---|
| | | control | Humulin R | Detemir | PEG (20 kD)-107 | PEG (20 kD)-156 |
| Dosage (mg/kg) | | 0 | 0.04 | 0.2 | 0.1 | 0.1 |
| Numbers of Animals | | 4 | 4 | 4 | 4 | 4 |
| Weight (g) | | 136 | 139 | 130 | 137 | 139 |
| AOC % | | | 5.25 | 7.39 | 51.27 | 51.71 |
| IP | | | 0 | 100 | 207.36 | 204.26 |
| Blood | 0 h | 100 | 100 | 100 | 100 | 100 |
| glucose | 1 h | 100 | 45.94 | 96.63 | 109.43 | 101.39 |
| value (%) | 2 h | 100 | 25.26 | 57.24 | 106.92 | 91.03 |
| | 4 h | 100 | 58.85 | 32.49 | 105.73 | 58.14 |
| | 6 h | 100 | 86.49 | 40.98 | 73.21 | 27.32 |
| | 8 h | 100 | 138.71 | 86.94 | 43 | 16.52 |
| | 10 h | 100 | 152.95 | 112.66 | 25.48 | 16.14 |
| | 12 h | 100 | 151.89 | 127.52 | 23.81 | 16.06 |
| | 24 h | 100 | | | 19.09 | 24.21 |
| | 28 h | 100 | | | 23.19 | 30.5 |

TABLE 5-continued

Results of in vivo evaluation for long-acting activity of PEGylated (20 kD) insulin B(1-27)-D-K-E, A(1-21) and B(1-2)-K-B(4-28)-E-E, A(1-21)

| | | group | | | |
|---|---|---|---|---|---|
| | control | Humulin R | Detemir | PEG (20 kD)-107 | PEG (20 kD)-156 |
| 32 h | 100 | | | 30.82 | 33.49 |
| 34 h | 100 | | | 39.89 | 46.34 |
| 36 h | 100 | | | 55.94 | 64.5 |
| 46 h | 100 | | | 64.89 | 87.17 |
| 48 h | 100 | | | 103.59 | 113.56 |
| 50 h | 100 | | | 113.66 | 113.64 |
| 52 h | 100 | | | 133.77 | 129.0b7 |
| 54 h | 100 | | | 148.74 | 144.42 |
| 56 h | 100 | | | 153.91 | 149.59 |

Conclusion:
The results in Table 5 show that the PEG (20 kD)-107 and PEG (20 kD)-156 maintained stable blood glucose level for up to 32-46 hrs, see FIG. 6. IP (Index of Prolongation) of the two were approximately 207.36 and 204.26, respectively (see Table 5), which were significantly better than that of the positive control.

2. Results of in vivo evaluations of the long-acting activity of PEGylated (30 kD) insulin and PEGylated (40 kD) insulin are shown in the following Table 6 and FIG. 7.

TABLE 6

Results of in vivo long-acting activity of PEG (30 kD)-107, PEG (40 kD)-107, PEG (30 kD)-156 and PEG (40 kD)-156

| | | control | Humulin R | Detemir | PEG(30 kD)-107 | PEG(40 kD)-107 | PEG(30 kD)-156 | PEG(40 kD)-156 |
|---|---|---|---|---|---|---|---|---|
| Dosage (mg/kg) | | 0 | 0.04 | 0.2 | 0.1 | 0.1 | 0.1 | 0.1 |
| Numbers of Animals | | 4 | 4 | 4 | 4 | 4 | 4 | 4 |
| Weight (g) | | 130 | 126 | 130 | 125 | 142 | 133 | 133 |
| AOC % | | | 4.55 | 5.92 | 44.43 | 49.40 | 56.44 | 56.76 |
| IP | | | 0 | 100 | 282.5 | 285.0 | 289.8 | 297.4 |
| Blood glucose value (%) | 0 | 100 | 100.00 | 100.00 | 100.00 | 100.00 | 100.00 | 100.00 |
| | 1 | 100 | 42.42 | 104.15 | 96.80 | 91.48 | 91.83 | 104.61 |
| | 2 | 100 | 20.48 | 74.83 | 81.25 | 80.58 | 78.64 | 83.09 |
| | 3 | 100 | 28.59 | 46.46 | 86.28 | 91.16 | 85.00 | 95.43 |
| | 4 | 100 | 37.50 | 23.36 | 85.71 | 83.59 | 68.84 | 83.55 |
| | 6 | 100 | 90.10 | 17.11 | 99.95 | 90.46 | 51.95 | 85.54 |
| | 8 | 100 | 119.53 | 32.52 | 99.93 | 75.16 | 42.96 | 75.72 |
| | 10 | 100 | 115.95 | 94.89 | 86.79 | 60.73 | 28.67 | 53.28 |
| | 12 | 100 | 111.03 | 110.45 | 53.75 | 33.90 | 22.28 | 40.84 |
| | 16 | 100 | | | 27.91 | 24.32 | 23.52 | 33.61 |
| | 20 | 100 | | | 26.69 | 22.07 | 25.64 | 25.00 |
| | 24 | 100 | | | 25.59 | 18.25 | 21.91 | 23.78 |
| | 28 | 100 | | | 16.79 | 16.32 | 23.12 | 19.47 |
| | 32 | 100 | | | 13.82 | 14.38 | 18.00 | 16.22 |
| | 36 | 100 | | | 21.29 | 15.02 | 17.74 | 20.28 |
| | 40 | 100 | | | 24.64 | 20.74 | 23.01 | 25.44 |
| | 44 | 100 | | | 30.52 | 26.78 | 25.04 | 25.79 |
| | 48 | 100 | | | 28.49 | 28.51 | 27.41 | 31.25 |
| | 52 | 100 | | | 39.14 | 39.00 | 29.26 | 34.18 |
| | 56 | 100 | | | 65.78 | 42.57 | 32.61 | 37.64 |
| | 60 | 100 | | | 81.03 | 43.12 | 39.00 | 39.85 |
| | 64 | 100 | | | 105.43 | 63.25 | 50.70 | 42.13 |
| | 68 | 100 | | | 132.02 | 87.42 | 66.91 | 43.95 |
| | 74 | 100 | | | 132.73 | 90.82 | 77.16 | 48.04 |
| | 78 | 100 | | | 138.56 | 128.71 | 96.09 | 65.20 |
| | 82 | 100 | | | | | 111.74 | 78.79 |
| | 86 | 100 | | | | | 135.91 | 137.17 |

Conclusion:
The results in Table 6 and FIG. 7 show that PEG (30 kD)-107 (IP: 282.5) maintained stable blood glucose levels for up to 48 hrs in mice;

PEG (40 kD)-107 (IP: 285.0) maintained stable blood glucose levels for up to 60 hrs in mice;

PEG (30 kD)-156 (IP: 289.8) maintained stable blood glucose levels for up to 56 hrs in mice; and PEG (40 kD)-156 (IP: 297.4) maintained stable blood glucose level for up to 76 hrs in mice, which were significantly better than that of the positive control.

The invention claimed is:

1. A human insulin analogue or a physiologically acceptable salt thereof having an A chain and a B chain as follows:

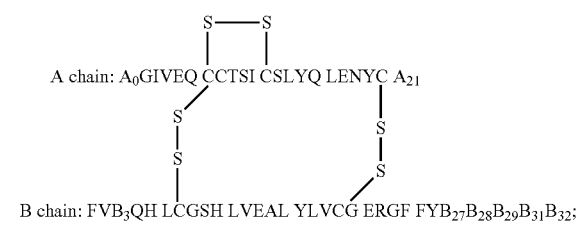

wherein:
$A_0$ is omitted;
$A_{21}$ is N or G;
$B_3$ is N;
$B_{27}$ is T;
$B_{28}$ is D;
$B_{29}$ is K;
$B_{30}$ is E;
$B_{31}$ and $B_{32}$ are omitted;
the ε-amino group of the lysine residue at B29 is optionally acylated; and
optionally, the α-amino group at the N-terminus of the A chain or B chain is acylated.

2. The human insulin analogue or the physiologically acceptable salt thereof according to claim 1, wherein the sequences of the A chain and B chain are selected from the group consisting of:

A chain:                    SEQ ID NO: 1
GIVEQCCTSICSLYQLENYCN

B chain:                    SEQ ID NO: 10
FVNQHLCGSHLVEALYLVCGERGFFYTDKE
and

A chain:                    SEQ ID NO: 2
GIVEQCCTSICSLYQLENYCG

B chain:                    SEQ ID NO: 10.
FVNQHLCGSHLVEALYLVCGERGFFYTDKE

3. The human insulin analogue or the physiologically acceptable salt thereof according to claim 1, wherein the human insulin analogue is PEGylated.

4. The human insulin analogue or the physiologically acceptable salt thereof according to claim 1, wherein the human insulin analogue is modified by PEG, and the molecular weight of the PEG molecule is 5-100 kD; and the PEG molecule is a branched-chain or straight-chain type.

5. An expressed precursor used for the preparation of the human insulin analogue or the physiologically acceptable salt thereof according to claim 1, having the following formula (I):

B-R1-A                                                          (I)

wherein:
R1 is a peptide fragment having 0 to 5 amino acid residues, wherein the peptide fragment consists of alanine (A), lysine (K) and arginine (R); and
A and B correspond to the A chain and B chain of the human insulin analogue, respectively, wherein the expressed precursor is selected from the group consisting of: SEQ ID NO: 19: FVNQHLCGSHLVEALYL-VCGERGFFYTDKEKRGIVEQCCTSICSLY-QLENYCN, and SEQ ID NO:77: FVNQHLQGSHLVEALYLVCGERGFFYTD-KEKRGIVEQCCTSIQSLYQLENYCG.

6. A DNA encoding the expressed precursor according to claim 5.

7. An expression vector comprising the DNA according to claim 6.

8. A host cell transformed with the expression vector according to claim 7.

9. The host cell according to claim 8, wherein the host cell is a bacterium.

10. The host cell according to claim 8, wherein the host cell is yeast.

11. An insulin derivative, comprising an acylated group connected to the α-amino group at the N-terminus of the A chain or B chain, or to the ε-amino group of a lysine residue at B29 of the human insulin analogue or the physiologically acceptable salt thereof of claim 1, the insulin derivative has the following formula:

S-W-X—Y—Z wherein S is the human insulin analogue according to claim 1;
-W-X—Y—Z is an acylated group of the human insulin analogue, wherein, W is selected from the group consisting of:
(i) a group having a di-acyl structure of —OC(CH2)mCO—, wherein m is an integer of 2 to 10, an amide bond is formed between one carboxyl group on the structure and the α-amino group of the N-terminal amino acid residue of the A-chain or B-chain, or the ε-amino group of a Lys residue existing in the B-chain of the human insulin analogue; and
(ii) an α-amino acid residue with a carboxyl group on the side chain or a peptide having 2 to 4 α-amino acids with a carboxyl group on the side chain, wherein an amide bond is formed between the residue or the peptide and the α-amino group at the N-terminus of the A-chain or B-chain, or the ε-amino group at a Lys residue existing in the B-chain of the human insulin analogue;

X is selected from the group consisting of:
(i) —CO—; and
(ii) a diamino compound comprising a carboxyl group, wherein an amide bond is formed between one of the α-amino groups of the diamino compound and the carboxyl group of W;
provided that:
a) when W is an α-amino acid residue or a peptide having 2 to 4 α-amino acids, the amide bond is formed between the amino group of W and the —CO— of X; or
b) when W is a group having a di-acyl structure, the X group is linked to the di-acyl structure via one of its amino groups;

Y is selected from the group consisting of:
(i) -A(CH$_2$)$_m$—, wherein m is an integer of 6 to 32, and A is absent or is CO—;
(ii) a bivalent hydrocarbon chain comprising an acyl group, which comprises 1, 2 or 3 —CH═CH— groups and a number of —CH2- groups sufficient to result in a total of 10-32 carbon atoms in the chain; and
(iii) a bivalent hydrocarbon chain having the formula of -B(CH$_2$)$_v$C$_6$H$_4$(CH$_2$)$_w$—, wherein B is absent or is CO—, each of v and w is an integer or one of them is 0, making v and w in the range of 6 to 30;
provided that:
a) when X is CO—, A or B is absent; or
b) when X is a diamino compound, A or B is CO—;

Z is selected from the group consisting of —OH, —NH$_2$, —COOH, —SO$_3$H, and —PO$_3$H.

12. The insulin derivative according to claim 11, wherein the acylated group -W-X—Y—Z is connected to the ε-amino group of a lysine residue at B29 of the human insulin analogue.

13. The insulin derivative according to claim 11, wherein the acylated group -W-X—Y—Z is connected to the α-amino group at the N-terminus of the A chain or B chain of the human insulin analogue.

14. The insulin derivative according to claim 11, wherein S is a human insulin analogue is consisting of: A chain: GIVEQCCTSICSLYQLENYCN (SEQ ID NO: 1) and B chain: FVNQHLCGSHLVEALYLVCGERGFFYTDKE (SEQ ID NO: 10).

15. The insulin derivative according to claim 11, wherein the acylated group -W-X—Y—Z is selected from the group consisting of:
N$^\alpha$—(HOOC(CH$_2$)$_{14}$CO)-γ-Glu;
N$^\alpha$—(HO(CH$_2$)$_{15}$CO)-γ-Glu; and
N$^\alpha$—(HOOC(CH$_2$)$_{14}$CO)—N$^\epsilon$-(3-acyl propionic acid *)-Lys, wherein * is the connection point to the insulin.

16. The insulin derivative according to claim 11, which is selected from the group consisting of:
B28D-N$^{\epsilon B29}$—(N$^\alpha$—(HOOC(CH$_2$)$_{14}$CO)-γ-Glu)-B30E human insulin;
B28D-N$^{\epsilon B29}$—(N$^\alpha$—(HO(CH$_2$)$_{15}$CO)-γ-Glu)-B30E human insulin; and
N$^\alpha$—(HOOC(CH$_2$)$_{14}$CO)—N$^\epsilon$—(OCCH$_2$CH$_2$CO-(B28D-N$^{\epsilon B29}$-B30E human insulin))-Lys-OH.

17. A pharmaceutical formulation comprising the insulin derivative of claim 11.

18. A method of treating type II diabetes, hyperglycemia, obesity or an insulin resistance syndrome in a subject in need of treatment thereof, the method comprising administering to the subject the pharmaceutical formulation according to claim 17.

19. A pharmaceutical formulation comprising a human insulin analogue or a physiologically acceptable salt thereof according to claim 1.

20. The pharmaceutical formulation according to claim 19, comprising the human insulin analogue or the physiologically acceptable salt thereof in a dissolved, amorphous and/or crystalline form.

21. The pharmaceutical formulation according to claim 19, comprising a long-term adjuvant, wherein the long-term adjuvant is present along with the human insulin analogue or the physiologically acceptable salt thereof in a manner of co-crystallization.

22. An injectable solution having insulin activity, wherein the solution comprises the pharmaceutical formulation according to claim 19 present in dissolved form.

23. A method of treating type II diabetes, hyperglycemia, obesity or an insulin resistance syndrome in a subject in need of treatment thereof, the method comprising administering to the subject the pharmaceutical formulation according to claim 19.

\* \* \* \* \*

SEQUENCE LISTING

<160> NUMBER OF SEQ ID NOS: 78

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 21
<212> TYPE: PRT
<213> ORGANISM: Artificial Sequence
<220> FEATURE:
<223> OTHER INFORMATION: Human Insulin Analogue A Chain

<400> SEQUENCE: 2

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 3
<211> LENGTH: 22
<212> TYPE: PRT
<213> ORGANISM: Artificial Sequence
<220> FEATURE:
<223> OTHER INFORMATION: Human Insulin Analogue A Chain

<400> SEQUENCE: 3

Arg Gly Ile Val Glu Gln Cys Cys Thr Ser Ile Cys Ser Leu Tyr Gln
1               5                   10                  15

Leu Glu Asn Tyr Cys Gly
            20

<210> SEQ ID NO 4
<211> LENGTH: 22
<212> TYPE: PRT
<213> ORGANISM: Artificial Sequence
<220> FEATURE:
<223> OTHER INFORMATION: Human Insulin Analogue A Chain

<400> SEQUENCE: 4

Arg Gly Ile Val Glu Gln Cys Cys Thr Ser Ile Cys Ser Leu Tyr Gln
1               5                   10                  15

Leu Glu Asn Tyr Cys Asn
            20

<210> SEQ ID NO 5
<211> LENGTH: 29
<212> TYPE: PRT
<213> ORGANISM: Artificial Sequence
<220> FEATURE:
<223> OTHER INFORMATION: Human Insulin Analogue B Chain

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 6
<211> LENGTH: 30
<212> TYPE: PRT
<213> ORGANISM: Artificial Sequence
<220> FEATURE:
<223> OTHER INFORMATION: Human Insulin Analogue B Chain

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Glu Arg
            20                  25                  30

<210> SEQ ID NO 7
<211> LENGTH: 29
<212> TYPE: PRT
<213> ORGANISM: Artificial Sequence
<220> FEATURE:
<223> OTHER INFORMATION: Human Insulin Analogue B Chain

<400> SEQUENCE: 7

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Glu
            20                  25

<210> SEQ ID NO 8
<211> LENGTH: 30
<212> TYPE: PRT
<213> ORGANISM: Artificial Sequence
<220> FEATURE:
<223> OTHER INFORMATION: Human Insulin Analogue B Chain

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Glu
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Human Insulin Analogue B Chain

<400> SEQUENCE: 9

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Glu
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Human Insulin Analogue B Chain

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Glu

-continued

<210> SEQ ID NO 11
<211> LENGTH: 32
<212> TYPE: PRT
<213> ORGANISM: Artificial Sequence
<220> FEATURE:
<223> OTHER INFORMATION: Human Insulin Analogue B Chain

<400> SEQUENCE: 11

Phe Val Asp Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Human Insulin Analogue B Chain

<400> SEQUENCE: 12

Phe Val Asp Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Human Insulin Analogue B Chain

<400> SEQUENCE: 13

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Arg Arg
            20                  25                  30

<210> SEQ ID NO 14
<211> LENGTH: 29
<212> TYPE: PRT
<213> ORGANISM: Artificial Sequence
<220> FEATURE:
<223> OTHER INFORMATION: Human Insulin Analogue B Chain

<400> SEQUENCE: 14

Phe Val Asp Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 15
<211> LENGTH: 29
<212> TYPE: PRT
<213> ORGANISM: Artificial Sequence
<220> FEATURE:
<223> OTHER INFORMATION: Human Insulin Analogue B Chain

<400> SEQUENCE: 15

Phe Val Asn Gln His Leu Cys Gly Ser His Leu Val Glu Ala Leu Tyr
1               5                   10                  15

```
Leu Val Cys Gly Glu Arg Gly Phe Phe Tyr Thr Lys Glu
            20                  25

<210> SEQ ID NO 16
<211> LENGTH: 30
<212> TYPE: PRT
<213> ORGANISM: Artificial Sequence
<220> FEATURE:
<223> OTHER INFORMATION: Human Insulin Analogue B Chain

<400> SEQUENCE: 16

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Glu
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: Human Insulin Analogue B Chain

<400> SEQUENCE: 17

Phe Val Asp Gln His Leu Cys Gly Ser His Leu Val Glu Ala Leu Tyr
1               5                   10                  15

Leu Val Cys Gly Glu Arg Gly Phe Phe Tyr Thr Pro Lys Arg
            20                  25                  30

<210> SEQ ID NO 18
<211> LENGTH: 29
<212> TYPE: PRT
<213> ORGANISM: Artificial Sequence
<220> FEATURE:
<223> OTHER INFORMATION: Human Insulin Analogue B Chain

<400> SEQUENCE: 18

Phe Val Asp Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 19
<211> LENGTH: 53
<212> TYPE: PRT
<213> ORGANISM: Artificial Sequence
<220> FEATURE:
<223> OTHER INFORMATION: Human Insulin Analogue Precursor

<400> SEQUENCE: 19

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Glu Lys Arg
            20                  25                  30

Gly Ile Val Glu Gln Cys Cys Thr Ser Ile Cys Ser Leu Tyr Gln Leu
            35                  40                  45

Glu Asn Tyr Cys Asn
    50

<210> SEQ ID NO 20
<211> LENGTH: 53
<212> TYPE: PRT
<213> ORGANISM: Artificial Sequence
<220> FEATURE:
```

<223> OTHER INFORMATION: Human Insulin Analogue Precursor

<400> SEQUENCE: 20

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Glu Glu Lys Arg
            20                  25                  30

Gly Ile Val Glu Gln Cys Cys Thr Ser Ile Cys Ser Leu Tyr Gln Leu
        35                  40                  45

Glu Asn Tyr Cys Gly
    50

<210> SEQ ID NO 21
<211> LENGTH: 53
<212> TYPE: PRT
<213> ORGANISM: Artificial Sequence
<220> FEATURE:
<223> OTHER INFORMATION: Human Insulin Analogue Precursor

<400> SEQUENCE: 21

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Glu Glu Lys Arg
            20                  25                  30

Gly Ile Val Glu Gln Cys Cys Thr Ser Ile Cys Ser Leu Tyr Gln Leu
        35                  40                  45

Glu Asn Tyr Cys Asn
    50

<210> SEQ ID NO 22
<211> LENGTH: 53
<212> TYPE: PRT
<213> ORGANISM: Artificial Sequence
<220> FEATURE:
<223> OTHER INFORMATION: Human Insulin Analogue Precursor

<400> SEQUENCE: 22

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Lys Arg
            20                  25                  30

Gly Ile Val Glu Gln Cys Cys Thr Ser Ile Cys Ser Leu Tyr Gln Leu
        35                  40                  45

Glu Asn Tyr Cys Asn
    50

<210> SEQ ID NO 23
<211> LENGTH: 51
<212> TYPE: PRT
<213> ORGANISM: Artificial Sequence
<220> FEATURE:
<223> OTHER INFORMATION: Human Insulin Analogue Precursor

<400> SEQUENCE: 23

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Arg Gly Ile
            20                  25                  30

Val Glu Gln Cys Cys Thr Ser Ile Cys Ser Leu Tyr Gln Leu Glu Asn
        35                  40                  45

Tyr Cys Asn
    50

<210> SEQ ID NO 24
<211> LENGTH: 54
<212> TYPE: PRT
<213> ORGANISM: Artificial Sequence
<220> FEATURE:
<223> OTHER INFORMATION: Human Insulin Analogue Precursor

<400> SEQUENCE: 24

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Glu Arg Ala Ala
            20                  25                  30

Lys Gly Ile Val Glu Gln Cys Cys Thr Ser Ile Cys Ser Leu Tyr Gln
        35                  40                  45

Leu Glu Asn Tyr Cys Asn
    50

<210> SEQ ID NO 25
<211> LENGTH: 52
<212> TYPE: PRT
<213> ORGANISM: Artificial Sequence
<220> FEATURE:
<223> OTHER INFORMATION: Human Insulin Analogue Precursor

<400> SEQUENCE: 25

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Glu Lys Arg Gly
            20                  25                  30

Ile Val Glu Gln Cys Cys Thr Ser Ile Cys Ser Leu Tyr Gln Leu Glu
        35                  40                  45

Asn Tyr Cys Asn
    50

<210> SEQ ID NO 26
<211> LENGTH: 53
<212> TYPE: PRT
<213> ORGANISM: Artificial Sequence
<220> FEATURE:
<223> OTHER INFORMATION: Human Insulin Analogue Precursor

<400> SEQUENCE: 26

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Glu Lys Arg
            20                  25                  30

Gly Ile Val Glu Gln Cys Cys Thr Ser Ile Cys Ser Leu Tyr Gln Leu
        35                  40                  45

Glu Asn Tyr Cys Asn
    50

<210> SEQ ID NO 27
<211> LENGTH: 53
<212> TYPE: PRT
<213> ORGANISM: Artificial Sequence
<220> FEATURE:
<223> OTHER INFORMATION: Human Insulin Analogue Precursor

<400> SEQUENCE: 27

```
Phe Val Asp Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Gly Ile Val Glu Gln Cys Cys Thr Ser Ile Cys Ser Leu Tyr Gln Leu
        35                  40                  45

Glu Asn Tyr Cys Gly
    50
```

<210> SEQ ID NO 28
<211> LENGTH: 52
<212> TYPE: PRT
<213> ORGANISM: Artificial Sequence
<220> FEATURE:
<223> OTHER INFORMATION: Human Insulin Analogue Precursor

<400> SEQUENCE: 28

```
Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Arg Arg Gly
            20                  25                  30

Ile Val Glu Gln Cys Cys Thr Ser Ile Cys Ser Leu Tyr Gln Leu Glu
            35                  40                  45

Asn Tyr Cys Asn
    50
```

<210> SEQ ID NO 29
<211> LENGTH: 51
<212> TYPE: PRT
<213> ORGANISM: Artificial Sequence
<220> FEATURE:
<223> OTHER INFORMATION: Human Insulin Analogue Precursor

<400> SEQUENCE: 29

```
Phe Val Asp Gln His Leu Cys Gly Ser His Leu Val Glu Ala Leu Tyr
1               5                   10                  15

Leu Val Cys Gly Glu Arg Gly Phe Phe Tyr Thr Pro Lys Arg Gly Ile
            20                  25                  30

Val Glu Gln Cys Cys Thr Ser Ile Cys Ser Leu Tyr Gln Leu Glu Asn
        35                  40                  45

Tyr Cys Asn
    50
```

<210> SEQ ID NO 30
<211> LENGTH: 52
<212> TYPE: PRT
<213> ORGANISM: Artificial Sequence
<220> FEATURE:
<223> OTHER INFORMATION: Human Insulin Analogue Precursor

<400> SEQUENCE: 30

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Glu Lys Arg Gly
            20                  25                  30

Ile Val Glu Gln Cys Cys Thr Ser Ile Cys Ser Leu Tyr Gln Leu Glu
            35                  40                  45

Asn Tyr Cys Gly
    50
```

<210> SEQ ID NO 31
<211> LENGTH: 51
<212> TYPE: PRT
<213> ORGANISM: Artificial Sequence
<220> FEATURE:
<223> OTHER INFORMATION: Human Insulin Analogue Precursor

<400> SEQUENCE: 31

Phe Val Asp Gln His Leu Cys Gly Ser His Leu Val Glu Ala Leu Tyr
1               5                  10                  15

Leu Val Cys Gly Glu Arg Gly Phe Phe Tyr Thr Pro Lys Arg Gly Ile
            20                  25                  30

Val Glu Gln Cys Cys Thr Ser Ile Cys Ser Leu Tyr Gln Leu Glu Asn
        35                  40                  45

Tyr Cys Gly
    50

<210> SEQ ID NO 32
<211> LENGTH: 162
<212> TYPE: DNA
<213> ORGANISM: Artificial Sequence
<220> FEATURE:
<223> OTHER INFORMATION: DNA Encoding Human Insulin Analogue Precursor

<400> SEQUENCE: 32
tttgtgaacc aacacctgtg cggctcacac ctggtggaag ctctctacct agtgtgcggg      60
gaacgaggct tcttctacac acccaagacc aagcgtggca ttgtggaaca atgctgtacc     120
agcatctgct ccctctacca gctggagaac tactgcaact ag                        162

<210> SEQ ID NO 33
<211> LENGTH: 156
<212> TYPE: DNA
<213> ORGANISM: Artificial Sequence
<220> FEATURE:
<223> OTHER INFORMATION: DNA Encoding Human Insulin Analogue Precursor

<400> SEQUENCE: 33
tttgtgaacc aacacctgtg cggctcacac ctggtggaag ctctctacct agtgtgcggg      60
gaacgaggct tcttctacac acccaagcgt ggcattgtgg aacaatgctg taccagcatc     120
tgctccctct accagctgga gaactactgc aactag                               156

<210> SEQ ID NO 34
<211> LENGTH: 165
<212> TYPE: DNA
<213> ORGANISM: Artificial Sequence
<220> FEATURE:
<223> OTHER INFORMATION: DNA Encoding Human Insulin Analogue Precursor

<400> SEQUENCE: 34
ttcgtcaacc agcacttgtg tggttcccat ttggttgagg ctctgtactt ggtctgtgga      60
gaaagaggtt tcttttacac caaggaaaga gctgctaaag gtatcgttga gcaatgttgc     120
acctctattt gttccctgta tcagttggaa aactactgca actaa                     165

<210> SEQ ID NO 35
<211> LENGTH: 159
<212> TYPE: DNA
<213> ORGANISM: Artificial Sequence
<220> FEATURE:
<223> OTHER INFORMATION: DNA Encoding Human Insulin Analogue Precursor

<400> SEQUENCE: 35

```
ttcgtcaacc agcacttgtg tggttcccat ttggttgagg ctctgtactt ggtctgtgga        60
gaaagaggtt tcttttacac caaggaaaaa agaggtatcg ttgagcaatg ttgcacctct      120
atttgttccc tgtatcagtt ggaaaactac tgcaactaa                             159
```

```
<210> SEQ ID NO 36
<211> LENGTH: 162
<212> TYPE: DNA
<213> ORGANISM: Artificial Sequence
<220> FEATURE:
<223> OTHER INFORMATION: DNA Encoding Human Insulin Analogue Precursor

<400> SEQUENCE: 36
ttcgtcaacc agcacttgtg tggttcccat ttggttgagg ctctgtactt ggtctgtgga        60
gaaagaggtt tcttttacac caagcctgaa aaaagaggta tcgttgagca atgttgcacc      120
tctatttgtt ccctgtatca gttggaaaac tactgcaact aa                         162
```

```
<210> SEQ ID NO 37
<211> LENGTH: 162
<212> TYPE: DNA
<213> ORGANISM: Artificial Sequence
<220> FEATURE:
<223> OTHER INFORMATION: DNA Encoding Human Insulin Analogue Precursor

<400> SEQUENCE: 37
ttcgtcaagc agcacttgtg tggttcccat ttggttgagg ctctgtactt ggtctgtgga        60
gaaagaggtt tcttttacac ccctgaagaa aaaagaggta tcgttgagca atgttgcacc      120
tctatttgtt ccctgtatca gttggaaaac tactgcaact aa                         162
```

```
<210> SEQ ID NO 38
<211> LENGTH: 162
<212> TYPE: DNA
<213> ORGANISM: Artificial Sequence
<220> FEATURE:
<223> OTHER INFORMATION: DNA Encoding Human Insulin Analogue Precursor

<400> SEQUENCE: 38
ttcgtcaacc agcacttgtg tggttcccat ttggttgagg ctctgtactt ggtctgtgga        60
gaaagaggtt tcttttacac cgataaggaa aaaagaggta tcgttgagca atgttgcacc      120
tctatttgtt ccctgtatca gttggaaaac tactgcaact aa                         162
```

```
<210> SEQ ID NO 39
<211> LENGTH: 162
<212> TYPE: DNA
<213> ORGANISM: Artificial Sequence
<220> FEATURE:
<223> OTHER INFORMATION: DNA Encoding Human Insulin Analogue Precursor

<400> SEQUENCE: 39
ttcgtcgatc agcacttgtg tggttcccat ttggttgagg ctctgtactt ggtctgtgga        60
gaaagaggtt tcttttacac ccctaagact agaagaggta tcgttgagca atgttgcacc      120
tctatttgtt ccctgtatca gttggaaaac tactgcggtt aa                         162
```

```
<210> SEQ ID NO 40
<211> LENGTH: 159
<212> TYPE: DNA
<213> ORGANISM: Artificial Sequence
<220> FEATURE:
<223> OTHER INFORMATION: DNA Encoding Human Insulin Analogue Precursor

<400> SEQUENCE: 40
```

-continued ttcgtcaagc agcacttgtg tggttcccat ttggttgagg ctctgtactt ggtctgtgga      60
gaaagaggtt tcttttacac ccctgaaaga agaggtatcg ttgagcaatg ttgcacctct     120
atttgttccc tgtatcagtt ggaaaactac tgcaactaa                            159

<210> SEQ ID NO 41
<211> LENGTH: 156
<212> TYPE: DNA
<213> ORGANISM: Artificial Sequence
<220> FEATURE:
<223> OTHER INFORMATION: DNA Encoding Human Insulin Analogue Precursor

<400> SEQUENCE: 41
ttcgtcgatc agcacttgtg tggttcccat ttggttgagg ctctgtactt ggtctgtgga      60
gaaagaggtt tcttttacac ccctaagaga ggtatcgttg agcaatgttg cacctctatt     120
tgttccctgt atcagttgga aaactactgc aactaa                               156

<210> SEQ ID NO 42
<211> LENGTH: 170
<212> TYPE: DNA
<213> ORGANISM: Artificial Sequence
<220> FEATURE:
<223> OTHER INFORMATION: DNA Encoding Human Insulin Analogue Precursor

<400> SEQUENCE: 42
ttcgtcaacc agcacttgtg tggttcccat ttggttgagg ctctgtactt ggtctgtgga      60
gaaagaggtt tcttttacac caaggaaaaa agaggtatcg ttgagcaatg ttgcacctct     120
atttgttccc tgtatcagtt ggaaaactac tgcggttaag aattccctag                170

<210> SEQ ID NO 43
<211> LENGTH: 174
<212> TYPE: DNA
<213> ORGANISM: Artificial Sequence
<220> FEATURE:
<223> OTHER INFORMATION: DNA Encoding Human Insulin Analogue Precursor

<400> SEQUENCE: 43
ttcgtcaagc agcacttgtg tggttcccat ttggttgagg ctctgtactt ggtctgtgga      60
gaaagaggtt tcttttacac ccctgaagaa aaagaggta tcgttgagca atgttgcacc     120
tctatttgtt ccctgtatca gttggaaaac tactgcggtt aagaattccc tagg           174

<210> SEQ ID NO 44
<211> LENGTH: 168
<212> TYPE: DNA
<213> ORGANISM: Artificial Sequence
<220> FEATURE:
<223> OTHER INFORMATION: DNA Encoding Human Insulin Analogue Precursor

<400> SEQUENCE: 44
ttcgtcgatc agcacttgtg tggttcccat ttggttgagg ctctgtactt ggtctgtgga      60
gaaagaggtt tcttttacac ccctaagaga ggtatcgttg agcaatgttg cacctctatt     120
tgttccctgt atcagttgga aaactactgc ggttaagaat tccctagg                  168

<210> SEQ ID NO 45
<211> LENGTH: 50
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 45 gtgcgggaa cgaggcttct tctacacacc caagaccaag cgtggcattg				50

<210> SEQ ID NO 46
<211> LENGTH: 50
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 46
gtagagggag cagatgctgg tacagcattg ttccacaatg ccacgcttgg				50

<210> SEQ ID NO 47
<211> LENGTH: 50
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 47
tgcggctcac acctggtgga agctctctac ctagtgtgcg gggaacgagg				50

<210> SEQ ID NO 48
<211> LENGTH: 50
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 48
ctgactgaat tctagttgca gtagttctcc agctggtaga gggagcagat				50

<210> SEQ ID NO 49
<211> LENGTH: 50
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 49
acttgctcga gaaaagattt gtgaaccaac acctgtgcgg ctcacacctg				50

<210> SEQ ID NO 50
<211> LENGTH: 32
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 50
cttctacaca cccaagcgtg gcattgtgga ac				32

<210> SEQ ID NO 51
<211> LENGTH: 32
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 51
gttccacaat gccacgcttg ggtgtgtaga ag                                           32

<210> SEQ ID NO 52
<211> LENGTH: 46
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 52
ggtttctttt acaccaagga aagagctgct aaaggtatcg ttgagc                            46

<210> SEQ ID NO 53
<211> LENGTH: 46
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 53
gctcaacgat acctttagca gctctttcct tggtgtaaaa gaaacc                            46

<210> SEQ ID NO 54
<211> LENGTH: 37
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 54
ggtttctttt acaccaagga aaaagaggt atcgttg                                       37

<210> SEQ ID NO 55
<211> LENGTH: 37
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 55
caacgatacc tcttttttcc ttggtgtaaa agaaacc                                      37

<210> SEQ ID NO 56
<211> LENGTH: 40
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 56
ggtttctttt acaccaagcc tgaaaaaaga ggtatcgttg                                   40

<210> SEQ ID NO 57
<211> LENGTH: 40
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 57
caacgatacc tctttttca ggcttggtgt aaaagaaacc 40

<210> SEQ ID NO 58
<211> LENGTH: 32
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 58
gagaaaagat tcgtcaagca gcacttgtgt gg                                  32

<210> SEQ ID NO 59
<211> LENGTH: 32
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 59
ccacacaagt gctgcttgac gaatcttttc tc                                  32

<210> SEQ ID NO 60
<211> LENGTH: 39
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 60 gtttcttta caccctgaa gaaaaagag gtatcgttg                              39

<210> SEQ ID NO 61
<211> LENGTH: 39
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 61
caacgatacc tcttttttct tcagggggtgt aaaagaaac                          39

<210> SEQ ID NO 62
<211> LENGTH: 40
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 62
ggtttctttt acaccgataa ggaaaaaaga ggtatcgttg                          40

<210> SEQ ID NO 63
<211> LENGTH: 40
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 63
caacgatacc tctttttttcc ttatcggtgt aaaagaaacc                    40

<210> SEQ ID NO 64
<211> LENGTH: 42
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 64
ggtttctttt acaccccctaa gactagaaga ggtatcgttg ag                  42

<210> SEQ ID NO 65
<211> LENGTH: 42
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 65
ctcaacgata cctcttctag tcttagggggt gtaaaagaaa cc                  42

<210> SEQ ID NO 66
<211> LENGTH: 34
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 66
gttggaaaac tactgcggtt aagaattccc tagg                           34

<210> SEQ ID NO 67
<211> LENGTH: 34
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 67
cctagggaat tcttaaccgc agtagttttc caac                           34

<210> SEQ ID NO 68
<211> LENGTH: 34
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 68
cttttacacc cctgaaagaa gaggtatcgt tgag                           34

<210> SEQ ID NO 69
<211> LENGTH: 34
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 69
ctcaacgata cctcttcttt cagggggtgta aaag                          34

<210> SEQ ID NO 70
<211> LENGTH: 36
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 70
cttttacacc cctaagagag gtatcgttga gcaatg                                 36

<210> SEQ ID NO 71
<211> LENGTH: 36
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 71
cattgctcaa cgatacctct cttaggggtg taaaag                                 36

<210> SEQ ID NO 72
<211> LENGTH: 34
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 72
gttggaaaac tactgcggtt aagaattccc tagg                                   34

<210> SEQ ID NO 73
<211> LENGTH: 34
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 73
cctagggaat tcttaaccgc agtagttttc caac                                   34

<210> SEQ ID NO 74
<211> LENGTH: 34
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 74
gttggaaaac tactgcggtt aagaattccc tagg                                   34

<210> SEQ ID NO 75
<211> LENGTH: 34
<212> TYPE: DNA
<213> ORGANISM: Artificial Sequence
<220> FEATURE:
<223> OTHER INFORMATION: Primer for Construction of Expression Vector
      Comprising Human Insulin Analogue Precursor

<400> SEQUENCE: 75
cctagggaat tcttaaccgc agtagttttc caac                                   34

<210> SEQ ID NO 76
<211> LENGTH: 34
<212> TYPE: DNA
<213> ORGANISM: Artificial Sequence
<220> FEATURE:
<223> OTHER INFORMATION: Primer for Construction of Expression Vector Comprising Human Insulin Analogue Precursor

<400> SEQUENCE: 76
gttggaaaac tactgcggtt aagaattccc tagg    34

<210> SEQ ID NO 77
<211> LENGTH: 53
<212> TYPE: PRT
<213> ORGANISM: Artificial Sequence
<220> FEATURE:
<223> OTHER INFORMATION: Human Insulin Analogue Precursor

<400> SEQUENCE: 77

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Glu Lys Arg
            20                  25                  30

Gly Ile Val Glu Gln Cys Cys Thr Ser Ile Cys Ser Leu Tyr Gln Leu
        35                  40                  45

Glu Asn Tyr Cys Gly
    50

<210> SEQ ID NO 78
<211> LENGTH: 30
<212> TYPE: PRT
<213> ORGANISM: Artificial Sequence
<220> FEATURE:
<223> OTHER INFORMATION: Human Insulin Analogue B Chain

<400> SEQUENCE: 78

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30